US009975914B2

(12) United States Patent
Ala'Aldeen et al.

(10) Patent No.: US 9,975,914 B2
(45) Date of Patent: May 22, 2018

(54) ANTIMICROBIAL PREPARATION AND USES THEREOF

(71) Applicant: Akeso Biomedical, Inc., Waltham, MA (US)

(72) Inventors: Dlawer Ala'Aldeen, Watford (GB); Jafar Mahdavi, Nottingham (GB); Panos Soultanas, Nottingham (GB)

(73) Assignee: Akeso Biomedical, Inc., Waltham, MA (US)

( * ) Notice: Subject to any disclaimer, the term of this patent is extended or adjusted under 35 U.S.C. 154(b) by 0 days. days.

(21) Appl. No.: 15/234,937

(22) Filed: Aug. 11, 2016

(65) Prior Publication Data

US 2017/0044197 A1  Feb. 16, 2017

Related U.S. Application Data

(63) Continuation-in-part of application No. PCT/US2015/044603, filed on Aug. 11, 2015.

(60) Provisional application No. 62/296,386, filed on Feb. 17, 2016, provisional application No. 62/334,746, filed on May 11, 2016.

(51) Int. Cl.

| | | |
|---|---|---|
| *A61K 31/295* | (2006.01) | |
| *C07F 15/02* | (2006.01) | |
| *A61K 45/06* | (2006.01) | |
| *A61K 31/7036* | (2006.01) | |
| *G02B 1/04* | (2006.01) | |
| *C09D 5/14* | (2006.01) | |
| *A23K 20/195* | (2016.01) | |
| *A23K 20/20* | (2016.01) | |
| *A23K 50/10* | (2016.01) | |
| *A23K 50/30* | (2016.01) | |
| *A23K 50/60* | (2016.01) | |
| *A23K 50/75* | (2016.01) | |
| *A23L 33/10* | (2016.01) | |
| *A23L 33/16* | (2016.01) | |
| *A01N 37/44* | (2006.01) | |
| *A61K 31/197* | (2006.01) | |
| *A61K 31/198* | (2006.01) | |
| *A01N 59/16* | (2006.01) | |
| *A61L 2/16* | (2006.01) | |

(52) U.S. Cl.

CPC ............ *C07F 15/025* (2013.01); *A01N 37/44* (2013.01); *A01N 59/16* (2013.01); *A23K 20/195* (2016.05); *A23K 20/30* (2016.05); *A23K 50/10* (2016.05); *A23K 50/30* (2016.05); *A23K 50/60* (2016.05); *A23K 50/75* (2016.05); *A23L 33/127* (2016.08); *A23L 33/16* (2016.08); *A61K 31/197* (2013.01); *A61K 31/198* (2013.01); *A61K 31/295* (2013.01); *A61K 31/7036* (2013.01); *A61K 45/06* (2013.01); *A61L 2/16* (2013.01); *C09D 5/14* (2013.01); *G02B 1/043* (2013.01); *A23V 2002/00* (2013.01)

(58) Field of Classification Search
CPC ... C07F 15/02; A61K 31/7036; A61K 31/197; A61K 31/295; A61K 33/127; G02B 1/043
USPC .................................................. 424/404, 417
See application file for complete search history.

(56) References Cited

U.S. PATENT DOCUMENTS

| | | |
|---|---|---|
| 5,879,697 A | 3/1999 | Ding |
| 6,139,879 A | 10/2000 | Taylor |
| 7,247,338 B2 | 7/2007 | Pui |
| 8,028,646 B2 | 10/2011 | Pui |
| 2003/0054090 A1 | 3/2003 | Hansen |
| 2004/0265427 A1 | 12/2004 | Boren |
| 2007/0249553 A1 | 10/2007 | Newell |
| 2007/0269495 A1 | 11/2007 | Ashmead |
| 2009/0182044 A1 | 7/2009 | Ashmed |
| 2012/0276280 A1 | 11/2012 | Doshi |
| 2014/0057987 A1 | 2/2014 | Vinson |

FOREIGN PATENT DOCUMENTS

| | | |
|---|---|---|
| EP | 2286666 | 2/2011 |
| WO | 03040351 | 5/2003 |
| WO | 2005055944 | 6/2005 |

(Continued)

OTHER PUBLICATIONS

Pradines et al.; Title: In Vitro Potentiation of Antibiotic Activities by a Catecholate Iron Chelator against Chloroquine-Resistant Plasmodium falciparum; Antimicrob Agents Chemother. Jan. 2002; 46(1): 225-228.*

Akiyama, et al., "Adherence characteristics and susceptibility to antimicrobial agents of *Staphylococcus aureus* strains isolated from skin infections and atopic dermatitis," J Dermatol Sci., 23 (3):155-60 (2000).

Akiyama, et al., "Assessment of *Streptococcus pyogenes* microcolony formation in infected skin by confocal laser scanning microscopy," J Dermatol Sci., 32(3):193-9 (2003b).

Akiyama, et al., "Confocal laser scanning microscopic observation of glycocalyx production by *Staphylococcus aureus* in skin lesions of bullous impetigo, atopic dermatitis and pemphigus foliaceus," Br J Dermatol., 148(3):526-32 (2003).

(Continued)

*Primary Examiner* — Yanzhi Zhang
(74) *Attorney, Agent, or Firm* — Pabst Patent Group, LLP

(57) ABSTRACT

A method of enhancing the growth of an animal is provided. The method includes causing the animal to ingest or absorb an effective amount of a preparation obtainable by a process including, bringing a tyrosinate moiety into contact with an Fe(III)-containing substance, optionally wherein the tyrosinate moiety is tyrosine and it is brought into contact with the Fe(III)-containing substance in the presence of a base, or wherein the tyrosinate moiety is a tyrosine salt and it is brought into contact with an Fe(III)-containing substance. Methods for inhibiting, reducing, or preventing biofilm formation or buildup on a surface; the treatment of, inhibition of growth of, and inhibition of colonization by, bacteria, both in biological and non-biological environments; disinfecting surfaces, potentiating the effects of antibiotics and other anti-microbial agents, and increasing the sensitivity of bacteria and other microorganisms, to anti-microbial agents are also provided.

12 Claims, 14 Drawing Sheets

(56) References Cited

FOREIGN PATENT DOCUMENTS

| | | |
|---|---|---|
| WO | 2006046017 | 5/2006 |
| WO | 2008105983 | 9/2008 |
| WO | 2013121214 | 8/2013 |

OTHER PUBLICATIONS

Atta, et al., "Synthesis and spectroscopic investigations of iron oxide nano-particles for biomedical applications in the treatment of cancer cells", J Mol Structure, 1086:246-54 (2015).

Barco, et al., "D-( )-Quinic acid: a chiron store for natural product synthesis," Tetrahedron:Asymmety, 8(21):3515-45 (1997).

Bek-Thomson, et al., "Acne is not associated with yet-uncultured bacteria," J. Clin. Microbiol., 46(10):3355-60 (2008).

Buchanan, "Beta-barrel proteins from bacterial outer membranes: structure, function and refolding," Curr. Opin. Struc. Biol., 9(40):455-61 (1999).

Burkhart, et al., "Dermatophytoma: Recalcitrance to treatment because of existence of fungal biofilm," J Am Acad Dermatol., 47(4):629-31 (2002).

Campbell and Hasinoff, "Ferrous sulfate reduces levodopa bioavailability: Chelation as a possible mechanism," Clin. Pharmacol. Ther., 45:220-5 (1989).

Cervantes, et al., "a1-2 Fucosylated Chains (H-2, H-1, and Lewisb) are the Main Human Milk Receptor Analogs for Campylobacter", Campylobacters, Helicobacters, and Related Organisms, pp. 653-658, Springer Science US (1996).

Creek, et al., "Stable isotope-assisted metabolomics for network-wide metabolic pathway elucidation," Analytical Chem., 84:8442-7 (2012).

Dasti, et al., "Campylobacter jejuni: a brief overview on pathogenicity-associated factors and disease-mediating mechanisms", Int J Med Microbiol.,300:205-11 (2010).

Golden, et al., "Identification of Motility and Autoagglutination Campylobacter jejuni Mutants by Random Transposon Mutagenesis," Infect Immun., 70 (4):1761-71 (2002).

Hedin, "*Staphylococcus epidermidis*—hospital epidemiology and the detection of methicillin resistance," Scand J Infect Dis Suppl., 90:1-59 (1993).

Hoiby, et al., "Antibiotic resistance of bacterial biofilms," Int J Antimicrob Agents, 35(4):322-32 (2010).

Humphrey, et al., "Campylobacter jejuni in dairy cows and raw milk," Epidemiol Infect., 98:263-9 (1987).

Humphrey, et al., "Isolation of *Campylobacter* species from non-clinical samples," Public Health Lab Serv Microbiol Digest., 13:86-8 (1996).

Humphrey, et al., "Techniques for the optimum recovery of cold injured Campylobacter jejuni from milk or water," J Appl Bacteriol. 61:125-32. (1986).

Huyer, et al., "Outer membrane porin protein of Campylobacter jejuni," FEMS Microbiol. Lett., 37(3):247-50 (1986).

Iime, Glossary of Medical education terms, http://www.iime.oeg/glossaey.htm, pp. 1-39 retrieved from the interner Mar. 24, 2011.

Ikezawa, et al., "A Role of Staphyococcus aureus, Interleukin-18, Nerve Growth Factor and Semaphorin 3A, an Axon Guidance Molecule, in Pathogenesis and Treatment of Atopic Dermatitis," Allergy Asthma Immunol Res., 2 (4):235-46 (2010).

International Search Report for corresponding PCT/US2016/046623 dated Sep. 26, 2016.

Jacobs-Reitsma, et al., "Epidemiology of *Campylobacter* spp. at two Dutch broiler farms," Epidemiol Infect., 114:413-21 (1995).

James, et al., "Biofilms in chronic wounds," Wound Repair Regen., 16(1):37-44 (2008).

Kazwala, et al., "Factors responsible for the introduction and spread of Campylobacter jejuni infection in commercial poultry production," Vet Rec. 1990;126:305-6. (1990).

Lee, et al., "Chitin Regulation of Immune Responses: An Old Molecule With New Roles," Curr Opin Immunol., 20(6):684-9 (2008).

Leung, et al., "Atopic dermatitis," Lancet, 361(9352):151-60 (2003).

Ley, et al., "Human gut microbes associated with obesity," Nature, 444 (7122):1022-3 (2006).

Ley, et al., "Obesity alters gut microbial ecology," PNAS, 102(31):11070-5 (2005).

Lindblom, et al., "Natural campylobacter colonization in chickens raised under different environmental conditions," J Hyg., 96:385-91 (1986).

Liu, et al., "Clinical practice guidelines by the infectious diseases society of america for the treatment of methicillin-resistant *Staphylococcus aureus* infections in adults and children," Clin Infect Dis., 52 (3):e18-55 (2011).

Madhavi, et al., "Helicobacter pylori SabA adhesin in persistent infection and chronic inflammation," Science, 297:573-8 (2002).

Mahdavi, et al., "A novel O-linked glycan modulates Campylobacter jejuni major outer membrane protein-mediated adhesion to human histo-blood group antigens and chicken colonization," Open Biol., 4:130202, doi: 10.1098/rsob.130202 (2014).

Meinersmann, et al., "Concerted evolution of duplicate fla genes in Campylobacter," Microbiology, 146(9):2283 (2000).

Menelaou, et al., "Synthesis and characterization of two new isostructural ion (III)-quinates from aqueous solutions," J Agrolimentary Processes Tech., XII:281-4 (2006).

Menelauo, et al., "pH-Specific Synthetic Chemistry and Solution Studies in the Binary System of Iron(III) with the r-Hydroxycarboxylate Substrate Quinic Acid Potential Relevance to Iron Chemistry in Plant Fluids," Inorg Chem., 48:1844-56 (2009).

Misawa et al., "Isolation of *Campylobacter* species from zoo animals and polymerase chain reaction-based randomamplified polymorphism DNA analysis," Vet Microbiol., 71:59-68 (2000).

Moran, "The role of endotoxin in infection: Helicobacter pylori and campylobacter jejuni", Subcell Biochem., 53:209-40 (2010).

Mowad, et al., "The role of extracellular polysaccharide substance produced by *Staphylococcus epidermidis* in miliaria," J Am Acad Dermatol., 33(5 Pt 1):729-33 (1995).

Nusbaum, et al., "Bofilms in dermatology," Skin Therapy Lett., 17(7):1-5 (2012).

Oberhuber, et al., "Blood groups Lewis(b) and ABH expression in gastric mucosa: lack of inter-relation with Helicobacter pylori colonisation and occurrence of gastric MALT lymphoma", Gut, 41:37-42 (1997).

Otto, "*Staphylococcus epidermidis*—the 'accidental' pathogen," Nat Rev Microbiol., 7(8):555-67 (2009).

Pearson, et al., "Colonization of broiler chickens by waterborne Campylobacter jejuni," Appl Environ Microbiol., 59:987-96 (1993).

Refat, et al., "Preparation, structural characterization and biological evaluation of L-tyrosinate metal ion complexes," J Mole Structure, 881:28-45 (2008).

Scheltems, et al., "PeakML/mzMatch: a file format, Java library, R library, and tool-chain for mass spectrometry data analysis," Analytical Chem., 83:2786-93 (2011).

Shevchenko, et al., "Mass spectrometric sequencing of proteins silver-stained polyacrylamide gels," Anal Chem., 68(5):8508 (1996).

Skirrow, "Epidemiology of Campylobacter enteritis," Int J Food Microbiol., 12:9-16 (1991).

Summer, et al., "Proposed minimum reporting standards for chemical analysis Chemical analysis Working Group (CAWG) Metabolomics Standards Initiative (MSI)," Metavolomics, 3:211-21 (2007).

Summer, et al., "Proposed quantitative and alphanumeric metabolite identification metric," Metavolomics, 10:1047-9 (2014).

Tautenhahn, et al., "Highly sensitive feature detection for high resolution LC/MS," BMC Bioinformatics, 9:504 (2008).

Turnbaugh, et al., "An obesity-associated gut microbiome with increased capacity for energy harvest," Nature, 444 (7122):1027-31 (2006).

Yamasaki, et al., "A combination of roxithromycin and imipenem as an antimicrobial strategy against biofilms formed by *Staphylococcus aureu*," J Antimicrob Chemother., 48 (4):573-7 (2001).

(56) References Cited

OTHER PUBLICATIONS

Refat, et al., "Preparation, structural characterization and biological evaluation of L-tyrosinate metal ion complexes", J Mole Structure, 881:28-45 (2008).

* cited by examiner

Where:
Y' = -O-, -OC(O)NH-, -OC(O)-
X' = -NHC(O)O-, -SiO$_3$-, -OPO$_3$-
HA = hydroxyapatite Where:
Y' = -O-, -OC(O)NH-, -OC(O)-
X' = -NHC(O)O-, -SiO$_3$-, -OPO$_3$-
HA = hydroxyapatite

ANTIMICROBIAL PREPARATION AND USES THEREOF

CROSS REFERENCE TO RELATED APPLICATION

This applications claims priority to WO 2016/025448 (PCT/US2015/044603) filed Aug. 11, 2015, U.S. Ser. No. 62/296,386 filed Feb. 17, 2016, and U.S. Ser. No. 62/334,746 filed May 11, 2016, all of which are incorporated by reference in their entirety.

FIELD OF THE INVENTION

This invention is in the field of preparations comprising Fe(III) complexes, that have a broad range of antimicrobial and other activities, and methods of making and using the preparations.

BACKGROUND OF THE INVENTION

A biofilm is an accumulation of microorganisms (bacteria, fungi, and/or protozoa, with associated bacteriophages and other viruses) embedded in a polysaccharide matrix and adherent to solid biological or non-biotic surfaces. Biofilms are medically important, accounting for over 80 percent of hospital-acquired microbial infections in the body. Examples include infections of the: oral soft tissues, teeth and dental implants; middle ear; gastrointestinal tract; urogenital tract; airway/lung tissue; eye; urinary tract prostheses; peritoneal membrane and peritoneal dialysis catheters, indwelling catheters for hemodialysis and for chronic administration of chemotherapeutic agents (Hickman catheters); cardiac implants such as pacemakers, prosthetic heart valves, ventricular assist devices, and synthetic vascular grafts and stents; prostheses, internal fixation devices, percutaneous sutures; and tracheal and ventilator tubing. The microorganisms tend to be far more resistant to antimicrobial agents and to be particularly difficult for the host immune system to render an appropriate response. Several bacterial pathogens have been shown to associate with, and in some cases, grow in biofilms, including *Legionella pneumophila, S. aureus, Listeria monocytogenes, Campylobacter* spp., *E. coli* O157:H7, *Salmonella typhimurium, Pseudomonas, Vibrio cholerae, S. epidermidis, E. faecalis,* and *Helicobacter pylori.*

Biofilms are remarkably difficult to treat with antimicrobials. Antimicrobials may be readily inactivated or fail to penetrate into the biofilm. In addition, bacteria within biofilms have increased (up to 1,000-fold higher) resistance to antimicrobial compounds, even though these same bacteria are sensitive to these agents if grown under planktonic conditions.

In addition, bacteria embedded within biofilms are resistant to both immunological and non-specific defense mechanisms of the body. Contact with a solid surface triggers the expression of a panel of bacterial enzymes, which catalyze the formation of sticky polysaccharides that promote colonization and protection. The structure of biofilms is such that immune responses may be directed only at those antigens found on the outer surface of the biofilm, and antibodies and other serum or salivary proteins often fail to penetrate into the biofilm. In addition, phagocytes are unable to effectively engulf a bacterium growing within a complex polysaccharide matrix attached to a solid surface. This causes the phagocyte to release large amounts of pro-inflammatory enzymes and cytokines, leading to inflammation and destruction of nearby tissues. Conventional therapy is characteristically ineffective against biofilms, as the minimum inhibitory concentration (MIC) of antimicrobial agents has been shown to be 10 to 1000 fold greater than for planktonic organisms (Hoiby, et al., *Int J Antimicrob Agents,* 35(4): 322-32 (2010).

It is an object to provide a preparation (and compositions comprising the preparation), methods of making thereof, and uses thereof for inhibiting or preventing biofilm formation or promoting biofilm dissolution from surfaces of interest.

SUMMARY OF THE INVENTION

A preparation comprising an Fe(III) complex, and suitable methods for making the preparation, has been found to provide a broad range of activity, particularly against a diverse array of bacteria. Compositions, articles and products comprising the preparation, are also described.

Compositions comprising the preparation, and methods and uses employing the preparation and/or compositions, for inhibiting, reducing, or preventing biofilm formation or buildup on a surface or to removing, dispersing, reducing, or eradicating biofilm on a surface are disclosed. Accordingly, preparations for inhibiting, reducing, or removing biofilm buildup in a subject and/or on an article or other item are provided. The preparations are effective against biofilms produced by a wide range of microbial species including, without limitation, *S. epidermidis, E. faecalis, E. coli, S. aureus, Campylobacter* spp. *H pylori* and *Pseudomonas,* alone, or in combination.

In an embodiment, an article or product, including medical devices having on the surface or dispersed therein one or more of the preparations as described further below. The surface may be a biological surface (such as a surface of a living human, animal or plant surface, or the surface of a dead or harvested animal or plant), or a non-biological surface including for example, plastics, polymers, biomaterials, and metals.

In another embodiment, the invention provides a preparation for the treatment of, inhibition of growth of, and inhibition of colonization by, bacteria, both in biological and non-biological environments.

In a further embodiment, the preparations are used for disinfecting surfaces, both in biological and non-biological environments, and products that have been coated with, or treated by, one or more of the preparations.

In another embodiment, the preparations are used for potentiating the effects of one or more antibiotics, increasing the sensitivity of bacteria (including antibiotic-resistant bacteria) to one or more antibiotics, and to reversing antibiotic resistance in bacteria.

BRIEF DESCRIPTION OF THE DRAWINGS

FIG. 6A shows the conjugation of FeQ to a calix[4]arene frame that contains a photoreactive functional group. FIG. 6B shows the conjugation of FeQ to a calix [4] arene frame wherein the photo-reactive functional group is positioned in a different location on the calix [4] arene frame compared to the structure of FIG. 6B. FIG. 6C shows the conjugation of FeQ to a calix[4] arene frame functionalized with two thiol groups.

FIG. 14A shows the results with PAO1N cultures.

DETAILED DESCRIPTION OF THE INVENTION

I. Definitions

Figure 1A:
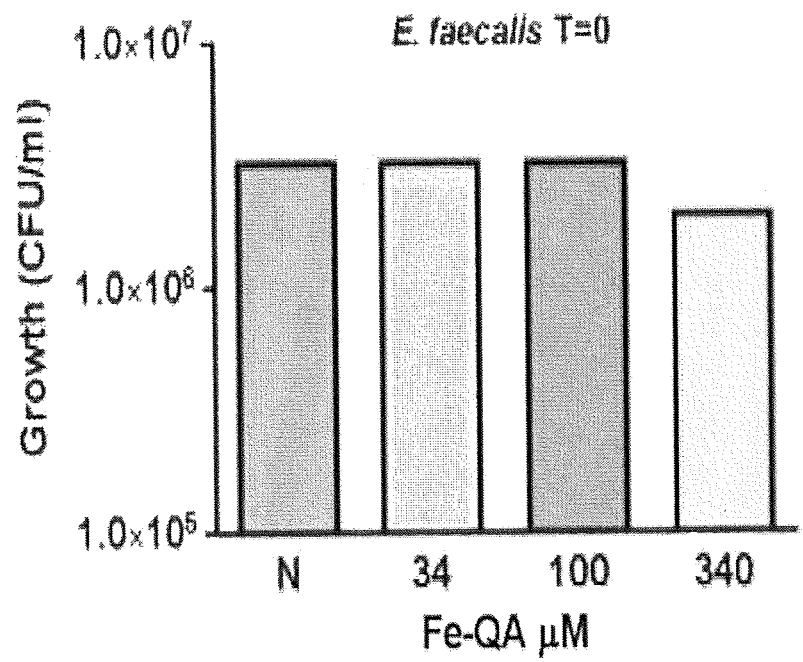
FIG. 1A is a bar graph showing biofilm formation by *Enterococcus faecalis* at time T=0 in the presence of absence of different concentrations of Fe-QA.

"Aerosol" as used herein refers to any preparation of a fine mist of particles, which can be in solution or a suspension, whether or not it is produced using a propellant.

"Biofilm" as used herein refers any group of microorganisms in which cells stick to each other on a surface.

A "cream" is a viscous liquid or semi-solid emulsion of either the "oil-in-water" or "water-in-oil type".

An "emulsion" is a composition containing a mixture of non-miscible components homogenously blended together.

"Gel" as used herein is a colloid in which the dispersed phase has combined with the continuous phase to produce a semisolid material, such as jelly.

"Cleaning formulation", as used herein, means a composition suitable for application to a surface for removing dirt and oils, for disinfecting, or a combination thereof. Cleaning formulations can be antibacterial, antimicrobial, or both. Cleaning formulations are suitable for use on the human skin, when none of the components of the composition are present at concentrations that cause significant signs of irritation when applied to human skin As used herein, "significant signs of irritation" include erythema, redness, and/or swelling at the site of injection or at the site of application, necrosis at the site of application, exfoliative dermatitis at the site of application, and severe pain that prevents daily activity and/or requires medical attention or hospitalization. Cleaning formulations can be suitable for use in the human buccal cavity. Cleaning formulations can be suitable for use with articles that, subsequent to exposure and optionally with residual levels of cleaning composition present on and/or in the article, will then be contacted with the human skin or other part of the human body, such as wherein the article (e.g. a denture) will be contacted with the buccal cavity, or will be contacted with the eye (e.g. a contact lens). Cleaning formulations can be suitable for use with foodstuffs and/or their packaging and may, for example, be suitable for cleaning meat products and/or carcasses used in the production of meat products. Cleaning formulations may be suitable for cleaning equipment used in food production. Cleaning formulations may be suitable for use in cleaning medical devices, including implantable medical devices. Many other types of cleaning formulations may also be provided by the present invention, further examples of which are discussed in further sections of this application.

"Chronic wound" as used herein refers to a wound that fails to progress through an orderly and timely sequence of repair or a wound that does not respond to treatment and/or the demands of treatment are beyond the patient's physical health, tolerance or stamina Many wounds that are first considered to be acute wounds ultimately become chronic wounds due to factors still not well understood. One significant factor is the transition of planktonic bacteria within the wound to form a biofilm.

"Inhibition" or "inhibiting" of biofilm formation as used herein refers to a decrease of biofilm associated microorganism formation and/or growth.

A "lotion" is a low- to medium-viscosity liquid formulation.

"Oil" as used herein refers to a composition containing at least 95% wt. of a lipophilic substance. Examples of lipophilic substances include but are not limited to naturally occurring and synthetic oils, fats, fatty acids, lecithins, triglycerides and combinations thereof.

An "ointment" is a semisolid preparation containing an ointment base and optionally one or more active agents.

"Parenteral administration", as used herein, means administration by any method other than through the digestive tract or non-invasive topical or regional routes.

"Patient" or "subject" to be treated and/or used in accordance with any of the aspect as described herein refers to either a human or non-human animal such as a primate, non-human primate, laboratory animal, farm animal, livestock, or a domestic pet. Exemplary animals can optionally include chickens, particularly a meat-type chicken such as broiler chicken, or an egg-laying chicken such as a pullet or hen, or a breeder chicken. Also optionally included without limitation are other poultry, such as a turkey, geese, quail or ducks, or livestock, such as cattle, sheep, goats or swine, alpaca, banteng, bison, camel, cat, deer, dog, donkey, gayal, guinea pig, horse, llama, mule, rabbit, reindeer, water buffalo, yak, although the skilled person will appreciate that other animals, including zoo animals, captive animals, game animals, fish (include freshwater and saltwater fish, farmed fish, and ornamental fish), other marine and aquatic animals, including shellfish such as, but not limited to, oysters, mussels, clams, shrimps, prawns, lobsters, crayfish, crabs, cuttlefish, octopus, and squid, domestic animals such as cats and dogs, rodents (such as mice, rats, guinnea pigs, hamsters), and horses, are also included, as well as any other domestic, wild and farmed animal, including mammals, marine animals, amphibians, birds, reptiles, insects and other invertebrates.

"Pharmaceutically acceptable" as used herein refers to those compounds, materials, compositions, and/or dosage forms which are, within the scope of sound medical judgment, suitable for use in contact with the tissues of human beings and animals (such as one or more of the animal "patients" or "subjects" as discussed above) without excessive toxicity, irritation, allergic response, or other problems or complications commensurate with a reasonable benefit/risk ratio.

"Pharmaceutically acceptable salt", as used herein, refers to derivatives of the compounds defined herein, wherein the parent compound is modified by making acid or base salts thereof.

"Therapeutically effective" or "effective amount" as used herein means that the amount of the composition used is of sufficient quantity to ameliorate one or more causes or symptoms of a condition, bacterial colonization, disease or disorder. Such amelioration only requires a reduction or alteration, not necessarily elimination. As used herein, the terms "therapeutically effective amount" "therapeutic amount" and "pharmaceutically effective amount" are synonymous. One of skill in the art can readily determine the proper therapeutic amount.

"Treatment", "treating", or "alleviating" as used in connection with a disease or infection refers to an intervention performed with the intention of altering or inhibiting the pathology of a disorder.

II. Compositions and Methods of Use Thereof

Preparations containing the iron complexes, methods of use and benefits thereof, can be summarized as:

Enhancement of animal growth;

Potentiating the effect of antibiotics and other antimicrobial agents, and addressing antibiotic resistance;

Inhibition of formation, and treatment of preformed, biofilms; treating microbial infections reducing microbial colonization; and disinfecting surfaces.

Preparations containing the iron complexes can be used to enhance animal growth. Numerous examples of this effect are provided in the Examples.

It has been discovered that the preparations containing the iron complexes are particularly useful in treating or preventing infection by antibiotic-resistant microorganisms. The preparation may be administered in order to cause microorganisms to lose their resistance to antibiotics.

Inhibition of Formation, and Treatment of Preformed, Biofilms

In one aspect the preparations containing the iron complexes have a broad range of action in treating and dispersing pre-existing biofilms, and inhibiting the development of biofilms, created by a wide range of bacterial and other microbial sources. This action is effective in a diverse array of environments.

1. Organisms to be Treated, Inhibited, or Killed

Biofilms are usually found on solid substrates submerged in or exposed to an aqueous solution, although they can form as floating mats on liquid surfaces. Biofilms can form on a myriad of surfaces. "Biofilm" as used herein refers any group of microorganisms in which cells stick to each other on a surface. For example, biofilms can grow in showers very easily since they provide a moist and warm environment for the biofilm to thrive. Biofilms can form inside water and sewage pipes and cause clogging and corrosion. Biofilms on floors and counters can make sanitation difficult in food preparation areas. Biofilms can form in cooling- or heating-water systems and are known to reduce heat transfer in these systems One method, or use, includes administering an effective amount of the one or more preparations to inhibit biofilm formations, or alternatively, to reduce and/or remove biofilm formation. The one or more preparations may be administered alone, or in combination with an antimicrobial agent, such as an antibiotic.

In other embodiments, the method includes contacting a surface with an effective amount of the one or more preparations, to inhibit biofilm buildup, reduce built up biofilm, and/or remove built up biofilm. "Contacting" includes, but is not limited to, touching, impregnating, compounding, mixing, integrating, coating, spraying, dipping, flushing, irrigating, and wiping. In certain embodiments, it may be desirable to provide continuous delivery of one or more preparations to the surface or system being treated. The compositions can be used to coat, impregnate, flush, or rinse a surface of tubing or a medical device, especially an insertable medical device. Tubing includes, but is not limited to, disposable, permanent, and indwelling catheters, long term urinary devices, tissue bonding urinary devices, wound drain tubes, ventricular catheters, endotracheal tubes, breathing tubes, feeding tubes, dairy lines, oil and gas pipeline and drinking water lines. When an object is tubing (e.g., dental unit waterline, a dairy line, a food and beverage processing line, etc.), a composition may be poured into the tubing and both ends of the tubing clamped such that the composition is retained within the lumen of the tubing. The tubing is then allowed to remain filled with the composition for a period of time sufficient to remove substantially all of the microorganisms from at least one surface of the object, generally, for at least about 1 minute to about 48 hours. Alternatively, tubing may be flushed by pouring a composition into the lumen of the tubing for an amount of time sufficient to prevent substantial growth of all biofilm embedded microorganisms. Such flushing may be required only once, or may be required at regular intervals over the lifetime of use of the tubing. Concentrations of active components in a composition may vary as desired or necessary to decrease the amount of time the composition is in contact with a medical device.

The methods allow disinfection, inhibition, or prevention of biofilm formation on the surfaces being treated and reduction of transmission of biofilm forming microorganisms from the surface to another surface. The number of the bacterial colony forming units (cfu) on the surface being treated with the one or more preparations may be reduced by 50%, by 60%, by 70%, by 80%, by 90% or by 100%, or, the buildup of bacterial colony forming units on the treated surface may be reduced by 50%, by 60%, by 70%, by 80%, by 90% or by 100%.

2. Methods of Administration

In one embodiment, the preparations and formulations, derivatives thereof and combinations thereof for use can be administered topically to a subject in need thereof in an effective amount to prevent or treat a microbial infection, by inhibiting buildup of biofilm or to reduce and/or remove built up biofilm.

Any suitable topical formulation can be used, for example as described below, including emulsions, lotions, creams, ointments, gels, or foams.

The compositions may be used alone or in combination with known antimicrobial agents, such as those described further below.

Other modes of administration can include:

Parenteral administration, which may include administration to a patient intravenously, intradermally, intraarterially, intraperitoneally, intralesionally, intracranially, intraarticularly, intraprostatically, intrapleurally, intratracheally, intravitreally, intratumorally, intramuscularly, subcutaneously, subconjunctivally, intravesicularly, intrapericardially, intraumbilically, by injection, and by infusion, for example as further described.C.1 of this application, below. Parenteral administration can include the use of formulations as described herein which are formulated for controlled release including immediate release, delayed release, extended release, pulsatile release, and combinations thereof,.

The preparations can be incorporated into injectable/implantable solid or semi-solid implants, such as polymeric implants.

Enteral administration, including administration in the form of suitable oral dosage forms such as tablets, capsules, solutions, suspensions, syrups, and lozenges,. Optionally, enteral administration may include administration of controlled release enteral formulations, including oral dosage forms, such as capsules, tablets, solutions, and suspensions, which are formulated for controlled release, including extended and/or delayed release.

The administration of one or more disinfecting formulations or cleaning formulations.

3. Hospital and Other Environments

The methods and uses may be practiced in the hospital and also in other medical and non-medical environments in order to address, inhibit, treat, ameliorate and/or disrupt biofilms for the treatment and/or prophylaxis of subjects (including humans and animals) in need thereof.

In other embodiments, the one or more preparations containing the iron complexes can be incorporated into coatings used to coat medical devices, and other articles.

Suitable coating methods are known in the art. Methods for coating medical devices are disclosed for example in U.S. Publication Nos. 20030054090 and 20120276280 and U.S. Pat. Nos. 5,879,697, 7,247,338 and U.S. Pat. No. 8,028,646.

In a preferred embodiment, the one or more preparations are combined with polymers, and coated on medical devices or other articles. Suitable polymers include, but are not limited, to poly(lactides); poly(glycolides); poly(lactide-co-glycolides); poly(lactic acid); poly(glycolic acid); poly(lactic acid-co-glycolic acids); polycaprolactones; poly(orthoesters); polyanhydrides; poly(phosphazenes); polyhydroxyalkanoates [including poly-3-hydroxybutyrate, poly-3-hydroxybutyrate-co-3-hydroxyvalerate (PHBV), poly-4-hydroxybutyrate, poly-3-hydroxybutyrate-co-4-hydroxybutyrate]; synthetically or biologically prepared polyesters (including polyesters with one or more of the following monomeric units: glycolic, lactic; trimethylene carbonate, p-dioxanone, or ε-caprolactone); poly(lactide-co-caprolactones); polyesters; polycarbonates; tyrosine polycarbonates; polyamides (including synthetic and natural polyamides, polypeptides, and poly(amino acids)); polyesteramides; poly(dioxanones); poly(alkylene alkylates); polyethers (such as polyethylene glycol, PEG, and polyethylene oxide, PEO); polyvinyl pyrrolidones or PVP; polyurethanes; polyetheresters; polyacetals; polycyanoacrylates; poly(oxyethylene)/poly(oxypropylene) copolymers; polyacetals, polyketals; polyphosphates; (phosphorous-containing) polymers; polyphosphoesters; polyalkylene oxalates; polyalkylene succinates; poly(maleic acids); chitin; chitosan; modified chitosan; collagen; silk; biocompatible polysaccharides; biocompatible copolymers (including block copolymers or random copolymers); hydrophilic or water soluble polymers, such as polyethylene glycol, (PEG) or polyvinyl pyrrolidone (PVP), with blocks of other biocompatible or biodegradable polymers, for example, poly(lactide), poly(lactide-co-glycolide, or polycaprolcatone or combinations thereof, polymers and copolymers of ethylene and propylene, including ultra-high molecular weight polyethylene, ultra-high molecular weight polypropylene, nylon, polyesters such as poly(ethylene terephthalate), poly(tetrafluoroethylene), polyurethanes, poly(ether-urethanes), poly(methylmethacrylate), polyether ether ketone, polyolefins, Dacron, latex, silicones, polymeric cements, and poly(ethylene oxide).

In another preferred embodiment, the components of one or more preparations can be first conjugated with other agents that have an affinity for, or can react with, a surface, and thereby immobilized on a surface. For example, the components of one or more preparations can be tethered to a linkage that can be photo-activated to bind to a surface, or activated via another mechanism.

Examples of devices and articles that can be coated using the compositions include tubing and other surface medical devices, such as urinary catheter, stents, mucous extraction catheter, suction catheter, umbilical cannula, contact lenses, intrauterine devices, intravaginal and intraintestinal devices, endotracheal tubes, bronchoscopes, dental prostheses and orthodontic devices, dentures, teeth, surgical instruments, dental instruments, tubing, dental water lines, dental drain tubes, fabrics, paper, indicator strips (e.g., paper indicator strips or plastic indicator strips), adhesives (e.g., hydrogel adhesives, hot-melt adhesives, or solvent-based adhesives), bandages, tissue dressings or healing devices and occlusive patches, and any other surface devices used in the medical field. Devices may include electrodes, external prostheses, fixation tapes, compression bandages, and monitors of various types. Medical devices also include any device that may be placed at the insertion or implantation site such as the skin near the insertion or implantation site, and which include at least one surface which is susceptible to colonization by biofilm embedded microorganisms. In one specific embodiment, a composition is integrated into an adhesive, such as tape, thereby providing an adhesive, which may prevent growth or proliferation of biofilm embedded microorganisms on at least one surface of the adhesive. Medical devices include surfaces of equipment in operating rooms, emergency rooms, hospital rooms, clinics, and bathrooms.

In a particularly preferred embodiment the following devices may be coated with the one or more preparations, or one or more components thereof: catheters, including central venous catheters, urinary catheters, dialysis catheters, and indwelling catheters (for example, catheters for hemodialysis and for administration of chemotherapeutic agents), cardiac implants including mechanical heart valves, stents, ventricular assist devices, pacemakers, cardiac rhythm management (CRM) devices, cardiac resynchronization therapy devices (CRTs), and implantable cardioverter defibrillators (ICDs), synthetic vascular grafts, arteriovascular shunts, cerebral spinal fluid shunts, cochlear devices, prosthetic joints, orthopedic implants, internal fixation devices, bone cements, percutaneous sutures, surgical mesh and surgical patches including hernia repair meshes and patches, breast reconstruction meshes and patches, meshes and patches for breast and face lifts, slings, and meshes and patches for pelvic floor reconstruction, tracheal and ventilator tubing, wound dressings, biological implants (including allografts, xenografts and autografts), penile implants, intrauterine devices, endotracheal tubes, and contact lenses.

Other articles that can be coated include articles for use in rearing animals. Other articles that can be coated include articles for use in the process of slaughter and/or processing the carcasses or parts thereof of animals. Other articles that can be coated include articles for the preparation and/or containment of food stuffs, including foodstuffs comprising raw or cooked meats, eggs, dairy products or other food products. The food products may be human and/or animal food products. Additional articles that can be coated include articles for the preparation and/or containment of drinks.

In another embodiment there is provided a method of disinfecting a surface, or protecting a surface against infection, in need thereof, the method comprising contacting the surface with an effective amount of one or more preparations containing the iron complexes wherein the components of the one or more preparations are coated onto the surface to be disinfected.

In some embodiments the one or more preparations may be applied to the surface in the form of a spray, an aerosol, or a foam.

The coated surface may, for example, be formed on the surface of an instrument selected from the group consisting of surgical instruments, cardiac and urinary catheters, implants, and ultrasound probes used in sterile body cavities.

The coated surface may, for example, be formed on the surface of a device selected from the group consisting of urinary catheter, stents, mucous extraction catheter, suction catheter, umbilical cannula, contact lenses, intrauterine devices, intravaginal and intraintestinal devices, endotracheal tubes, bronchoscopes, dental prostheses and orthodontic devices, surgical instruments, dental instruments, tubing, dental water lines, dental drain tubes, fabrics, paper, indicator strips (e.g., paper indicator strips or plastic indicator strips), adhesives (e.g., hydrogel adhesives, hot-melt adhesives, or solvent-based adhesives), bandages, tissue dressings or healing devices and occlusive patches, catheters, including central venous catheters, urinary catheters, dialysis catheters, and indwelling catheters, cardiac implants, mechanical heart valves, stents, ventricular assist devices, pacemakers, cardiac rhythm management (CRM) devices, cardiac resynchronization therapy devices (CRTs), and implantable cardioverter defibrillators (ICDs), synthetic vascular grafts, arteriovascular shunts, cerebral spinal fluid shunts, cochlear devices, prosthetic joints, orthopedic implants, internal fixation devices, bone cements, percutaneous sutures, surgical mesh and surgical patches including hernia repair mesh, breast reconstruction mesh, mesh for breast and face lifts, slings, and mesh for pelvic floor reconstruction, tracheal and ventilator tubing, wound dressings, biological implants, penile implants, intrauterine devices, endotracheal tubes, and contact lenses.

The coated surface may, for example, be formed on the surface of an article selected from the group consisting of an industrial pipeline, liquid distribution lines, oil and gas pipelines and cosmetic container.

The coated surface may, for example, be formed on the surface of, or be incorporated into, or onto, a household item, such as an item selected from the group consisting of household disinfectants; laundry detergent; cleaning supplies; equipment involved in the leeching process or mining; wound care; toothpaste; mouth wash; dental floss; toothpicks; chewable products (including food products); a mouth shield; a dental instrument; dentures; dental retainers; dental braces including plastic braces (such as Invisalign); bristles of toothbrushes; dental prostheses and orthodontic devices; chewable non-food items, foods, or toys, such as dog bones and biscuits; a vacuum system; HVAC ((heating, ventilation and air conditioning)) systems; vacuum cleaner bags; paint covering; wall coverings; window frames; doors; door frames; cooling towers; humidifiers; vacuum cleaners; filters such as a vacuum filter, a humidifier filter, hot tub filter, or a swimming pool filter; toys; plastic bottles; water jugs; tap and water spout; washing machines; dishwashers; animal water dishes; bathroom tiles and fixtures; sinks; showers; shower heads; toilets; toilets lids; toilet seats; sealants and grout; towels; TUPPERWARE®; dishes; cups; utensils such as forks, spoons, knives, and spatulas; bowls; food storage containers; beverage storage containers; cutting boards; dish drying trays; garbage bags; sinks; fish ponds; swimming pools; swimming pool liners; swimming pool skimmer; pond liners; bird baths; garden hose; water sprinkling lines; planters; and hot tubs.

The coated surface may, for example, be formed on the surface of, or incorporated into, or onto, an article, device or apparatus used in the rearing and/or transport of animals, such as a chicken, for example, a meat-type chicken such as broiler chicken, or an egg-laying chicken such as a pullet or hen, or a breeder chicken, other poultry, such as a turkey, geese, quail or ducks, or livestock, such as cattle, sheep, goats or swine, alpaca, banteng, bison, camel, cat, deer, dog, donkey, gayal, guinea pig, horse, llama, mule, rabbit, reindeer, water buffalo, yak, although the skilled person will appreciate that other feeds for animals, including zoo animals, captive animals, game animals, fish (include freshwater and saltwater fish, fan led fish, and ornamental fish), other marine and aquatic animals, including shellfish such as, but not limited to, oysters, mussels, clams, shrimps, prawns, lobsters, crayfish, crabs, cuttlefish, octopus, and squid, domestic animals such as cats and dogs, rodents (such as mice, rats, guinea pigs, hamsters), and horses, are also provided, as well as any other domestic, wild and fanned animal, including mammals, marine animals, amphibians, birds, reptiles, insects and other invertebrates. In some embodiments, the device or apparatus used in the rearing and/or transport of animals may be selected from an article, device or apparatus that is for the delivery and/or containment of animal feed and/or animal drinking water.

Also provided is a composition comprising one or more conjugated components of one or more preparations as defined above, and an article coated with one or more of the conjugated components of one or more preparations, or with the composition.

In one embodiment, the structure of the conjugated components of one or more preparations comprise hydroxyapatite or derivative thereof, and the conjugate is capable of anchoring, or is anchored to, a dental tissue.

For example, in a further embodiment, conjugated forms of the components of one or more preparations, such as those wherein the components of one or more preparations are conjugated to hydroxyapatite may be applied to tooth tissues, such as tooth enamel, dentin and pulp in order to prevent dental caries and infection. In another embodiment, the components of one or more preparations can be applied using photo-reactive chemistry, for example, using conjugated forms such as those shown in FIGS. 7A and B.

4. Industrial, Cosmetic and Consumer Applications

The compositions can be used to disinfect industrial surfaces, by preventing and/or removing biofilm buildup on such surfaces. In this embodiment, the formation of the biofilm may be prevented or inhibited, or a preformed biofilm may be removed by a method that comprises applying a composition comprising the one or more preparations containing the iron complexes onto a surface in need thereof, for example as a spray, foam, gel, powders; dish or laundry detergents (liquid or solid), surface wax, glass cleaner, etc.

5. Additional Medical Applications

In a further embodiment, the preparations containing the iron complexes and compositions comprising one or more of the preparations, can be used to treat any medical condition associated with biofilm formation as a result of microorganisms including, but not limited to, gram-negative and gram-positive bacteria, including *Pseudomonas, H. pylori, E. feacalis, Campylobacter, E. coli,* EPEC, UPEC and *Staphylococcus.*

III. Preparations and Compositions

A. Preparations

A preparation as defined herein is a preparation obtainable by a process including bringing a moiety such as a tyrosinate moiety into contact with an Fe(III)-containing substance. The Fe(III)-containing substance may be anhydrous or a hydrate substance. In preferred embodiments, the Fe(III)-containing substance is a hydrate such as, but not limited to, iron (III) chloride hexahydrate.

In one option, the tyrosinate moiety is tyrosine (for example, tyrosine may be added to the reaction mixture and converted to a tyrosinate ion through the action of a base) and it is brought into contact with the Fe(III)-containing substance in the presence of a base.

In another option, the tyrosinate moiety is a tyrosine salt and it is brought into contact with an Fe(III)-containing substance. In the option in which the tyrosinate moiety is a tyrosine salt, it may not be necessary to provide a base for its reaction with the Fe(III)-containing substance. The tyrosine salt may also be fully or partially dissolved in a solution prior to being brought into contact with the Fe(III)-containing substance.

The tyrosinate moiety may, for example, be selected from the group consisting of tyrosine (as noted above, for example, tyrosine may be added to the reaction mixture and converted to a tyrosinate ion through the action of a base), a salt of tyrosine, an anion of tyrosine, a double anion of tyrosine, a deprotonated tyrosine, mono-deprotonated tyrosine, and a double-deprotonated tyrosine. Examples of tyrosine salts that may be used include, without limitation, a sodium salt of tyrosine, a potassium salt of tyrosine, a lithium salt of tyrosine, and/or an ammonium salt of tyrosine.

In one embodiment of the process, the tyrosinate moiety thereof is provided in combination with a first solvent (e.g. in the form of a solution, suspension or slurry) prior to the tyrosinate moiety being brought into contact with the Fe(III)-containing substance. Prior to being brought into contact with the tyrosinate moiety thereof, the Fe(III)-containing substance may be provided either as a solid or in the form of a solution, suspension or slurry with a second solvent (which second solvent may be the same as or different from the first solvent). Preferably the first and second solvents are the same.

Particular solvents that may be mentioned in respect of the first and second solvents include aprotic polar solvents (e.g. acetonitrile), and more particularly polar protic solvents (e.g. water and $C_{1-4}$ alkyl alcohols), as well as mixtures of such solvents. Preferably the first and second solvents are the same and consist of one or more polar protic solvents.

The amount of solvent required will depend upon the amount of Fe(III)-containing substance and the amount of tyrosinate moiety to be used in the process. Preferably the total amount of the first and second solvents (e.g. water) used in the process is at least 300 mL.

The reaction between tyrosine and the Fe(III)-containing substance is facilitated by the presence of the base. The base may aid in deprotonating the tyrosine, thereby forming a deprotonated tyrosinate moiety, and increasing the solubility of the tyrosine (in an ionic form) in aqueous media. For example, the solubility of tyrosine is greatly increased in aqueous media in which the pH is raised to at least 8.5. In one embodiment the base is added to the tyrosine or other tyrosinate moiety thereof before the tyrosine or other tyrosinate moiety thereof is brought into contact with the Fe(III)-containing substance. Accordingly, the reaction process can also include the step of preparing or providing a tyrosine salt, such as a sodium salt of tyrosine, and then bringing together the tyrosine salt and the Fe(III)-containing substance in the presence of the base. Optionally, the salt may be a double salt of tyrosine. The salt may be in either a solid form, or in solution, at the time of being brought into contact with the Fe(III)-containing substance.

Suitable bases that may be used in the processes described herein include organic and inorganic bases. For example, the base may be an amine (e.g. a primary, secondary or, particularly, tertiary amine, such as triethylamine, trimethylamine or diethylisopropylamine), a nitrogen-based heterocycle (e.g. N-methylmorpholine or pyridine), an alkoxide (e.g. an alkali metal alkoxide, such as sodium ethoxide), a hydroxide salt (e.g. an ammonium or alkali metal hydroxide, such as lithium, sodium or potassium hydroxide) or, particularly, a carbonate or bicarbonate salt (e.g. an alkaline earth or, particularly, an alkali metal carbonate or bicarbonate). Particular bases that may be mentioned in this respect include trimethylamine, LiOH, KOH and NaOH.

The amount of base employed can vary, depending upon factors such as the particular base used, the identity of the solvent, the rate of reaction that is desired, etc. However, in certain embodiments of the process, the amount of base employed may be, for example, three, two or preferably one equivalents relative to the tyrosine.

When used herein, the term "aqueous media" refers to solutions of substances in which the solvent system comprises water, and optionally further comprises one or more other solvents, such as water-miscible organic solvents (e.g. a $C_{1-4}$ alkyl alcohol, such as ethanol, isopropanol or, particularly, methanol). Further, when pH values are referred to herein, those values may be determined by methods known to those skilled in the art (e.g. by potentiometric measurements using a working and a reference electrode), for example at room temperature (such as 25° C.).

The mixture containing the tyrosine, or other tyrosinate moiety, and base may be heated to an elevated temperature (e.g. to a temperature of at least 50° C.) either before or after the addition of the Fe(III)-containing substance. The mixture may be held at an elevated temperature for a sufficient period of time (e.g. for at least about 5 minutes, e.g. at least about 15 minutes) to allow the base to react with the tyrosine, or other tyrosinate moiety.

In one embodiment the tyrosine (or other tyrosinate moiety) used is predominantly L-tyrosine (or predominantly an L-tyrosinate moiety). For example, the tyrosine or other tyrosinate moiety used in the process comprises may be at least 30%, 40%, 50%, 60%, 70%, 80%, or 90% (e.g. at least 95%) by weight L-configuration.

In another embodiment, the molar ratio of the Fe(III)-containing substance to the tyrosine, or other tyrosinate moiety, in the reaction mixture is in the range of about 1:1 to 1:4, such as about 1:2 or, preferably, about 1:3. "About" in that context can optionally include one or more values selected from ±50%, 40%, 30%, 20%, 10% 5% or less of the stated value.

In another embodiment, the Fe(III)-containing substance comprises an Fe(III) complex, or salt or hydrate thereof, or an Fe(III) salt, or a hydrate thereof Particular Fe(III) complexes and salts that may be mentioned in this respect include Fe(III) halides (e.g. $FeCl_3$ and $FeBr_3$), $Fe(OH)_3$, $Fe_2(SO_4)_3$, $Fe(HSO_4)_3$, $Fe(NO_3)_3$, $Fe(acetylacetonate)_3$ ("Fe $(acac)_3$"), $Fe(acetate)_3$, $Fe(lactate)_3$ and Fe (III) phosphate. For the avoidance of doubt, salts and hydrated forms of these Fe(III) complexes and Fe(III) salts are also included (such as $FeCl_3.6H_2O$). In preferred embodiments, the Fe(III) complexes and Fe(III) salts are the hydrated forms.

The amount of Fe(III) used in the process relative to the amount of tyrosine, or other tyrosinate moiety, may vary. However, in preferred embodiments of the process, the process involves the use of about 3 (e.g. from 0.1, 0.5. 1, 2, 3, 4, 5, 6, 7, 8, 9, or 10) equivalents of tyrosine, or other tyrosinate moiety, relative to the Fe(III) employed.

The preparations used in the methods of the invention are obtainable by a process including bringing the tyrosinate moiety into contact with an Fe(III)-containing substance, optionally in the presence of a base, as discussed above. In certain embodiments, the bringing into contact step is performed over a period of about one to 8 hours. In some other embodiments, the bringing into contact step is performed over a period of about 1 hour, 2 hours, 3 hours, 4 hours, 5 hours, 6 hours, 7 hours, or 8 hours. In certain other embodiments, the bringing into contact step is performed over a period of less than 1 hour, preferably about 1-60 minutes, more preferably 1-25 minutes, most preferably 1-10 minutes. In certain embodiments, the bringing into contact step is performed over a period of about 5 minutes. Additional steps that may be involved in the processes include precipitation of a solid product, separation of the solid product from the mixture (e.g. by filtration), and drying the solid product. Further processing steps that may be involved include stirring, heating and/or cooling the reaction mixture. The use of the terms "consisting of" or "consisting essentially of" in the context of the process for obtaining the preparations is intended to refer to processes which may include any of the above-mentioned additional steps. However, the terms "consisting of" or "consisting essentially of" in the context of the process for obtaining the preparations refer to processes which typically do not involve any additional purification steps (e.g. such processes may not involve or include any purification steps which may separate one or more Fe(III)-containing products from another Fe(III)-containing product).

Thus, in a further embodiment of the method for producing a preparation as used by the invention, the preparation is obtainable by a process which consists of, or consists essentially of, bringing the tyrosinate moiety into contact with an Fe(III)-containing substance, optionally in the presence of a base, and further optionally further including one or more steps selected from the group consisting of stirring the mixture, heating the mixture, cooling the mixture, precipitating a solid product, separating a solid product from the mixture, and drying the product.

In certain embodiments of the method for producing the preparation contains an effective amount of an Fe(III)-containing product, which is obtained by the process described herein. The Fe(III)-containing product includes Fe(III) complex with a tyrosine or other tyrosinate moiety. In preferred embodiments, the preparation contains an effective amount of an Fe(III)-containing product, such as an Fe(III) complexed with a tyrosine or other tyrosinate moiety wherein at least some of the Fe(III)-containing product present in the preparation has a ratio of 1:3 of Fe(III): tyrosine or other tyrosinate moiety In a particular embodiment, the processes disclosed herein do not include the step of isolating Fe(tyrosine)₃ from the reaction mixture.

The preparation produced by the reaction process described herein will typically be a mixture of different substances, and may contain at least two Fe(III)-containing substances. The at least two Fe(III)-containing substances may optionally include Fe (III) that is bound by the amino group, acid group, or phenolic group of tyrosine, or other tyrosinate moiety, and can optionally include tyrosine, or other tyrosinate moiety, bound by two different Fe (III) atoms. Additional substances may also be present in the preparation, including one or more (including all) of the substances selected from the group consisting of tyrosine or other tyrosinate moiety (such as in the free base, or salt form) as well as by-products of the reaction (e.g. salts, such as NaCl). The identities of the by-products may vary depending on the identities of the starting materials used in the reaction (in particular, the identities of the Fe(III)-containing substance and the base). In a preferred embodiment, the preparation obtainable by the process defined herein comprises Fe(OH)₃. Additionally, or alternatively, in a further preferred embodiment, the preparation obtainable by the process defined herein comprises tyrosine or other tyrosinate moiety (e.g. in the free base or salt form; optionally in addition to Fe(OH)₃). It may be preferable for the amount of tyrosine, or other tyrosinate moiety, present (e.g., not complexed to iron and present in the free base or salt form) in the preparation to be less than 5% (w/w), although it can be difficult to solubilize tyrosine and therefore preparations may, in some circumstances comprise less than 5% detectable tyrosine but may, in practice, contain additional undetectable levels of tyrosine.

Optionally, the preparation may be obtainable by a process consisting of dissolving L-tyrosine (or other L-tyrosinate moiety), and LiOH in water, heating the mixture, separately dissolving FeCl₃ in water, and adding the FeCl₃ solution to the mixture after completion of the heating step. In a preferred embodiment, the preparation may be obtainable by a process consisting of dissolving L-tyrosine (30 mmol) and LiOH.H₂O (30 mmol) in water (250 ml), heating the mixture to 70° C. for 20 min, separately dissolving FeCl₃ (10 mmol) in water (3-5 ml) and adding the FeCl₃ solution to the tyrosine/LiOH mixture after completion of the heating step.

In another optional embodiment, the preparation may be different from the preparation obtainable by the foregoing process. Accordingly, the preparation may be obtainable by a process including bringing tyrosine, or other tyrosinate moiety (such as a tyrosine salt) thereof, into contact with an Fe(III)-containing substance, optionally in the presence of a base as hereinabove defined, provided that the process does not consist of dissolving L-tyrosine (30 mmol) and LiOH.H₂O (30 mmol) in water (250 ml), heating the mixture to 70° C. for 20 min, separately dissolving FeCl₃ (10 mmol) in water (3-5 ml) and adding the FeCl₃ solution to the tyrosine/LiOH mixture after completion of the heating step.

Preparations produced by the foregoing methods will preferably contain an effective amount of a complex of L-tyrosine (or other L-tyrosinate moiety) with Fe III (the complex is referred to herein as "Fe-Tyr", also in places is also denoted "Fe—Y"), such as a compound having the following structure:

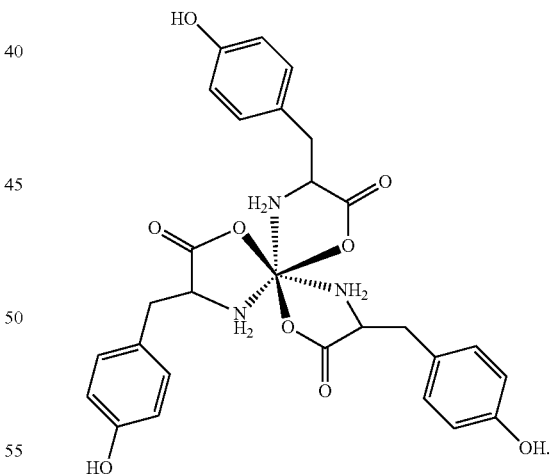

Additionally, or alternatively, in a further embodiment, the preparation obtainable by the process described herein contains an effective amount of a complex of tyrosine (or other tyrosinate moiety) with Fe III wherein the tyrosine (or other tyrosinate moiety coordinates the ferric ion via just the amino group of the tyrosine or other tyrosinate moiety. Additionally, or alternatively, in yet other embodiments, the preparation obtainable by the process described herein contains an effective amount of a complex of tyrosine (or other tyrosinate moiety) with Fe III wherein at least some of the complexes formed by the process are μ-oxo trimers. Iron carboxylates often form trimers, with a triply-bridging oxygen at the center. In yet another embodiment, the preparation obtainable by the process described herein contains an effective amount of a complex of tyrosine (or other tyrosinate moiety) with Fe III wherein the preparation includes μ-oxo trimeric complexes.

In a further embodiment, a preparation may be a preparation that inhibits biofilm formation by bacteria as measured in a plastic bead assay (such as in accordance with a method as described in the Examples), wherein the bacteria is grown in a medium containing the preparation to form a growth suspension of the bacteria at 0.0001 OD/ml, the growth suspension is allowed to grow with plastic coated UV beads (Lascells), and the beads are assayed after 24 hours for the presence of biofilm formation on the beads (by counting bacteria after release from the beads), and compared to a control group where the bacteria is not grown in the presence of the preparation. Preferably the preparation inhibits the binding of the bacteria to the plastic coated beads at a level of inhibition that is at, or at least, about 1%, 2%, 3%, 4%, more preferably at, or at least, about 5%, even more preferably at, or at least, about 10%, 20%, 30%, 40%, 50%, 60%, 70%, 80%, 90%, 95%, 96%, 97%, 98%, 99%, 100% or more of the level of inhibition of the binding of the bacteria to the plastic coated UV beads by either a preparation prepared according to the method of Example 14, or a complex of quinic acid with Fe III, in which Fe III is present at the same molar concentration. In particularly preferred embodiment, the bacteria can be *Enterococcus faecalis, Staphylococcus epidermidis, Staphylococcus aureus, Campylobacter jejuni, Pseudomonas aeruginosa,* Uropathogenic *Escherichia coli,* and Enteropathogenic *Escherichia coli.*

In a further embodiment, a preparation may be a preparation that inhibits binding of *Helicobacter pylori* to human gastric tissue (for example as determined by a method as described in Example 5) at a level of inhibition that is at, or at least, about 1%, 2%, 3%, 4%, more preferably at, or at least, about 5%, even more preferably at, or at least, about 10%, 20%, 30%, 40%, 50%, 60%, 70%, 80%, 90%, 95%, 96%, 97%, 98%, 99%, 100% or more of the level of inhibition of the binding of the bacteria to human gastric tissue by either a preparation prepared according to the method of Example 14, or a complex of quinic acid with Fe III, in which Fe III is present at the same molar concentration as measured by counting the average number of bacteria bound to the tissue.

In a further embodiment, a preparation may be a preparation that inhibits biofilm formation of a bacteria, but does not inhibit planktonic growth of the bacteria (for example, as determined using a method as described in Example 7), wherein the bacteria can be one or more of the following: *Enterococcus faecalis, Staphylococcus epidermidis, Staphylococcus aureus, Campylobacter jejuni, Pseudomonas aeruginosa,* Uropathogenic *Escherichia coli,* and Enteropathogenic *Escherichia coli.* Preferably the one or more preparations inhibit biofilm formation (for example, as measured by coverage rate in Example 7), at a level that is at, or at least, about 1%, 2%, 3%, 4%, more preferably at, or at least, about 5%, even more preferably at, or at least, about 10%, 20%, 30%, 40%, 50%, 60%, 70%, 80%, 90%, 95%, 96%, 97%, 98%, 99%, 100% or more of the level of biofilm inhibition by a preparation prepared according to the method of Example 14, or a complex of quinic acid with Fe III, in which Fe III is present at the same molar concentration.

In a further embodiment, a preparation may be a preparation for the treatment of cystic fibrosis. In one embodiment, the preparation may be delivered using a nebulizer spray. In another embodiment, the preparation may be delivered in liposomes for the treatment of patients with cystic fibrosis.

In a further embodiment, a preparation may be a preparation that prevents attachment of bacteria to a surface (for example, when determined in accordance with a method as described in Example 13), and the prevention of attachment of bacteria to the surface is at a level that is at, or at least, about 1%, 2%, 3%, 4%, more preferably at, or at least, about 5%, even more preferably at, or at least, about 10%, 20%, 30%, 40%, 50%, 60%, 70%, 80%, 90%, 95%, 96%, 97%, 98%, 99%, 100% or more of the level of bacteria attachment by a preparation prepared according to the method of Example 14, or a complex of quinic acid with Fe III, in which Fe III is present at the same molar concentration, for example as measured by optical density. In particularly preferred embodiment, the bacteria can be *Enterococcus faecalis, Staphylococcus epidermidis, Staphylococcus aureus, Campylobacter jejuni, Pseudomonas aeruginosa,* Uropathogenic *Escherichia coli,* and Enteropathogenic *Escherichia coli.*

The preparations may comprise components which are hydrates, or salts of hydrates. For example, the preparations may comprise be Fe-Tyr.$xH_2O$. The compounds may also be hydrates containing salts, for example hydrates with bases such as ammonium hydroxide, lithium hydroxide, sodium hydroxide or potassium hydroxide present.

In the case of preparations comprising compounds which are Fe III complexes comprising ligands bound to the iron centre, as described above, in one option not all ligands will be the same in the compositions comprising the Fe III complex compounds. For example, in the case that the preparation comprises FeTyr, then this may be formed by creating a complex from Fe III and a commercial source of tyrosine (Tyr), which may include low levels (typically, less than 10%, such as less than 5% or about 2.5%) of one or more further amino acids, such as cysteine (Cys) and/or phenylalanine (Phe), and so in one optional embodiment, when the compound is FeTyr, then some of the compounds in the composition may include one or more alternative amino acids (e.g. Cys and/or Phe) as ligands. The same applies mutatis mutandis to other ligands used in the preparation of Fe III complexes.

Therefore, for example, in a preparation comprising an Fe III complex as described above, it may be that less than 100% of the Fe III ligands are identical, although preferably at least 20%, 30%, 40%, 50%, 60%, 70%, 80%, 85%, 90%, 91%, 92%, 93%, 94%, 95%, 96%, 97%, 98%, or 99% of the ligands in the composition are identical. In that context, in one embodiment the term "identical" discriminates between enantiomeric forms of ligand, that is, different enantiomers are not identical; whereas, in another embodiment, the term "identical" can be applied to different enantiomeric forms of ligand, that is, optionally different enantiomeric forms of the same ligand are considered to be identical.

1. Derivatives

Preparations may optionally comprise derivatives of the above mentioned compounds. The term "derivative" does not mean that the derivative is synthesized from the parent compound either as a starting material or intermediate, although this may be the case. The term "derivative" can include salts (for example, pharmaceutically acceptable salts), prodrugs, or metabolites of the parent compound.

Derivatives include compounds in which free amino groups in the parent compound have been derivatized to form amine hydrochlorides, p-toluene sulfoamides, benzoxycarboamides, t-butyloxycarboamides, thiourethane-type derivatives, trifluoroacetylamides, chloroacetylamides, or formamides. Derivatives include compounds having one or more amino substituents or hydrogen groups replaced with substituted or unsubstituted alkyl, aminoalkyl, aryl, or heteroaryl groups having from 1 to 30 carbon atoms.

2. Salts

Preparations may optionally comprise the above-mentioned compounds in the form of a salt, for example, a pharmaceutically acceptable salt. Examples of pharmaceutically acceptable salts include, but are not limited to, mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids and inorganic or organic bases. Such conventional non-toxic salts include those derived from inorganic acids such as hydrochloric, hydrobromic, sulfuric, sulfamic, phosphoric, and nitric acids; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, tolunesulfonic, naphthalenesulfonic, methanesulfonic, ethane disulfonic, oxalic, and isethionic salts, and bases such as lithium hydroxide, sodium hydroxide, potassium hydroxide and ammonium hydroxide.

The pharmaceutically acceptable salts of the compounds can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 20th ed., Lippincott Williams & Wilkins, Baltimore, Md., 2000, p. 704; and "Handbook of Pharmaceutical Salts: Properties, Selection, and Use," P. Heinrich Stahl and Camille G. Wennuth, Eds., Wiley-VCH, Weinheim, 2002.

B. Antimicrobial Agents

Antimicrobial agents that may be used therapeutically and/or non-therapeutically with the preparations, for example for the treatment or prophylaxis of microbial infection, include, but are not limited to: (i) Aminoglycosides, including amikacin, gentamicin, kanamycin, neomycin, netilmicin, tobramycin, paromomycin, streptomycin, spectinomycin; (ii) Ansaycins, including geldanamycin, herbimycin, rifaximin, (iii) Carbacephem, including loracarbef, (iv) Carbapenems, including ertapenem, doripenem, imipenem/cilastatin, meropenem, (v) Cephalosporins, including cefadroxil, cefazolin, cefalotin or cefalothin, cephalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil, ceftobiprole, (vi) Glycopeptides, including teicoplanin, vancomycin, telavancin, dalbavancin, oritavancin, (vii) Lincosamides, including clindamycin, lincomycin, (viii) Lipopeptides including daptomycin, (ix) Macrolides including azithromycin, clarithromycin, dirithromycin, erythromycin, roxithromycin, troleandomycin, telithromycin, spiramyin, (x) Monobactams, including aztreonam, (xi) Nitrofurans, including furazolidone, nitrofurantoin, (xii) Oxazolidinones, including linezolid, posizolid, radezolid, torezolid, (xiii) Penicillins, including amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, temocillin, ticarcillin, amoxicillin/clavulanate, ampicillin/sulbactam, peperacillin/tazobactam, ticarcillin/clavulanate (xiv) Polypeptides including bacitracin, colistin, polymyxin B, (xv) Quinolones/Fluoroquinolone, including ciprofloxacin, enoxacin, gatifloxacin, gemifloxacin, levofloxacin, lomefloxacin, moxifloxacin, nalidixic acid, norfloxacin, ofloxacin, trovafloxacin, grepafloxacin, sparfloxacin, temafloxacin, (xvi) Sulfonamides, including mafenide, sulfacetamide, sulfadiazine, silver sulfadiazine, sulfadimethoxine, sulfamethizole, sulfamethoxazole, sulfanilamide, sulfasalazine, sulfisoxazole, trimethoprim-sulfamethoxazole (co-trimoxazaole), sulfonamidochrysoidine, (xvii) Tetracyclines, including demeclocycline, doxycycline, minocycline, oxytetracycline, tetracycline, (xviii) clofazimine, dapsone, capreomycin, cycloserine, ethambutol, ethionamide, isoniazid, pyrazinamide, rifampicin (rifampin), rifabutin, rifapentine, streptomycin, arsphenamine, chloramphenicol, fosfomycin, fusidic acid, metronidazole, mupirocin, platensimycin, quinupristirildalfopristin, thiamphenicol, tigecycline, tinidazole, and trimethoprim; and combinations thereof. The preparation may also be combined with triclosan and chlorhexidine. Other antimicrobial agents include: aztreonam; cefotetan and its disodium salt; loracarbef; cefoxitin and its sodium salt; cefazolin and its sodium salt; cefaclor; ceftibuten and its sodium salt; ceftizoxime; ceftizoxime sodium salt; cefoperazone and its sodium salt; cefuroxime and its sodium salt; cefuroxime axetil; cefprozil; ceftazidime; cefotaxime and its sodium salt; cefadroxil; ceftazidime and its sodium salt; cephalexin; cefamandole nafate; cefepime and its hydrochloride, sulfate, and phosphate salt; cefdinir and its sodium salt; ceftriaxone and its sodium salt; cefixime and its sodium salt; cefpodoxime proxetil; meropenem and its sodium salt; imipenem and its sodium salt; cilastatin and its sodium salt; azithromycin; clarithromycin; dirithromycin; erythromycin and hydrochloride, sulfate, or phosphate salts, ethylsuccinate, and stearate forms thereof clindamycin; clindamycin hydrochloride, sulfate, or phosphate salt; lincomycin and hydrochloride, sulfate, or phosphate salt thereof, tobramycin and its hydrochloride, sulfate, or phosphate salt; streptomycin and its hydrochloride, sulfate, or phosphate salt; neomycin and its hydrochloride, sulfate, or phosphate salt; acetyl sulfisoxazole; colistimethate and its sodium salt; quinupristin; dalfopristin; amoxicillin; ampicillin and its sodium salt; clavulanic acid and its sodium or potassium salt; penicillin G; penicillin G benzathine, or procaine salt; penicillin G sodium or potassium salt; carbenicillin and its disodium or indanyl disodium salt; piperacillin and its sodium salt; ticarcillin and its disodium salt; sulbactam and its sodium salt; moxifloxacin; ciprofloxacin; ofloxacin; levofloxacins; norfloxacin; gatifloxacin; trovafloxacin mesylate; alatrofloxacin mesylate; trimethoprim; sulfamethoxazole; demeclocycline and its hydrochloride, sulfate, or phosphate salt; doxycycline and its hydrochloride, sulfate, or phosphate salt; oxytetracycline and its hydrochloride, sulfate, or phosphate salt; chlortetracycline and its hydrochloride, sulfate, or phosphate salt; metronidazole; dapsone; atovaquone; rifabutin; linezolide; polymyxin B and its hydrochloride, sulfate, or phosphate salt; sulfacetamide and its sodium salt; clarithromycin; and silver ions, salts, and complexes.

A complex of L-tyrosine with Fe III (Fe-Tyr)can be combined with any one or more of the foregoing antibiotics, either formulated together in the same composition for administration or presented in separate compositions for use separately, simultaneously or sequentially.

C. Excipients and Carriers

The preparations as defined above can be formulated for use in accordance with any aspect and may, for example, be formulated in a way that is suitable for enteral, parenteral, topical, or pulmonary administration.

The preparations can be combined with one or more pharmaceutically acceptable carriers and/or excipients that are considered safe and effective and may be administered to an individual without causing undesirable biological side effects or unwanted interactions.

The carrier can include all components present in the pharmaceutical formulation other than the active ingredient or ingredients. The preparations are included in the formulation in an effective amount to achieve the effect of the aspects of the present invention, for example in an amount that is effective to inhibit biofilm formation or reduce biofilm buildup. An effective amount of a preparations provided to a subject may be an amount that is enough to provide the required degree of reduction of microbial colonization. This may depend on the type of preparation and/or the size of the animal.

In one embodiment an effective amount of the preparations may be an amount that is effective to deliver the preparations to the site at which action is required with an Fe (III) concentration that ranges from 1 µm to 1 M, preferably greater than 10 µM, 20 µM, 30 µM, 40 µM, 50 µM, 60 µM, 70 µM, 80 µM, 90 µM, 100 µM, 110 µM, 120 µM, 130 µM, 140 µM, 150 µM, 160 µM, 170 µM, 180 µM, 190 µM, 200 µM, 300 µM, 400 µM, 500 µM, 600 µM, 700 µM, 800 µM, 900 µM, 1 mM, 10 mM, 50 mM, 100 mM, 500 mM, 900 mM or more. A suitable Fe (III) concentration may be within the range of about 1 µm to about 1 mM, or about 30 µM to about 0.5 mM, or about 60 µM to about 0.3 mM. These concentrations may particularly apply to the performance of the invention in the context of the aspects of the present invention.

In a further embodiment an effective amount of the preparation may be 0.3 to 32 mg/day/kg bodyweight of the subject such as a chicken. In another embodiment an effective concentration of the preparations may be an amount effective to provide an Fe (III) concentration between 0.001 to 1 mM for use in coatings or devices, or solutions.

The preparations can also be formulated for use as a disinfectant, for example, in a hospital environment or for industrial application.

1. Parenteral Formulations

The preparationsfor use in accordance with any of the aspects and may be formulated for parenteral administration.

Parenteral administration may include administration to a patient intravenously, intradermally, intraarterially, intraperitoneally, intralesionally, intracranially, intraarticularly, intraprostatically, intrapleurally, intratracheally, intravitreally, intratumorally, intramuscularly, subcutaneously, subconjunctivally, intravesicularly, intrapericardially, intraumbilically, by injection, and by infusion.

Parenteral formulations can be prepared as aqueous compositions using techniques known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the active compounds as the free acid or base or pharmacologically acceptable salts thereof can be prepared in water or another solvent or dispersing medium suitably mixed with one or more pharmaceutically acceptable excipients including, but not limited to, surfactants, dispersants, emulsifiers, pH modifying agents, viscosity modifying agents, and combination thereof Suitable surfactants may be anionic, cationic, amphoteric or nonionic surface-active agents. Suitable anionic surfactants include, but are not limited to, those containing carboxylate, sulfonate and sulfate ions. Examples of anionic surfactants include sodium, potassium, ammonium ions of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 mono laurate, polyoxyethylene monolaurate, polysorbates, polyoxyethylene octylphenylether, PEG-1000 cetyl ether, polyoxyethylene tridecyl ether, polypropylene glycol butyl ether, Poloxamer® (triblock copolymer of polyoxyethylene, followed by a block of polyoxypropylene, followed by a block of polyoxyethylene) 401, stearoyl monoisopropanolamide, and polyoxyethylene hydrogenated tallow amide. Examples of amphoteric surfactants include sodium N-dodecyl-.beta.-alanine, sodium N-lauryl-β-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

The formulation is typically buffered to a pH of 3-8 for parenteral administration upon reconstitution. Suitable buffers include, but are not limited to, phosphate buffers, acetate buffers, and citrate buffers. Where preparations comprise acidic compounds, they may be advantageously formulated with a buffer in order to achieve a suitable pH, particularly in the context of preparing injectable formulation, including formulations for intravenous injection.

Water-soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the active compounds in the required amount in the appropriate solvent or dispersion medium with one or more of the excipients listed above, as required, followed by filtered sterilization. Generally, dispersions are prepared by incorporating the various sterilized active ingredients into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof The powders can be prepared in such a manner that the particles are porous in nature, which can increase dissolution of the particles. Methods for making porous particles are well known in the art.

(a) Controlled Release Formulations

The parenteral formulations described herein comprising one or more preparationsfor use in accordance with any of the aspects may be formulated for controlled release including immediate release, delayed release, extended release, pulsatile release, and combinations thereof.

1. Nano- and microparticles

For parenteral administration, the one or more preparationsfor use in accordance with any of the aspects of the present invention, and optional one or more additional active agents, can be incorporated into microparticles, nanoparticles, or combinations thereof that provide controlled release of the one of more preparations, or one or more components thereof, and/or one or more additional active agents. In embodiments wherein the formulations contains two or more active components, such as drugs, then they can be formulated for the same type of controlled release (e.g., delayed, extended, immediate, or pulsatile) or they can be independently formulated for different types of release (e.g., immediate and delayed, immediate and extended, delayed and extended, delayed and pulsatile, etc.).

For example, the one or more preparations and/or one or more additional active agents can be incorporated into polymeric microparticles, which provide controlled release of the active agent(s). Release of the active agent (s) is controlled by diffusion of the drug(s) out of the microparticles and/or degradation of the polymeric particles by hydrolysis and/or enzymatic degradation. Suitable polymers include ethylcellulose and other natural or synthetic cellulose derivatives.

Polymers, which are slowly soluble and form a gel in an aqueous environment, such as hydroxypropyl methylcellulose or polyethylene oxide, can also be suitable as materials for drug containing microparticles. Other polymers include, but are not limited to, polyanhydrides, poly(ester anhydrides), polyesters, such as polylactide (PLA), polyglycolide (PGA), poly(lactide-co-glycolide) (PLGA), polydioxanone, poly-3-hydroxybutyrate (PHB) and copolymers thereof, poly-4-hydroxybutyrate (P4HB) and copolymers thereof, polycaprolactone and copolymers thereof, polymers including, but not limited to, polymers of glycolic acid, lactic acid, 1,4-dioxanone, trimethylene carbonate, 3-hydroxybutyric acid, 4-hydroxybutyrate, e-caprolactone, including polyglycolic acid, polylactic acid, polydioxanone, polycaprolactone, copolymers of glycolic and lactic acids, such as VICRYL® polymer, MAXON® and MONOCRYL® polymers, and including poly(lactide-co-caprolactones); poly (orthoesters); polyanhydrides; poly(phosphazenes); polyhydroxyalkanoates; synthetically or biologically prepared polyesters; polycarbonates; tyrosine polycarbonates; polyamides (including synthetic and natural polyamides, polypeptides, and poly(amino acids)); polyesteramides; poly (alkylene alkylates); polyethers (such as polyethylene glycol, PEG, and polyethylene oxide, PEO); polyvinyl pyrrolidones or PVP; polyurethanes; polyetheresters; polyacetals; polycyanoacrylates; poly(oxyethylene)/poly(oxypropylene) copolymers; polyacetals, polyketals; polyphosphates; (phosphorous-containing) polymers; polyphosphoesters; polyalkylene oxalates; polyalkylene succinates; poly(maleic acids); silk (including recombinant silks and silk derivatives and analogs); chitin; chitosan; modified chitosan; biocompatible polysaccharides; hydrophilic or water soluble polymers, such as polyethylene glycol, (PEG) or polyvinyl pyrrolidone (PVP), with blocks of other biocompatible or biodegradable polymers, for example, poly (lactide), poly(lactide-co-glycolide, or polycaprolcatone and copolymers thereof, including random copolymers and block copolymers thereof. and combinations thereof.

Alternatively, the active agent can be incorporated into microparticles prepared from materials which are insoluble in aqueous solution or slowly soluble in aqueous solution, but are capable of degrading within the GI tract by means including enzymatic degradation, surfactant action of bile acids, and/or mechanical erosion. As used herein, the term "slowly soluble in water" refers to materials that are not dissolved in water within a period of 30 minutes. Preferred examples include fats, fatty substances, waxes, wax-like substances and mixtures thereof. Suitable fats and fatty substances include fatty alcohols (such as lauryl, myristyl stearyl, cetyl or cetostearyl alcohol), fatty acids and derivatives, including but not limited to fatty acid esters, fatty acid glycerides (mono-, di- and tri-glycerides), and hydrogenated fats. Specific examples include, but are not limited to hydrogenated vegetable oil, hydrogenated cottonseed oil, hydrogenated castor oil, hydrogenated oils available under the trade name STEROTEX®, stearic acid, cocoa butter, and stearyl alcohol. Suitable waxes and wax-like materials include natural or synthetic waxes, hydrocarbons, and normal waxes. Specific examples of waxes include beeswax, glycowax, castor wax, carnauba wax, paraffins and candelilla wax. As used herein, a wax-like material is defined as any material, which is noimally solid at room temperature and has a melting point of from about 30 to 300° C.

In some cases, it may be desirable to alter the rate of water penetration into the microparticles. To this end, rate-controlling (wicking) agents can be formulated along with the fats or waxes listed above. Examples of rate-controlling materials include certain starch derivatives (e.g., waxy maltodextrin and drum dried corn starch), cellulose derivatives (e.g., hydroxypropylmethyl-cellulose, hydroxypropyl-cellulose, methylcellulose, and carboxymethyl-cellulose), alginic acid, lactose and talc. Additionally, a pharmaceutically acceptable surfactant (for example, lecithin) may be added to facilitate the degradation of such microparticles.

Proteins, which are water insoluble, such as zein, can also be used as materials for the formation of active agent containing microparticles. Additionally, proteins, polysaccharides and combinations thereof, which are water-soluble, can be formulated with drug into microparticles and subsequently cross-linked to form an insoluble network. For example, cyclodextrins can be complexed with individual drug molecules and subsequently cross-linked.

2. Method of Making Nano- and Microparticles

Encapsulation or incorporation of active agent, such as the one or more preparationsfor use in accordance with any of the aspects of the present invention, into carrier materials to produce drug-containing microparticles can be achieved through known pharmaceutical formulation techniques. In the case of formulation in fats, waxes or wax-like materials, the carrier material is typically heated above its melting temperature and the active agent is added to form a mixture comprising active agent particles suspended in the carrier material, active agent dissolved in the carrier material, or a mixture thereof Microparticles can be subsequently formulated through several methods including, but not limited to, the processes of congealing, extrusion, spray chilling or aqueous dispersion. In a preferred process, wax is heated above its melting temperature, active agent is added, and the molten wax-drug mixture is congealed under constant stirring as the mixture cools. Alternatively, the molten wax-drug mixture can be extruded and spheronized to form pellets or beads. These processes are known in the art.

For some carrier materials it may be desirable to use a solvent evaporation technique to produce active agent-containing microparticles. In this case active agent and carrier material are co-dissolved in a mutual solvent and microparticles can subsequently be produced by several techniques including, but not limited to, forming an emulsion in water or other appropriate media, spray drying or by evaporating off the solvent from the bulk solution and milling the resulting material.

In some embodiments, active agent in a particulate form is homogeneously dispersed in a water-insoluble or slowly water soluble material. To minimize the size of the active agent particles within the composition, the active agent powder itself may be milled to generate fine particles prior to formulation. The process of jet milling, known in the pharmaceutical art, can be used for this purpose. In some embodiments active agent in a particulate form is homogeneously dispersed in a wax or wax like substance by heating the wax or wax like substance above its melting point and adding the active agent particles while stirring the mixture. In this case a pharmaceutically acceptable surfactant may be added to the mixture to facilitate the dispersion of the active agent particles.

The particles can also be coated with one or more modified release coatings. Solid esters of fatty acids, which are hydrolyzed by lipases, can be spray coated onto microparticles or active agent particles. Zein is an example of a naturally water-insoluble protein. It can be coated onto active agent containing microparticles or active agent particles by spray coating or by wet granulation techniques. In addition to naturally water-insoluble materials, some substrates of digestive enzymes can be treated with cross-linking procedures, resulting in the formation of non-soluble networks. Many methods of cross-linking proteins, initiated by both chemical and physical means, have been reported. One of the most common methods to obtain cross-linking is the use of chemical cross-linking agents. Examples of chemical cross-linking agents include aldehydes (gluteraldehyde and formaldehyde), epoxy compounds, carbodiimides, and genipin. In addition to these cross-linking agents, oxidized and native sugars have been used to cross-link gelatin. Cross-linking can also be accomplished using enzymatic means; for example, transglutaminase has been approved as a GRAS substance for cross-linking seafood products. Finally, cross-linking can be initiated by physical means such as thermal treatment, UV irradiation and gamma irradiation.

To produce a coating layer of cross-linked protein surrounding active agent containing microparticles or active agent particles, a water-soluble protein can be spray coated onto the microparticles and subsequently cross-linked by the one of the methods described above. Alternatively, active agent-containing microparticles can be microencapsulated within protein by coacervation-phase separation (for example, by the addition of salts) and subsequently cross-linked. Some suitable proteins for this purpose include gelatin, albumin, casein, and gluten.

Polysaccharides can also be cross-linked to form a water-insoluble network. For many polysaccharides, this can be accomplished by reaction with calcium salts or multivalent cations, which cross-link the main polymer chains. Pectin, alginate, dextran, amylose and guar gum are subject to cross-linking in the presence of multivalent cations. Complexes between oppositely charged polysaccharides can also be formed; pectin and chitosan, for example, can be complexed via electrostatic interactions.

(b) Injectable/Implantable Formulations

The one or more preparationsfor use in accordance with any of the aspects can be incorporated into injectable/implantable solid or semi-solid implants, such as polymeric implants. In one embodiment, the one or more preparations are incorporated into a polymer that is a liquid or paste at room temperature, but upon contact with aqueous medium, such as physiological fluids, exhibits an increase in viscosity to form a semi-solid or solid material. Exemplary polymers include, but are not limited to, hydroxyalkanoic acid polyesters derived from the copolymerization of at least one unsaturated hydroxy fatty acid copolymerized with hydroxyalkanoic acids. The polymer can be melted, mixed with the active substance and cast or injection molded into a device. Such melt fabrication require polymers having a melting point that is below the temperature at which the substance to be delivered and polymer degrade or become reactive. The device can also be prepared by solvent casting where the polymer is dissolved in a solvent and the drug dissolved or dispersed in the polymer solution and the solvent is then evaporated. Solvent processes require that the polymer be soluble in organic solvents. Another method is compression molding of a mixed powder of the polymer and the drug or polymer particles loaded with the active agent.

Alternatively, the one or more preparations can be incorporated into a polymer matrix and molded, compressed, or extruded into a device that is a solid at room temperature. For example, the preparations can be incorporated into a biodegradable polymer, such as polyanhydrides, polyhydroalkanoic acids (PHAs), PLA, PGA, PLGA, polycaprolactone, polyesters, polyamides, polyorthoesters, polyphosphazenes, proteins and polysaccharides such as collagen, hyaluronic acid, albumin and gelatin, and combinations thereof and compressed into solid device, such as disks, or extruded into a device, such as rods. Further alternative polymers for use in this context include polymers include, but are not limited to, polymers of glycolic acid, lactic acid, 1,4-dioxanone, trimethylene carbonate, 3-hydroxybutyric acid, 4-hydroxybutyrate, e-caprolactone, including polyglycolic acid, polylactic acid, polydioxanone, polycaprolactone, copolymers of glycolic and lactic acids, such as VICRYL® polymer, MAXON® and MONOCRYL® polymers, and including poly(lactide-co-caprolactones); poly (orthoesters); polyanhydrides; poly(phosphazenes); polyhydroxyalkanoates; synthetically or biologically prepared polyesters; polycarbonates; tyrosine polycarbonates; polyamides (including synthetic and natural polyamides, polypeptides, and poly(amino acids)); polyesteramides; poly (alkylene alkylates); polyethers (such as polyethylene glycol, PEG, and polyethylene oxide, PEO); polyvinyl pyrrolidones or PVP; polyurethanes; polyetheresters; polyacetals; polycyanoacrylates; poly(oxyethylene)/poly(oxypropylene) copolymers; polyacetals, polyketals;

polyphosphates; (phosphorous-containing) polymers; polyphosphoesters; polyalkylene oxalates; polyalkylene succinates; poly(maleic acids); silk (including recombinant silks and silk derivatives and analogs); chitin; chitosan; modified chitosan; biocompatible polysaccharides; hydrophilic or water soluble polymers, such as polyethylene glycol, (PEG) or polyvinyl pyrrolidone (PVP), with blocks of other biocompatible or biodegradable polymers, for example, poly (lactide), poly(lactide-co-glycolide, or polycaprolcatone and copolymers thereof, including random copolymers and block copolymers thereof.

The release of the one or more preparations, or one or more components thereof, from the implant can be varied by selection of the polymer, the molecular weight of the polymer, and/or modification of the polymer to increase degradation, such as the formation of pores and/or incorporation of hydrolyzable linkages. Methods for modifying the properties of biodegradable polymers to vary the release profile of the preparations, or one or more components thereof, from the implant are well known in the art.

2. Enteral Formulations

The preparationsfor use in accordance with any of the aspects may be formulated for enteral administration.

Suitable oral dosage forms include tablets, capsules, solutions, suspensions, syrups, and lozenges. Tablets can be made using compression or molding techniques well known in the art. Gelatin or non-gelatin capsules can be prepared as hard or soft capsule shells, which can encapsulate liquid, solid, and semi-solid fill materials, using techniques well known in the art.

Formulations may be prepared using a pharmaceutically acceptable carrier. As generally used herein "carrier" includes, but is not limited to, diluents, preservatives, binders, lubricants, disintegrators, swelling agents, fillers, stabilizers, and combinations thereof.

Carrier also includes all components of the coating composition, which may include plasticizers, pigments, colorants, stabilizing agents, and glidants.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

"Diluents", also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

"Binders" are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

"Lubricants" are used to facilitate tablet manufacture. Examples of suitable lubricants include, but are not limited to, magnesium stearate, calcium stearate, stearic acid, glycerol behenate, polyethylene glycol, talc, and mineral oil.

"Disintegrants" are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (POLYPLASDONE® XL from GAF Chemical Corp).

"Stabilizers" are used to inhibit or retard drug decomposition reactions, which include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

(a) Controlled Release Enteral Formulations

Oral dosage forms, such as capsules, tablets, solutions, and suspensions, can be formulated for controlled release, for example, for the controlled release of the one or more preparationsfor use in accordance with any of the aspects of the present invention. For example, the one or more preparations and optional one or more additional active agents can be formulated into nanoparticles, microparticles, and combinations thereof, and encapsulated in a soft or hard gelatin or non-gelatin capsule or dispersed in a dispersing medium to form an oral suspension or syrup. The particles can be formed of the active agent and a controlled release polymer or matrix. Alternatively, the active agent particles can be coated with one or more controlled release coatings prior to incorporation in to the finished dosage form.

In another embodiment, the one or more preparations and optional one or more additional active agents are dispersed in a matrix material, which gels or emulsifies upon contact with an aqueous medium, such as physiological fluids. In the case of gels, the matrix swells entrapping the active agents, which are released slowly over time by diffusion and/or degradation of the matrix material. Such matrices can be formulated as tablets or as fill materials for hard and soft capsules.

In still another embodiment, the one or more preparations, and optional one or more additional active agents are formulated into a sold oral dosage form, such as a tablet or capsule, and the solid dosage form is coated with one or more controlled release coatings, such as a delayed release coatings or extended release coatings. The coating or coatings may also contain the one or more preparations and/or additional active agents.

(1) Extended Release Dosage Forms

The extended release formulations are generally prepared as diffusion or osmotic systems, which are known in the art. A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkylcelluloses such as hydroxypropyl-cellulose, hydroxypropylmethylcellulose, sodium carboxymethylcellulose, and CARBOPOL® 934 (cross-linked polyacrylate polymer), polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain preferred embodiments, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamine copolymer poly(methyl methacrylate), poly(methacrylic acid)(anhydride), polymethacrylate, polyacrylamide, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In one preferred embodiment, the acrylic polymer is an acrylic resin lacquer such as that which is commercially available from Rohm Pharma under the tradename EUDRAGIT®. In further preferred embodiments, the acrylic polymer comprises a mixture of two acrylic resin lacquers commercially available from Rohm Phauna under the trade names EUDRAGIT® RL30D and EUDRAGIT® RS30D, respectively. EUDRAGIT® RL30D and EUDRAGIT® RS30D are copolymers of acrylic and methacrylic esters with a low content of quaternary ammonium groups, the molar ratio of ammonium groups to the remaining neutral (meth)acrylic esters being 1:20 in EUDRAGIT® RL30D and 1:40 in EUDRAGIT® RS30D. The mean molecular weight is about 150,000. EUDRAGIT® S-100 and EUDRAGIT® L-100 are also preferred. The code designations RL (high permeability) and RS (low permeability) refer to the permeability properties of these agents. EUDRAGIT® RL/RS mixtures are insoluble in water and in digestive fluids. However, multiparticulate systems formed to include the same are swellable and permeable in aqueous solutions and digestive fluids.

The polymers described above such as EUDRAGIT® RL/RS may be mixed together in any desired ratio in order to ultimately obtain a sustained-release formulation having a desirable dissolution profile. Desirable sustained-release multiparticulate systems may be obtained, for instance, from 100% EUDRAGIT® RL, 50% EUDRAGIT® RL and 50% EUDRAGIT t® RS, and 10% EUDRAGIT® RL and 90% EUDRAGIT® RS. One skilled in the art will recognize that other acrylic polymers may also be used, such as, for example, EUDRAGIT® L.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above can be combined in a final dosage form comprising single or multiple units. Examples of multiple units include, but are not limited to, multilayer tablets and capsules containing tablets, beads, or granules. An immediate release portion can be added to the extended release system by means of either applying an immediate release layer on top of the extended release core using a coating or compression process or in a multiple unit system such as a capsule containing extended and immediate release beads.

Extended release tablets containing hydrophilic polymers are prepared by techniques commonly known in the art such as direct compression, wet granulation, or dry granulation. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In the congealing method, the drug is mixed with a wax material and either spray-congealed or congealed and screened and processed.

(2) Delayed Release Dosage Forms

Delayed release formulations can be created by coating a solid dosage form with a polymer film, which is insoluble in the acidic environment of the stomach, and soluble in the neutral environment of the small intestine.

The delayed release dosage units can be prepared, for example, by coating an active agent or an active agent-containing composition with a selected coating material. The active agent-containing composition may be, e.g., a tablet for incorporation into a capsule, a tablet for use as an inner core in a "coated core" dosage form, or a plurality of active agent-containing beads, particles or granules, for incorporation into either a tablet or capsule.

Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename EUDRAGIT® (Rohm Phatma; Westerstadt, Germany), including EUDRAGIT® L30D-55 and L100-55 (soluble at pH 5.5 and above), EUDRAGIT® L-100 (soluble at pH 6.0 and above), EUDRAGIT® S (soluble at pH 7.0 and above, as a result of a higher degree of esterification), and EUDRAGITS® NE, RL and RS (water-insoluble polymers having different degrees of pettneability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating, and will generally represent about 3 wt. % to 50 wt. %", or 10 wt % to 50 wt. %, relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

3. Topical Formulations

The preparationsfor use in accordance with any of the aspects and may be formulated for topical administration.

The formulations may contain the one or more preparations discussed above, alone or in combination, in an effective amount to prevent or inhibit biofilm formation on a surface, or reduce the amount of biofilm on a surface being treated. 1000 colony forming units (cfu) of *Campylobacter* are enough to infect a human and cause disease in a human.

Therefore, in one embodiment, an effective amount of the one or more preparations as defined.A of this application is, or are, enough of the preparation(s), alone, or in combination with other compounds, to reduce the number of cfu of *Campylobacter* or other microorganism of interest on the surface being treated to a number that is unlikely to, or which will not, cause infection in humans.

Suitable dosage forms for topical administration include creams, ointments, salves, sprays, gels, lotions, irrigants, and emulsions.

"Buffers" are used to control pH of a composition. Preferably, the buffers buffer the composition from a pH of about 4 to a pH of about 7.5, more preferably from a pH of about 4 to a pH of about 7, and most preferably from a pH of about 5 to a pH of about 7. In a preferred embodiment, the buffer is triethanolamine.

"Emollients" are an externally applied agent that softens or soothes skin and are generally known in the art and listed in compendia, such as the "Handbook of Pharmaceutical Excipients", 4$^{th}$ Ed., Pharmaceutical Press, 2003. These include, without limitation, almond oil, castor oil, ceratonia extract, cetostearoyl alcohol, cetyl alcohol, cetyl esters wax, cholesterol, cottonseed oil, cyclomethicone, ethylene glycol palmitostearate, glycerin, glycerin monostearate, glyceryl monooleate, isopropyl myristate, isopropyl palmitate, lanolin, lecithin, light mineral oil, medium-chain triglycerides, mineral oil and lanolin alcohols, petrolatum, petrolatum and lanolin alcohols, soybean oil, starch, stearyl alcohol, sunflower oil, xylitol and combinations thereof. In one embodiment, the emollients are ethylhexylstearate and ethylhexyl palmitate.

"Emulsifiers" are surface active substances which promote the suspension of one liquid in another and promote the formation of a stable mixture, or emulsion, of oil and water. Common emulsifiers are: metallic soaps, certain animal and vegetable oils, and various polar compounds. Suitable emulsifiers include acacia, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxpropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In one embodiment, the emulsifier is glycerol stearate.

"Penetration enhancers" are known in the art and include, but are not limited to, fatty alcohols, fatty acid esters, fatty acids, fatty alcohol ethers, amino acids, phospholipids, lecithins, cholate salts, enzymes, amines and amides, complexing agents (liposomes, cyclodextrins, modified celluloses, and diimides), macrocyclics, such as macrocylic lactones, ketones, and anhydrides and cyclic ureas, surfactants, N-methyl pyrrolidones and derivatives thereof, DMSO and related compounds, ionic compounds, azone and related compounds, and solvents, such as alcohols, ketones, amides, polyols (e.g., glycols). Examples of these classes are known in the art.

"Preservatives" can be used to prevent the growth of fungi and microorganisms. Suitable antifungal and antimicrobial agents include, but are not limited to, benzoic acid, butylparaben, ethyl paraben, methyl paraben, propylparaben, sodium benzoate, sodium propionate, benzalkonium chloride, benzethonium chloride, benzyl alcohol, cetylpyridinium chloride, chlorobutanol, phenol, phenylethyl alcohol, and thimerosal.

"Surfactants" are surface-active agents that lower surface tension and thereby increase the emulsifying, foaming, dispersing, spreading and wetting properties of a product. Suitable non-ionic surfactants include emulsifying wax, glyceryl monooleate, polyoxyethylene alkyl ethers, polyoxyethylene castor oil derivatives, polysorbate, sorbitan esters, benzyl alcohol, benzyl benzoate, cyclodextrins, glycerin monostearate, poloxamer, povidone and combinations thereof. In one embodiment, the non-ionic surfactant is stearyl alcohol.

(a) Emulsions

An emulsion is a preparation of one liquid distributed in small globules throughout the body of a second liquid. In particular embodiments, the non-miscible components of the emulsion include a lipophilic component and an aqueous component. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

The oil phase may consist at least in part of a propellant, such as an HFA propellant. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

A sub-set of emulsions are the self-emulsifying systems. These delivery systems are typically capsules (hard shell or soft shell) comprised of the preparation dispersed or dissolved in a mixture of surfactant(s) and lipophilic liquids such as oils or other water immiscible liquids. When the capsule is exposed to an aqueous environment and the outer gelatin shell dissolves, contact between the aqueous medium and the capsule contents instantly generates very small emulsion droplets. These typically are in the size range of micelles or nanoparticles. No mixing force is required to generate the emulsion as is typically the case in emulsion formulation processes.

(b) Lotions

A lotion can contain finely powdered substances that are insoluble in the dispersion medium through the use of suspending agents and dispersing agents. Alternatively, lotions can have as the dispersed phase liquid substances that are immiscible with the vehicle and are usually dispersed by means of emulsifying agents or other suitable stabilizers. In one embodiment, the lotion is in the form of an emulsion having a viscosity of between 100 and 1000 centistokes. The fluidity of lotions permits rapid and uniform application over a wide surface area. Lotions are typically intended to dry on the skin leaving a thin coat of their medicinal components on the skin's surface.

(c) Creams

Creams may contain emulsifying agents and/or other stabilizing agents. In one embodiment, the formulation is in the form of a cream having a viscosity of greater than 1000 centistokes, typically in the range of 20,000-50,000 centistokes. Creams are often time preferred over ointments, as they are generally easier to spread and easier to remove.

The difference between a cream and a lotion is the viscosity, which is dependent on the amount/use of various oils and the percentage of water used to prepare the formulations. Creams are typically thicker than lotions, may have various uses and often one uses more varied oils/butters, depending upon the desired effect upon the skin. In a cream formulation, the water-base percentage is about 60-75% and the oil-base is about 20-30% of the total, with the other percentages being the emulsifier agent, preservatives and additives for a total of 100%.

(d) Ointments

Examples of suitable ointment bases include hydrocarbon bases (e.g., petrolatum, white petrolatum, yellow ointment, and mineral oil); absorption bases (hydrophilic petrolatum, anhydrous lanolin, lanolin, and cold cream); water-removable bases (e.g., hydrophilic ointment), and water-soluble bases (e.g., polyethylene glycol ointments). Pastes typically differ from ointments in that they contain a larger percentage of solids. Pastes are typically more absorptive and less greasy than ointments prepared with the same components.

(e) Gels

Gels are semisolid systems containing dispersions of small or large molecules in a liquid vehicle that is rendered semisolid by the action of a thickening agent or polymeric material dissolved or suspended in the liquid vehicle. The liquid may include a lipophilic component, an aqueous component or both. Some emulsions may be gels or otherwise include a gel component. Some gels, however, are not emulsions because they do not contain a homogenized blend of immiscible components. Suitable gelling agents include, but are not limited to, modified celluloses, such as hydroxypropyl cellulose and hydroxyethyl cellulose; Carbopol homopolymers and copolymers; and combinations thereof. Suitable solvents in the liquid vehicle include, but are not limited to, diglycol monoethyl ether; alkylene glycols, such as propylene glycol; dimethyl isosorbide; alcohols, such as isopropyl alcohol and ethanol. The solvents are typically selected for their ability to dissolve the preparation, or one or more components thereof. Other additives, which improve the skin feel and/or emolliency of the formulation, may also be incorporated. Examples of such additives include, but are not limited to, isopropyl myristate, ethyl acetate, $C_{12}$-$C_{15}$ alkyl benzoates, mineral oil, squalane, cyclomethicone, capric/caprylic triglycerides, and combinations thereof.

Foams

Foams consist of an emulsion in combination with a gaseous propellant. The gaseous propellant consists primarily of hydrofluoroalkanes (HFAs). Suitable propellants include HFAs such as 1,1,1,2-tetrafluoroethane (HFA 134a) and 1,1,1,2,3,3,3-heptafluoropropane (HFA 227), but mixtures and admixtures of these and other HFAs that are currently approved or may become approved for medical use are suitable. The propellants preferably are not hydrocarbon propellant gases, which can produce flammable or explosive vapors during spraying. Furthermore, the compositions preferably contain no volatile alcohols, which can produce flammable or explosive vapors during use.

4. Disinfecting and Cleaning Formulations

The preparations for use in accordance with any of the aspects may be formulated into cleaning formulations.

The cleaning formulations include formulations that are highly efficacious for household cleaning applications (e.g., hard surfaces like floors, countertops, tubs, tile, dishes and softer cloth materials like clothing, sponges, paper towels, etc.), personal care applications (e.g. lotions, shower gels, soaps, shampoos, sprays, wipes, toothpaste, acne treatments, skin cleansers, mouthwash, wound irrigation solutions, towelettes, contact lenses and lens cases) and industrial and hospital applications (e.g., antifouling coatings, and disinfection of instruments, medical devices, gloves, filters, membranes, tubing, drains, pipes including gas pipes, oil pipes, drilling pipes, fracking pipes, sewage pipes, drainage pipes, hoses, animal carcasses, fish tanks, showers, children's toys, boat hulls, and cooling towers). These formulations are efficacious for cleaning surfaces which are infected or contaminated with biofilm or for preventing the formation of biofilm on these surfaces.

The preparations can be formulated into a solution in a suitable solvent for administration in a spray bottle, the preparations can be formulated as an aerosol, as a foam, suitable for spraying onto surfaces, or, they can be imbibed into a cloth or other item suitable for wiping down a surface to be disinfected. Methods for making formulations for use as a disinfectant in the forms are known in the art.

One embodiment provides the preparations in a composition containing a pH dye indicator and an alkaline substance. The pH indicator dye indicates what surface has been disinfected and ensures that a sufficient time has passed to disinfect the surface. See for example, U.S. Publication No. 20140057987, which is incorporated by reference in its entirety.

Cleaning formulations can include one or more of the preparations and an acceptable carrier. The carrier can be in a wide variety of forms. For example, the carrier may be an aqueous-based solution or cleanser, an alcohol-based solution or gel or an emulsion carrier, including, but not limited to, oil-in-water, water-in-oil, water-in-oil-in-water, and oil-in-water-in-silicone emulsions. The carrier solution containing the preparation(s) can be applied directly to the surface to be treated or delivered via a suitable substrate.

The cleaning formulations can be formulated for use on the skin. In these embodiments the one or more preparations can be formulated in a dermatologically acceptable carrier. The dermatologically acceptable carriers can also be, for example, formulated as alcohol or water based hand cleansers, toilet bars, liquid soaps, shampoos, bath gels, hair conditioners, hair tonics, pastes, or mousses.

Cleaning formulations can contain one or more surfactants. The surfactant is suitably selected from anionic, nonionic, zwitterionic, amphoteric and ampholytic surfactants, as well as mixtures of these surfactants. Such surfactants are well known to those skilled in the detergency art. Non limiting examples of possible surfactants include isoceteth-20, sodium methyl cocoyl taurate, sodium methyl oleoyl taurate, and sodium lauryl sulfate. Examples of a broad variety of additional surfactants are described in McCutcheon's Detergents and Emulsifiers. North American Edition (1986), published by Allured Publishing Corporation. The cleansing formulations can optionally contain, at their art-established levels, other materials which are conventionally used in cleansing formulations.

Additional carriers suitable for the cleaning formulations may include various substrate-based products. In such instances, the present formulations may be impregnated into or onto the substrate products and may be allowed to remain wet or may be subjected to a drying process. For instance, suitable carriers include, but are not limited to, dry and wet wipes suitable for personal care and household use (e.g., nonwoven baby wipes, household cleaning wipes, surgical preparation wipes, etc.); diapers; infant changing pads; dental floss; personal care and household care sponges or woven cloths (e.g., washcloths, towels, etc.); tissue-type products (e.g. facial tissue, paper towels, etc.); and disposable garments (e.g., gloves, smocks, surgical masks, infant bibs, socks, shoe inserts, etc.). Cleaning formulations can be incorporated into various household care products including, but not limited to, hard surface cleaners (e.g., disinfectant sprays, liquids, or powders); dish or laundry detergents (liquid or solid), floor waxes, glass cleaners, etc.

Exemplary carriers can include aqueous solutions, e.g. having from about 0% to about 98.8%, by weight of the composition, of water. Additionally, carriers may contain an aqueous alcohol solution. The amount of alcohol present in the alcohol solution will vary depending on the type of product in which the composition is incorporated, i.e. say a wipe where the preferred amount of alcohol present would be from about 0% to about 25% whereas a hand sanitizer preferably contains from about 60% to about 95%, of alcohol. Therefore, suitable deimatologically acceptable alcohol solutions or gels may contain from about 0% to about 95%, by weight of the composition, of an alcohol.

Alcohols suitable for inclusion in the alcohol solutions of the carrier include, but are not limited to, monohydric alcohols, dihydric alcohols, and combinations thereof. More preferred alcohols are selected from the group consisting of monohydric linear or branched $C_2$-$C_{18}$ alcohols. The most preferred alcohols are selected from the group consisting of ethanol, isopropanol, n-propanol, butanol, and combinations thereof. The cleaning formulations which contain an alcohol solution may be anhydrous or water containing.

Thickeners can be added to the water or alcohol based to form a gel. Examples of suitable thickeners include, but are not limited to, naturally-occurring polymeric materials such as sodium alginate, xanthan gum, quince seed extract, tragacanth gum, starch and the like, semi-synthetic polymeric materials such as cellulose ethers (e.g. hydroxyethyl cellulose, methyl cellulose, carboxymethyl cellulose, hydroxy propylmethyl cellulose), polyvinylpyrrolidone, polyvinyl alcohol, guar gum, hydroxypropyl guar gum, soluble starch, cationic celluloses, cationic guars and the like and synthetic polymeric materials such as carboxyvinyl polymers, polyvinylpyrrolidone, polyvinyl alcohol, polyacrylic acid polymers, polymethacrylic acid polymers, polyvinyl acetate polymers, polyvinyl chloride polymers, and polyvinylidene chloride polymers. Inorganic thickeners may also be used such as aluminum silicates, such as, for example, bentonites, or a mixture of polyethylene glycol and polyethylene glycol stearate or distearate.

The cleaning formulations can contain, in addition to the one or more preparations as described above, one or more antimicrobial or antifungal agents. Such agents are capable of destroying microbes, preventing the development of microbes or preventing the pathogenic action of microbes. Examples of additional antimicrobial and antifungal agents include β-lactam drugs, quinolone drugs, ciprofloxacin, norfloxacin, tetracycline, erythromycin, amikacin, 2,4,4'-trichloro-2'-hydroxy diphenyl ether (TRICLOSAN®), phenoxyethanol, phenoxy propanol, phenoxyisopropanol, doxycycline, capreomycin, chlorhexidine, chlortetracycline, oxytetracycline, clindamycin, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, ketaconazole, amanfadine hydrochloride, amanfadine sulfate, octopirox, parachlorometa xylenol, nystatin, tolnaftate, pyrithiones (especially zinc pyrithione which is also known as ZPT), dimethyldimethylol hydantoin (GLYDANT®), methylchloroisothiazolinone/methylisothiazolinone (KATHON CG®), sodium sulfite, sodium bisulfite, imidazolidinyl urea (Germall 115®), diazolidinyl urea (GERMAILL II®), benzyl alcohol, 2-bromo-2-nitropropane-1,3-diol (BRONOPOL®), formalin (formaldehyde), iodopropenyl butylcarbamate (POLYPHASE P100®), chloroacetamide, methanamine, methyldibromonitrile glutaronitrile (1,2-Dibromo-2,4-dicyanobutane or TEKTAMER®), glutaraldehyde, 5-bromo-5-nitro-1,3-dioxane (BRONIDOX®), phenethyl alcohol, o-phenylphenol/sodium o-phenylphenol, sodium hydroxymethylglycinate (SUTTOCIDE A®), polymethoxy bicyclic oxazolidine (NUOSEPt C®), dimethoxane, thimersal dichlorobenzyl alcohol, captan, chlφhenenesin, dichlorophene, chlorbutanol, glyceryl laurate, halogenated diphenyl ethers like 2,4,4'-trichloro-2'-hydroxy-diphenyl ether (TRICLOSAN® or TCS), 2,2'-dihydroxy-5,5'-dibromo-diphenyl ether, phenolic compounds like phenol, 2-methyl phenol, 3-methyl phenol, 4-methyl phenol, 4-ethyl phenol, 2,4-dimethyl phenol, 2,5-dimethyl pPhenol, 3,4-dimethyl phenol, 2,6-dimethyl phenol, 4-n-propyl phenol, 4-n-butyl phenol, 4-n-amyl phenol, 4-tert-amyl phenol, 4-n-hexyl phenol, 4-n-heptyl phenol, mono- and poly- alkyl and aromatic halophenols such as p-chloro-phenol, methyl p-chlorophenol, ethyl p-chlorophenol, n-propyl p-chlorophenol, n-butyl p-chlorophenol, n-amyl p-chlorophenol, sec-amyl p-chlorophenol, n-hexyl p-chlorophenol, cyclohexyl p-chlorophenol, n-heptyl p-chlorophenol, n-octyl p-chlorophenol, o-chlorophenol, methyl o-chlorophenol, ethyl o-chlorophenol, n-propyl o-chlorophenol, n-butyl o-chlorophenol, n-amyl o-chlorophenol, tert-amyl o-chlorophenol, n-hexyl o-chlorophenol, n-heptyl o-chlorophenol, o-benzyl p-chlorophenol, o-benzyl-m-methyl p-chlorophenol, o-benzyl-m, m-dimethyl p-chlorophenol, o-phenylethyl p-chlorophenol, o-phenylethyl-m-methyl p-chlorophenol, 3-methyl p-chlorophenol, 3,5-dimethyl p-chlorophenol, 6-ethy 1-3 -methyl p-chlorophenol, 6-n-propyl-3-methyl p-chlorophenol, 6-iso-propyl-3 -methyl p-chlorophenol, 2-ethyl-3,5-dimethyl p-chlorophenol, 6-sec-butyl-3 -methyl p-chlorophenol, 2-iso-propyl-3,5-dimethyl p-chlorophenol, 6-diethylmethyl-3 -methyl p-chlorophenol, 6-iso-propyl-2-ethyl-3 -methyl p-chlorophenol, 2-sec-amyl-3,5-dimethyl p-chlorophenol, 2-diethylmethyl-3,5-dimethyl p-chlorophenol, 6-sec-octyl-3-methyl p-chlorophenol, p-chloro-m-cresol, p-bromophenol, methyl p-bromophenol, ethyl p-bromophenol, n-propyl p-bromophenol, n-butyl p-bromophenol, n-amyl p-bromophenol, sec-amyl p-bromophenol, n-hexyl p-bromophenol, cyclohexyl p-bromophenol, o-bromophenol, tert-amyl o-bromophenol, n-hexyl o-bromophenol, n-propyl-m,m-dimethyl o-bromophenol, 2-phenyl phenol, 4-chloro-2-methyl phenol, 4-chloro-3 -methyl phenol, 4-chloro-3,5-dimethyl phenol, 2,4-dichloro-3,5-dimethylphenol, 3,4,5,6-terabromo-2-methylphenol, 5-methyl-2-pentylphenol, 4-isopropyl-3-methylphenol, para-chloro-meta-xylenol (PCMX), chlorothymol, 5-chloro-2-hydroxydiphenylmethane, resorcinol and its derivatives including methyl resorcinol, ethyl resorcinol, n-propyl resorcinol, n-butyl resorcinol, n-amyl resorcinol, n-hexyl resorcinol, n-heptyl resorcinol, n-octyl resorcinol, n-nonyl resorcinol, phenyl resorcinol, benzyl resorcinol, phenylethyl resorcinol, phenylpropyl resorcinol, p-chlorobenzyl resorcinol, 5-chloro 2,4-dihydroxydiphenyl methane, 4'-chloro 2,4-dihydroxydiphenyl methane, 5-bromo 2,4-dihydroxydiphenyl methane, and 4'-bromo 2,4-dihydroxydiphenyl methane, bisphenolic compounds like 2,2'-methylene his (4-chlorophenol), 2,2'-methylene bis (3,4,6-trichlorophenol), 2,2'-methylene bis (4-chloro-6-bromophenol), bis (2-hydroxy-3,5-dichlorophenyl) sulphide, and bis (2-hydroxy-5-chlorobenzyl)sulphide, benzoic esters (parabens) like methylparaben, propylparaben, butylparaben, ethylparaben, isopropylparaben, isobutylparaben, benzylparaben, sodium methylparaben, and sodium propylparaben, halogenated carbanilides (e.g., 3,4,4'-trichlorocarbanilides (TRICLOCARBAN® or TCC), 3-trifluoromethyl-4,4'-dichlorocarbanifide, 3,3',4-trichlorocarbanilide, etc.), cationic actives such as benzalkonium chloride, and clotrimazole. Another class of antimicrobial agents (specifically antibacterial agents) which are useful, are the so-called "natural" antibacterial actives, referred to as natural essential oils. Typical natural essential oil antibacterial actives include oils of anise, lemon, orange, rosemary, wintergreen, thyme, lavender, cloves, hops, tea tree, citronella, wheat, barley, lemongrass, cedar leaf, cedarwood, cinnamon, fleagrass, geranium, sandalwood, violet, cranberry, eucalyptus, vervain, peppermint, gum benzoin, basil, fennel, fir, balsam, menthol, ocmea origanum, Hydastis carradensis, Berberidaceae daceae, Ratanhiae and Curcuma longa.

The cleaning formulations may be packaged in a variety of suitable packaging known to those skilled in the art. The liquid formulations may desirably be packaged in manually operated spray dispensing containers, which are usually made of synthetic organic polymeric plastic materials. Accordingly, disinfecting formulations containing the one or more preparations of the present invention, and packaged in a spray dispenser, preferably in a trigger spray dispenser or a pump spray dispenser, are envisioned. Spray-type dispensers allow to uniformly apply to a relatively large area of a surface to be disinfected a liquid cleaning formulations described herein.

The preparations can be impregnated into a nonwoven absorbent wipe. Disinfectant wet wipes are also disclosed for example in U.S. Pat. No. 8,563,017.

The preparations can be in an aqueous foam with a special surfactant system capable of generating a foam. See U.S. Pat. No. 8,097,265, U.S. Pat. No. 5,891,922 and U.S. Pat. No. 4,889,645.

The preparations can also be in a pressurized spray aerosol. See also, U.S. Publication No. 20010053333 which discloses a liquid flash-dry aerosol disinfectant composition with a flash vaporization component and an effective amount of an antimicrobial agent.

It is within the abilities of one of ordinary skill in the art to determine the effective amount of the one or more preparations to include in an aerosol, foam, solution or disinfectant cloth for the purpose of sterilizing for example, high risk hospital surfaces.

D. Conjugation and Immobilization of Preparations, or Components Thereof

The one or more components may be presented as conjugated and/or immobilized compounds.

The one or more components of the one or more preparations may be conjugated with other agents in order to retain them on surfaces, for example, to prevent biofilm formation on a surface. In one embodiment, the one or more components of the one or more preparations may be conjugated to an agent that has affinity for a surface in order to retain the compounds on that surface. For example, they may be conjugated to an agent wherein the agent is a polymer or oligomer, and the polymer or oligomer has a high affinity for the surface.

Figure 7A:
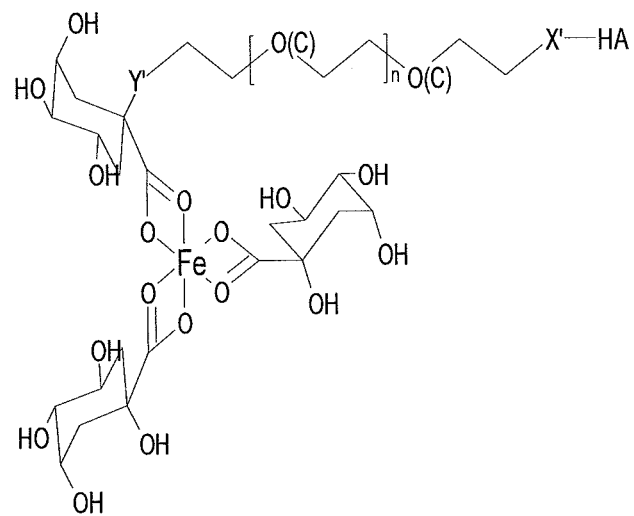
FIGS. 7A and B are chemical structures that illustrate how FeQ can be conjugated via a linker to a substance that binds to a surface. In both structures, the linker is spaced between functional groups Y' and X', attached to FeQ via Y' and to hydroxyapatite (HA) via X'. The figures differ in the point of attachment to the quinic acid ligand.
Figure 7B:
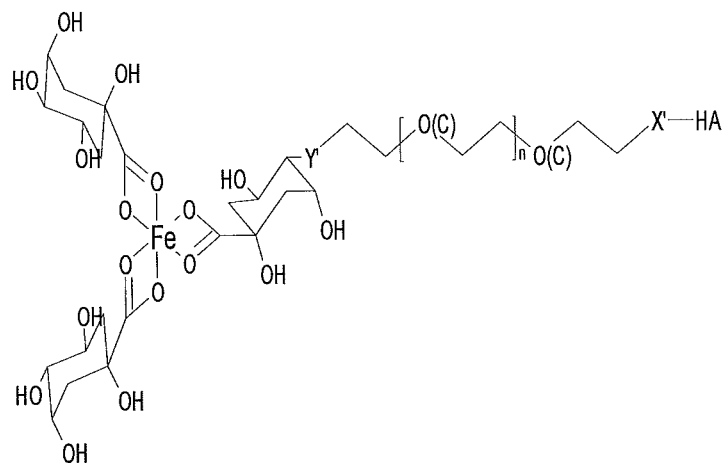

In another embodiment the one or more components of the one or more preparations may be conjugated to an agent wherein the agent comprises a reactive moiety suitable for anchoring to a surface. The reactive moiety may, for example, be photo-reactive, or capable of coupling covalently to a surface. The reactive moiety may also incorporate spacers and linkers and other functional groups in order to place the compound in a desired location relative to the surface. FIGS. 7A-C are examples of how FeQ (Fe-QA; ferric quinate) may be conjugated to an agent comprising a reactive moiety suitable for anchoring to a surface. In each of the three examples, FeQ is conjugated to a calix[4] arene frame that comprises a reactive moiety. In FIG. 7A, FeQ is conjugated via a linker to a calix[4] arene frame that contains a photoreactive functional group. FIG. 7B is a variant of FIG. 7A which shows that the reactive moiety can be positioned at a different location on the calix[4] arene frame. FIG. 7C is an example of FeQ conjugated to a calix[4] arene frame, wherein the latter is functionalized with thiol groups that are capable of reacting with surfaces. It should be understood that different linkers or no linkers may be used, and that other agents may be used instead of the calix[4] arene frame, including cyclodextrins and other polymers and oligomers.

In yet another embodiment, the one or more components of the one or more preparations may be conjugated to an agent that comprises a substance with an affinity for a surface. The agent may incorporate spacers and linkers and other functional groups in order to place the compound in the desired location relative to the surface. In one embodiment, the agent contains hydroxyapatite.

E. Feeds and Feed Supplements

One or more of the preparations can be formulated into growth promoting formulations.

F. Treatment to Promote Growth

Preparations containing the iron complexes above, are particularly useful in promoting growth. The one or more preparations may be added to animal feed or animal drinking water in order to promote growth. Addition of the one or more preparations to feed or drinking water results in improved growth. It has also been discovered that the one or more preparations can be added to animal feed or animal drinking water in order to decrease the mortality adjusted feed conversion ratio. Thus it is possible to use the one or more preparations to decrease the amount of feed necessary for an animal to grow. The one or more preparations may further be administered with other animal additives, and may be administered in commercial feeds. In a preferred embodiment, the one or more preparations are administered in feeds.

It has also been discovered that the one or more preparations can be administered to animals that are in a stressed environment in order to improve their growth performance In a stressed environment the one or more preparations promote growth that yields animals with higher average body weights. The one or more preparations also decrease mortality adjusted feed conversion ratios in stressed environments.

EXAMPLES

The following non-limiting examples are included to demonstrate particular embodiments of the various aspects of the present invention. In some instances, comparative examples are provided to show the effect of the preparations in comparison to preparations of Fe III complexes with quinate (FeQ), with DOPA (FeDOPA) or with phenylalanine (FePhe). It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Inhibition of Biofilm Formation on Beads Surface by *Enterococcus faecalis* NCTC 12697 using Fe-QA Materials and Methods Bacteria (*Enterococcus faecalis* NCTC 12697, *Staphylococcus epidermidis* F1513 and *Staphylococcus aureus* ATCC 25923) were grown on Brain heart infusion (BHI) passaged to new medium either containing Fe-QA or alone. Growth suspensions were prepared at 0.0001 OD/ml and then allowed to grow at 37° C. under nounal atmospheric conditions for 24 h in BHI with plastic coated UV beads (Lascells). After 48 h, 10 µl suspension was serially diluted 10 fold to 10-3, 10-4, 10-5, 10-6, 10-7, 10-8. For each dilution, 10 µl was spotted on BHI agar plates and colonies counted after 24 h. The beads were also removed washed in PBS before adding to 1 ml PBS. After vortex mixing, 10 µl of the cell suspension was serially diluted as above and cell counts carried out.

Results

*Enterococcus faecalis* causes many of the antibiotic resistant infections in hospitals, a consequence of its inherent resistance to certain antibiotics and of its ability to survive and proliferate in the intestinal tract. A Ser/Thr kinase in *Enterococcus faecalis* is found to mediate antimicrobial resistance. Studies have shown that PrkC, a one-component signaling protein containing a eukaryotic-type Ser/Thr kinase domain, allowed for inherent antimicrobial resistance and intestinal persistence of *E. faecalis* (Kristich, et al., *Proc. Nat. Acad. Sci. USA*, 104(9):3508-3513 (2007)). Kristich, et al. found that an *E. faecalis* mutant lacking PrkC grew at a wild-type rate in the absence of antimicrobial stress but showed enhanced sensitivity to cell-envelope-active compounds, including antibiotics that targeted cell-wall biogenesis and bile detergents. PrkC regulates physiological processes in *E. faecalis* that are key to its success as a nosocomial pathogen.

Figure 1B:
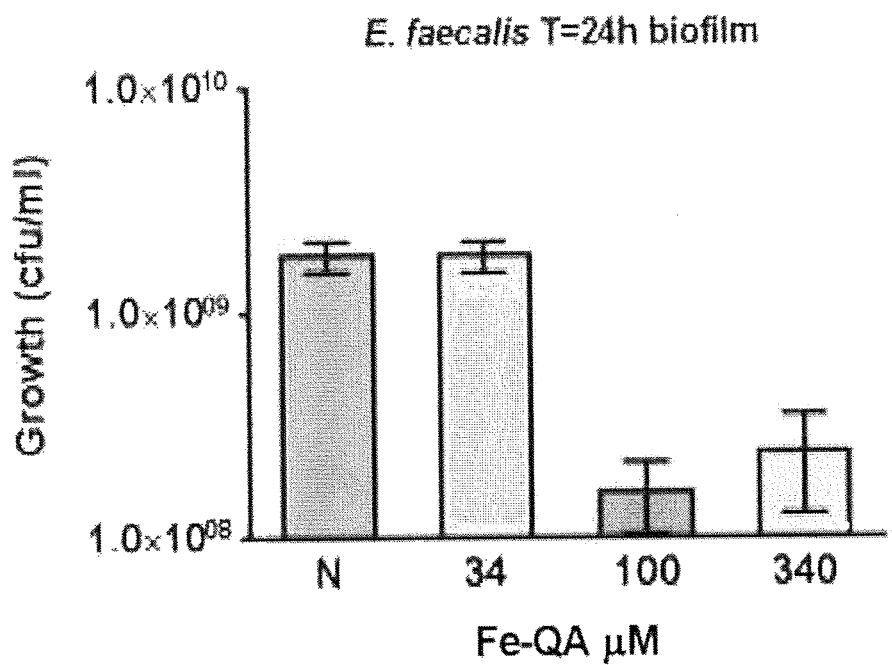
FIG. 1B is a bar graph showing biofilm formation by *Enterococcus faecalis* at time T=24 h in the presence or absence of different concentrations of Fe-QA.

The effect of Fe-QA on biofilm formation by *E. faecalis* was tested as described in the materials and methods. The data (FIGS. 1A and 1B) shows that Fe-QA inhibited *E. faecalis* biofilm formation as measured following treatment of *E. faecalis* grown on plastic coated UV beads.

Example 2

Inhibition of Biofilm Formation on Beads Surface by *Staphylococcus epidermidis* F1513 using Fe-QA Materials and Methods The effect of Fe-QA on biofilm formation by *S. epidermidis* F1513 was tested as described in the materials and methods of Example 1.

Results

Figure 2A:
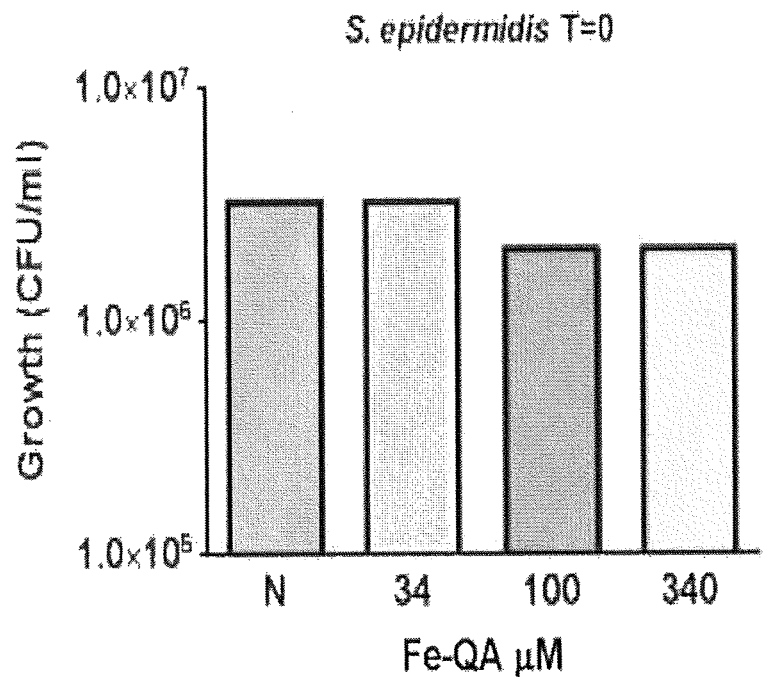
FIG. 2A is a bar graph showing biofilm formation by *Staphylococcus epidermidis* at time T=0 in the presence of absence of different concentrations of Fe-QA.
Figure 2B:
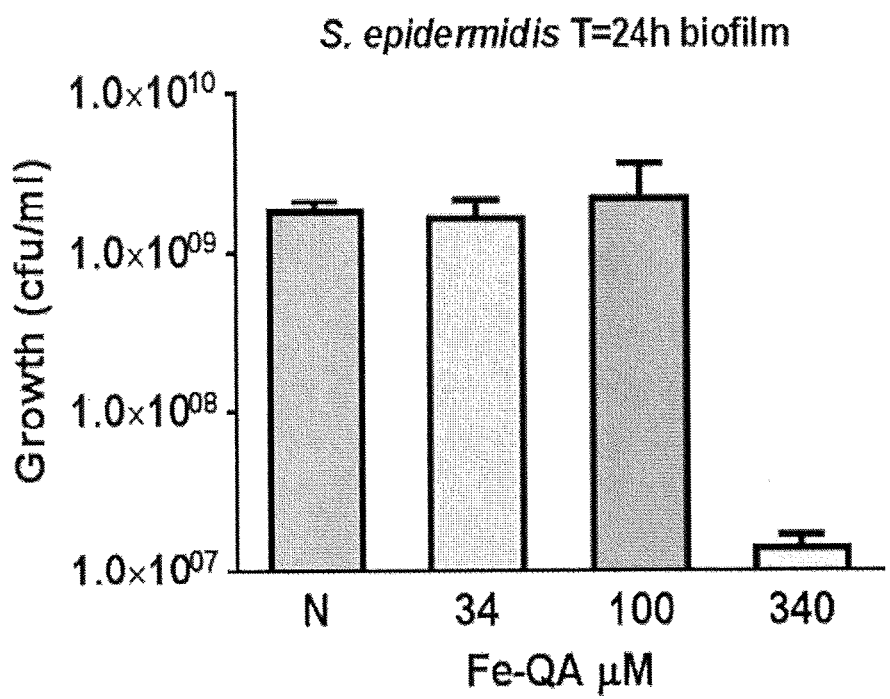
FIG. 2B is a bar graph showing biofilm formation by *Staphylococcus epidermidis* at time T=24 h in the presence of absence of different concentrations of Fe-QA.

The data (FIG. 2A and 2B) shows that Fe-QA inhibited *S. epidermidis* biofilm formation as measured following treatment of *S. epidermidis* grown on plastic coated UV beads.

Example 3

Inhibition of Biofilm Formation on Beads Surface by *Staphylococcus aureus* ATCC 25923 using Fe-QA The treatment of choice for *S. aureus* infection is penicillin; in most countries, however, penicillin resistance is extremely common, and first-line therapy is most commonly a penicillinase-resistant β-lactam antibiotic (for example, oxacillin or flucloxacillin). Combination therapy with gentamicin may be used to treat serious infections, such as endocarditis, but its use is controversial because of the high risk of damage to the kidneys (Cosgrove, et al., *Clin Infect Dis*, 48(6):713-721 (2009). The duration of treatment depends on the site of infection and on severity.

Materials and Methods

The effect of Fe-QA on biofilm formation by *S. aureus* was tested as described in the materials and methods of Example 1.

Results

Figure 3A:
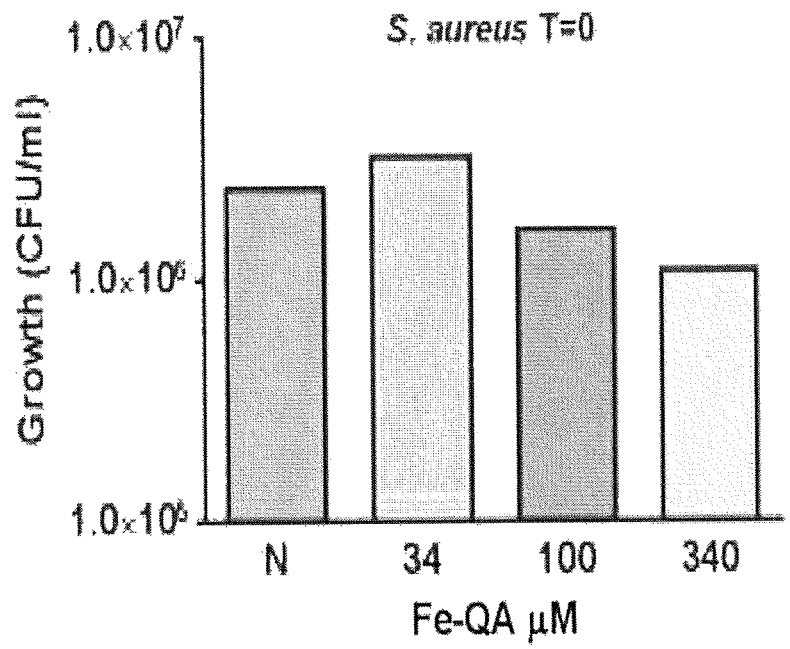
FIG. 3A is a bar graph showing biofilm formation by *Staphylococcus aureus* at time T=0 in the presence of absence of different concentrations of Fe-QA.
Figure 3B:
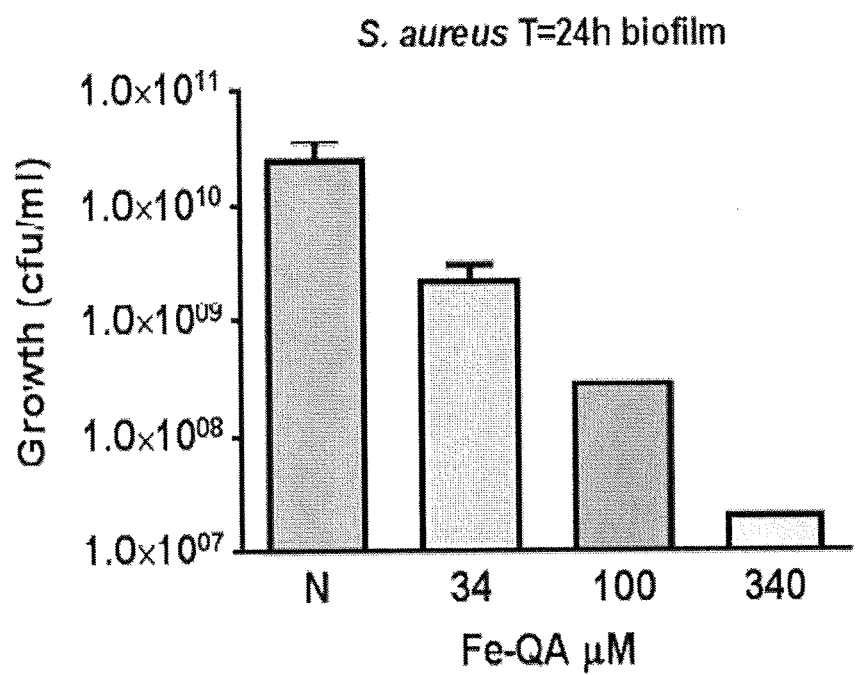
FIG. 3B is a bar graph showing biofilm formation by *Staphylococcus aureus* at time T=24 h in the presence of absence of different concentrations of Fe-QA.

The data (FIG. 3A and 3B) shows that Fe-QA inhibited *S. aureus* biofilm formation as measured following treatment of *S. aureus* grown on plastic coated UV beads.

Example 4

Fe-QA Prevention of Biofilm Formation by *Pseudomonas Aeruginosa* and Uropathogenic *E. coli* (UPEC).

Materials and Methods

*Pseudomonas aeruginosa* PAO-1, and a clinically isolated uropathogenic *Escherichia coli* UPEC-536 were routinely grown on either LB (Luria-Bertani, Oxoid, UK) agar plates at 37° C. or in broth at 37° C. with 200 rpm shaking UV-sterilized glass slides were incubated in either 15 mL RPMI-1640 defined medium (Sigma, UK) or 15 mL RPMI-1640 with Fe-QA inoculated with diluted ($OD_{600}$=0.01) bacteria from overnight cultures at 37° C. with 60 rpm shaking for 72 hours. The slides were removed from bacterial culture and washed with 15 mL phosphate buffered saline at room temperature for 5 minutes three times and then rinsed with distilled $H_2O$. After washing, the slides were stained with 20 μM SYTO17 dye (Invitrogen, UK) at room temperature for 30 minutes. After removing excess staining dye and air-drying, the samples were examined using a Carl Zeiss LSM 700 Laser Scanning Microscope with ZEN 2009 imaging software (Carl Zeiss, Germany). The coverage rate of bacteria on the surface was analysed using open source Image J 1.44 software (National Institute of Health, US).

Results

Figure 4A:
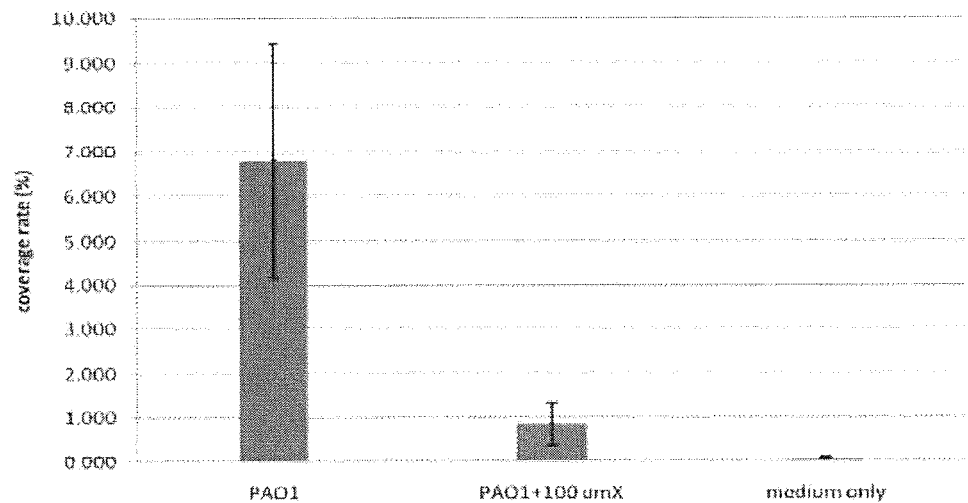
FIG. 4A is a bar graph showing the coverage rate of PAO1 *Pseudomonas aeruginosa* on the surface of a glass slide, comparing *Pseudomonas* medium only as a control, PAO1 *Pseudomonas*+100 µM Fe-QA treatment, and PAO1 *Pseudomonas* with no Fe-QA (X=Fe-QA). The graph shows that 100 µM Fe-QA ("X") inhibits the formation of biofilm by *P. aeruginosa*.

FIG. 4A shows that Fe-QA ("X") at 100 μM inhibits the formation of biofilm by *Pseudomonas aeruginosa*. In the absence of Fe-QA, a higher coverage rate was measured for *Pseudomonas aeruginosa* than in the presence of a 100 μM concentration of Fe-QA.

Figure 4B:
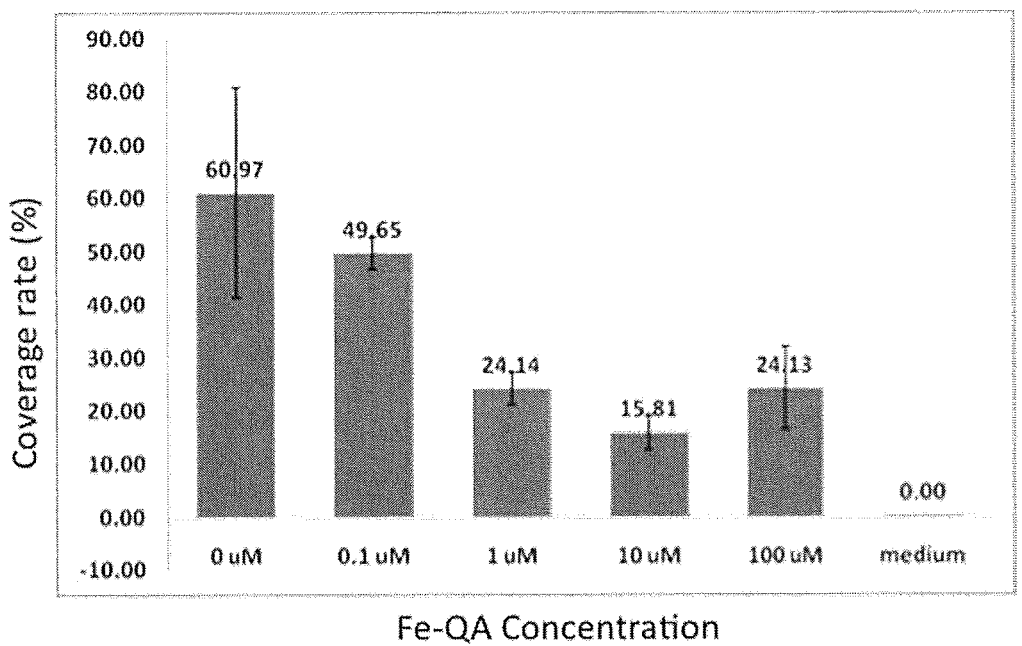
FIG. 4B is a bar graph showing that Fe-QA inhibits founation of biofilm by Uropathogenic *E. coli* (UPEC). The bar graph shows the coverage rate of UPEC on the surface of a glass slide compared to a UPEC medium only control, and UPEC growing in the presence of 0.1 µM, 10 µM, and 100 µM concentrations of Fe-QA.

FIG. 4B shows that Fe-QA inhibits the formation of biofilm by Uropathogenic *E. coli* (UPEC). In the absence of Fe-Q ("0 μM), a higher coverage rate is measured for UPEC than in the presence of 0.1 μM, 1 μM, 10 μM and 100 μM concentrations of Fe-QA.

Example 5

FeQ prevents Attachment of Bacteria to Surfaces

Materials and Methods

Enteropathogenic *E. coli* (EPEC) E2348/69 were grown in wells for 48 hours at 37° C. in the presence of FeQ (100 μM), and in the absence of FeQ (as control). After 48 hours, the wells were washed in order to remove suspended cells. Crystal violet was then added to each well. The wells were then washed to remove excess dye. A mixture of acetone/ethanol was then added to the wells to re-suspend any cells attached to the plastic surface of the wells, and dissolve any dye present. The presence of dye in each well was then quantified by measuring the O.D. at 570 nm.

Results

Figure 5:
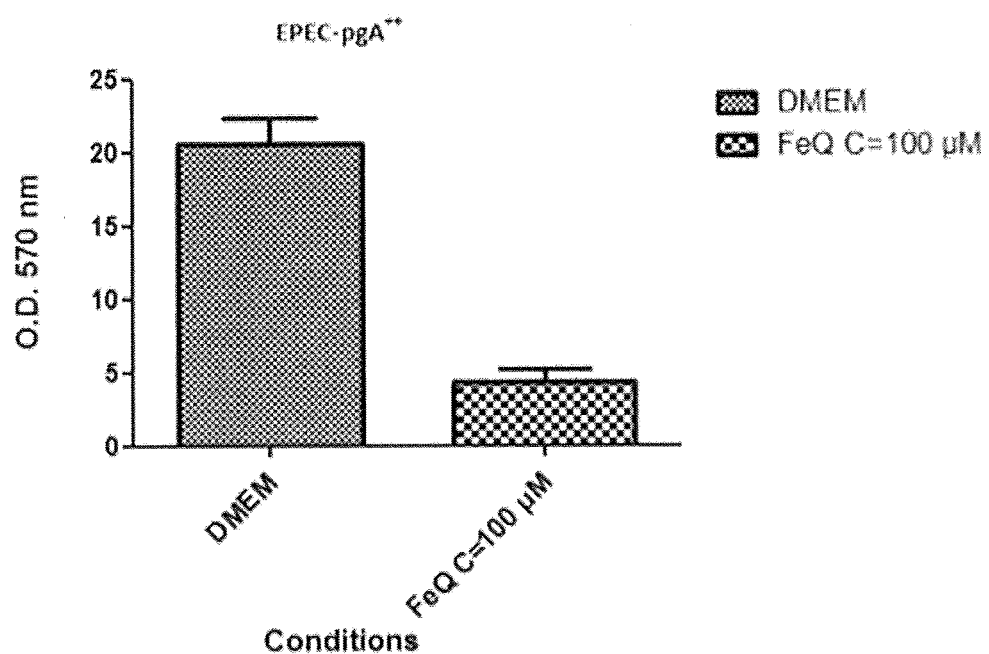
FIG. 5 shows quantitatively the difference in the attachment of EPEC cells to the plastic well surface in the absence and presence of FeQ by measurement of the optical absorbance of crystal violet that was absorbed by EPEC cells attached to the surface.
Figure 6A:
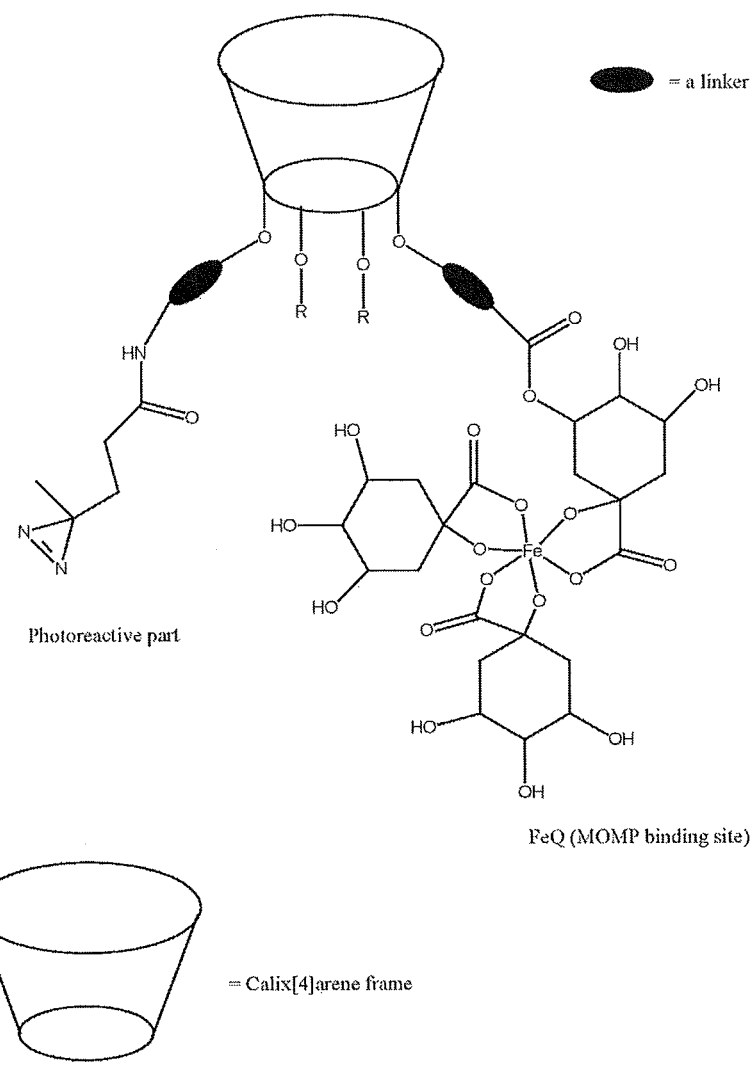
FIGS. 6A-C show chemical structures of how FeQ can be conjugated to an agent that contains a reactive functional group suitable for immobilizing FeQ, for example, on a surface.
Figure 6B:
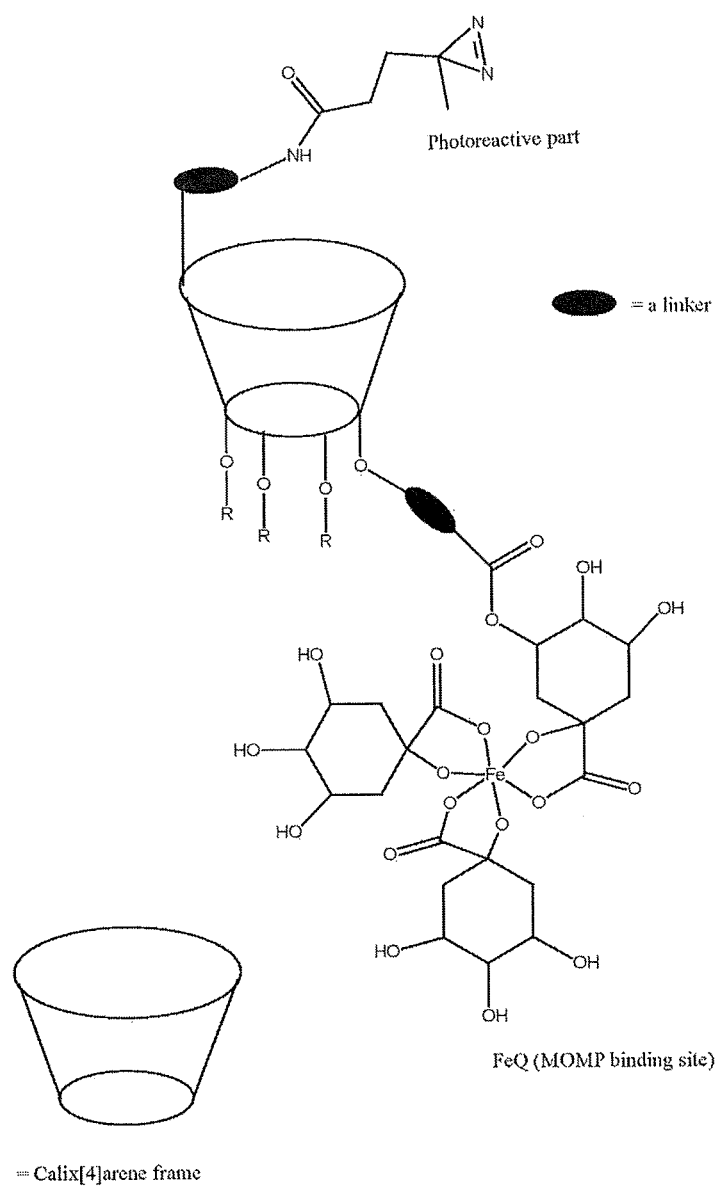
Figure 6C:
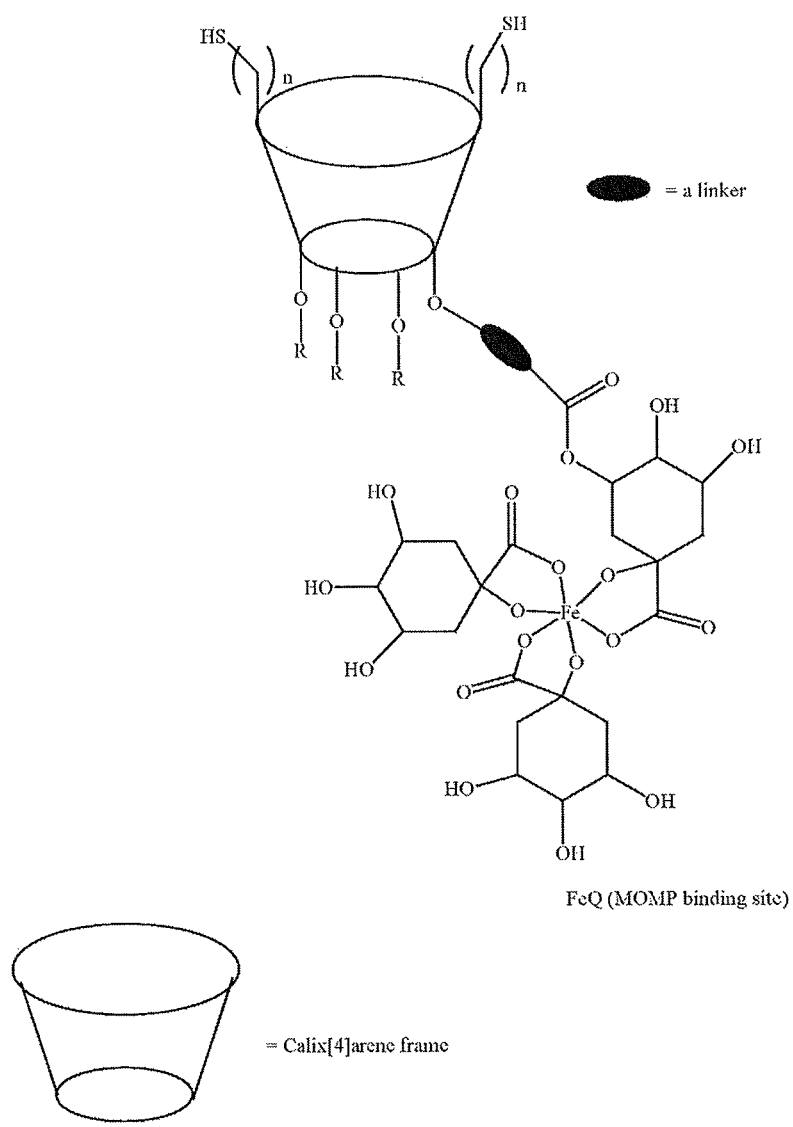

In the absence of FeQ, EPEC binds to the plastic surface and forms a biofilm that is readily detected by dying with crystal violet However, in the presence of FeQ, EPEC is unable to attach to the plastic surface and form a biofilm, and is not detected by adding crystal violet. FIG. 5 shows quantitatively the difference in the attachment of EPEC cells to the plastic well surface in the absence and presence of FeQ by measurement of the optical absorbance of crystal violet that was absorbed by EPEC cells attached to the surface. At an FeQ concentration of 100 μM there is little or no attachment of bacterial cells to the surface and no biofilm formation.

Example 6

FeQ prevents Formation of Biofilm on Human Teeth

Materials and Methods

Molar teeth were extracted from human patients, and mouth swabs taken from each patient to obtain samples of each patient's bacterial flora present in the mouth. The mouth swabs were cultured in the laboratory using LB media in order to grow bacterial populations ordinarily present in the mouth of each patient. The extracted teeth were washed and brushed extensively using PBS buffer and ethanol. Each patient's tooth was then placed in the bacterial culture prepared from that patient's bacterial flora sample, and cultured aerobically for 24 hours in LB media. The teeth were then stained with CEPLAC™ (Manx Healthcare Ltd, Warwick, UK), and washed three times with PBS-Tween (50 mL) to determine if biofilm had been formed on the teeth.

Results

All teeth stained red indicating the presence of biofilm on the teeth after just 24 hours. The same teeth were then cleaned using PBS buffer and ethanol, and the procedure repeated except with 48 hours of culturing in the presence of FeQ (340 µM). After 48 hours, no teeth stained red demonstrating that biofilms could not be established on the teeth in the presence of FeQ.

Example 7

Efficacy of FeQ and a Preparation Produced According to Example 14 ("FeTyr") to Reduce Campylobater Carriage in Chickens and Promote Growth in Chickens Materials and Methods A study was performed to evaluate growth promotion and reduction of Campylobater carriage using FeQ and FeTyr in Ross 308 male broilers with 7 treatment groups. Each treatment group comprised four replicates of 10 birds per pen (40 birds/treatment group and 4 pens of 10 birds/treatment group), and there were 2 control groups and 5 test groups. All the test groups and one of the control groups were exposed at day 20 of the trial to dirty litter, which tested positive for Campylobacter. This method was used to provide a more natural method to Campylobater challenge the birds. Thus there was a positive control where one treatment group was challenged with Campylobacter and one negative control group where the birds were not challenged, and five treatment groups that were all challenged with Campylobacter. The total number of birds used in the 7 treatment groups was 280. Details of the treatments are provided in Table 1. Treatment group 1 was a negative control where birds just received the commercial feed, and were not challenged with dirty litter containing Campylobacter. Treatment group 2 was the positive control where the birds received the commercial feed, and were challenged with dirty litter containing Campylobacter at day 20. Treatment group 3 received 0.22 g/L of FeQ in their drinking water and 0.22 g/Kg FeQ in their feed during the entire trial, and was challenged with dirty litter containing Campylobater at day 20. Treatment group 5 received 0.22 g/L of FeQ in their drinking water during the entire trial, and was challenged with dirty litter containing Campylobater at day 20. Treatment group 6 received 0.22 g/kg FeQ in their feed during the entire trial, and was challenged with dirty litter containing Campylobater at day 20. Treatment group 7 received 0.022 g/L FeQ in their drinking water during the entire trial, and was challenged with dirty litter containing Campylobater at day 20. Treatment group 8 received 0.02 g/L FeTyr in their drinking water during the entire trial, and was challenged with dirty litter containing Campylobater at day 20. The FeTyr was pre-dissolved in DMSO, and diluted to provide a solution of 0.02 g/L of FeTyr in water. (An additional treatment group 4 was terminated due to solubility issues.)

TABLE 1

Treatment Details

| Treatment | Description | Campylobacter Challenge |
|---|---|---|
| 1 | Control-1 Commercial feed | No |
| 2 | Control-2 Commercial feed | Yes |
| 3 | 0.22 g/L FeQ in water + 0.22 g/kg FeQ in feed | Yes |
| 5 | 0.22 g/L FeQ in water | Yes |
| 6 | 0.22 g/kg FeQ in feed | Yes |
| 7 | 0.022 g/L FeQ in water | Yes |
| 8 | 0.02 g/L FeTyr in water | Yes |

The birds were fed with a commercial three-phase feeding program using starter, grower and finisher feeds with formulations shown in Table 2. All diets had coccidiostat (MAXIBAN® at 0.0625% in starter and finisher phase diets and MONTEBAN® at 0.06% in finisher phase). Xylanase (RONOZYME® WX at 200 g per ton) and phytase (RONOZYME® P at 150 grams per ton) were added to all diets.

TABLE 2

Basal feed formulation for starter, grower and finisher diets

| Raw Material | STARTER % | GROWER % | FINISHER % |
|---|---|---|---|
| Barley | 10.5 | 8.4 | 7.2 |
| Wheat | 50.0 | 55.0 | 60.0 |
| Soya Ext Hipro | 26.0 | 23.0 | 19.0 |
| Full fat Soya Cherwell | 5.0 | 5.0 | 5.0 |
| L Lysine HCl | 0.40 | 0.30 | 0.30 |
| DL-methionine | 0.40 | 0.35 | 0.30 |
| L-threonine | 0.15 | 0.15 | 0.15 |
| Soya Oil | 4.0 | 4.50 | 4.75 |
| Limestone | 1.25 | 1.25 | 1.25 |
| MonoCal phosphate | 1.50 | 1.25 | 1.25 |
| Salt | 0.25 | 0.25 | 0.25 |
| Sodium bicarbarbonate | 0.15 | 0.15 | 0.15 |
| Broiler Premix | 0.40 | 0.40 | 0.40 |
| Nutrient | Analysis | Analysis | Analysis |
| Fat (ether extract) | 6.34 | 6.85 | 7.11 |
| Protein | 21.85 | 20.64 | 19.14 |
| Fibre | 3.08 | 3.02 | 2.97 |
| Ash | 6.01 | 5.68 | 5.50 |
| ME-P | 12.78 | 13.04 | 13.22 |
| Total lysine | 1.45 | 1.28 | 1.17 |
| Available lysine | 1.35 | 1.19 | 1.09 |
| Methionine | 0.69 | 0.62 | 0.55 |
| Total methionine and cysteine | 1.03 | 0.95 | 0.85 |
| Threonine | 0.91 | 0.86 | 0.79 |
| Tryptophan | 0.25 | 0.23 | 0.21 |
| Calcium | 0.95 | 0.91 | 0.89 |
| Phosphorus | 0.72 | 0.66 | 0.65 |
| Available phosphorus | 0.48 | 0.42 | 0.42 |
| Salt | 0.30 | 0.30 | 0.30 |
| Sodium | 0.17 | 0.17 | 0.17 |
| Vit A | 13.20 | 13.5 | 13.50 |
| Vit D3 | 5.0 | 5.0 | 5.00 |
| Vit E | 100 | 100 | 100 |

The feeding program is show in Table 3. The birds were reared in floor pens to day 42, and fed starter, grower and finisher feed at day 0 to 11, 11 to 24, and 24 to 42 days, respectively. All birds were weighed individually and feed weigh backs recorded per pen at day 0, 11, 21, 24 and 42 days.

TABLE 3

Feeding Program

| | Feeding Phase | | |
|---|---|---|---|
| | Starter | Grower | Finisher |
| (days of age) | 0-11 | 11-24 | 24-42 |

Prior to challenging the chickens with dirty litter containing *Campylobacter* at day 20, each pen was tested for *Campylobater* using cloacal swabs. All pens tested negative for *Campylobater* prior to the challenge. At day 20, litter, which was naturally *Campylobacter*-contaminated was tested to confirm the presence of *Campylobacter*, and then added (approximately 2 kg/pen) to the litter in all pens except in pens for treatment group 1 (the negative control). At day 28, the pen litter was sampled to confirm the presence or absence of *Campylobacter*. At day 41 and 42, caecal samples were taken from 3 birds per pen (12 birds per treatment group) and tested for *Campylobater* enumeration. At day 42, digesta, fecal samples, and caecal content was taken from all birds, and pooled per pen. Two birds per pen were also taken from treatment groups 1-3, euthanized, and blood samples taken. Samples were analyzed for blood chemistry, including analysis for alkaline phosphatase, aspartate amino transferase, alanine amino transferase, gamma-glutamyl transferase, lactate dehydrogenase, total protein, albumin, globulin, amylase and glucose.

In order to minimize risk of cross-contamination, standard industry biosecurity measures were used including: disinfecting boots, changing overshoes and gloves between pens/treatments, entering Campylobacter negative pens before entering *Campylobater* positive pens, and leaving adjacent pens empty. Daily health, culls, and mortality were recorded. All bird weights were recorded at 0, 11, 21, 24, 33 and 42 days. Weight gains, feed intake and feed conversion ratio (FCR) were derived for each feeding period.

The effect of the treatment groups compared to the negative control group (treatment group 1) and the positive control group (treatment group 2) is shown in Tables 5-12 for the periods 0-11 days, 11-20 days, 20-25 days, 11-25 days, 25-42 days, 20-42 days, 0-20 days, and 0-42 days.

Results

Figure 8:
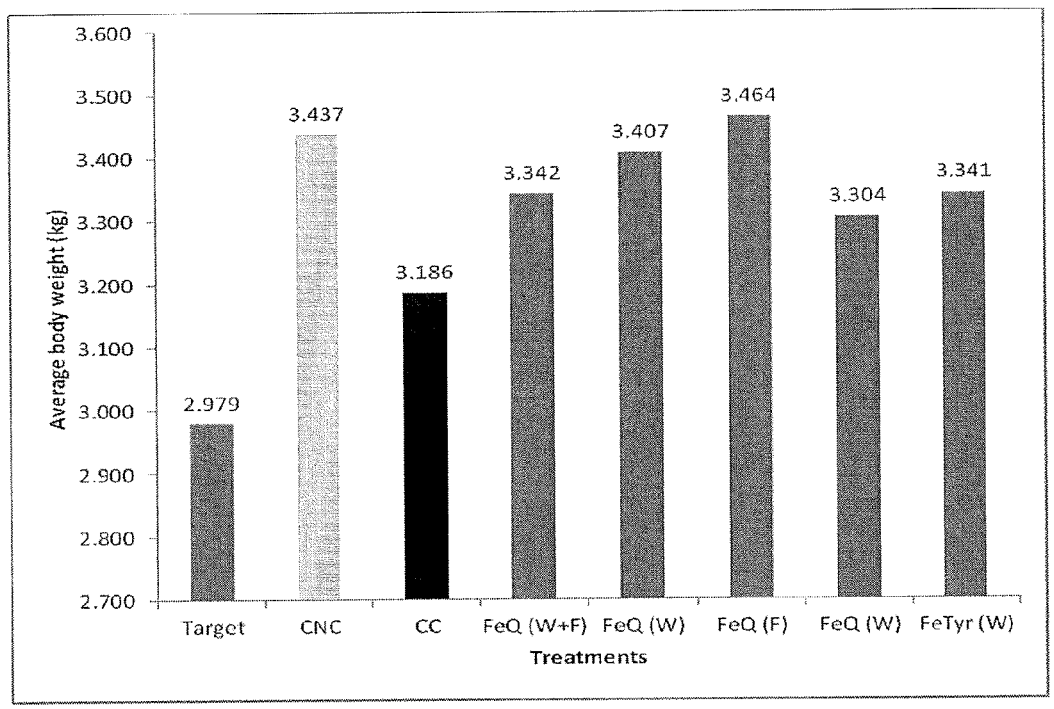
FIG. 8 is a graph showing the average body weight (ABW) of chicken after 42 days of growth. The graph compares the ABW at 42 days of chicken challenged with *Campylobacter*-infected dirty litter at day 20 and treated from days 0-42 with FeQ or a preparation obtained by the method of Example 14 (labelled "FeTyr") to (i) a standard commercial target (of 2.979 kg) labeled "Target", (ii) a negative control (of 3.437 kg) labeled "CNC" where the chicken were not challenged with *Campylobacter*-infected dirty litter, and (iii) a positive control (of 3.186 kg) labeled "CC" where the chicken were challenged with *Campylobacter*-infected dirty litter. The graph shows that birds challenged with *Campylobacter*-infected dirty litter have higher ABW at 42 days compared to the positive control (labeled "CC") when treated with (iv) FeQ at 0.22 g/L in drinking water and FeQ at 0.22 g/kg in feed, labeled "FeQ(W+F)" with an ABW of 3.342 kg, (v) FeQ at 0.22 g/L in drinking water, labeled "FeQ(W)" with an ABW of 3.407 kg, (vi) FeQ at 0.22 g/kg in feed, labeled "FeQ(F)" with an ABW of 3.464 kg, (vii) FeQ at 0.022 g/L in drinking water, labeled "FeQ(W)" with an ABW of 3.304 kg, and (viii) FeTyr at 0.02 g/L in drinking water labeled FeTyr(W) with an ABW of 3.341 kg.

FIG. 8 shows the average body weight at day 42 for all treatment groups, and a comparison to a commercial control labeled "Target". The figure shows that treatment group 1 (the negative control labeled "CNC") attained an average body weight (ABW) of 3.437 kg at day 42 (which was higher than the commercial target of 2.979 kg). The positive control (labeled "CC"), which was challenged with dirty litter containing *Campylobater* at day 20, in contrast only attained an ABW of 3.186 kg at day 42, which was significantly less than the negative control (treatment group 1). This result demonstrates that challenging with dirty litter contaminated with *Campylobacter* resulted in a reduction of growth of the chicken by an average of 251 grams. However, when the chickens were challenged with dirty litter containing *Campylobacter* but treated with FeQ or FeTyr in treatment groups 3, 5, 6, 7 and 8, all treatment groups performed better than the positive control demonstrating that FeQ and FeTyr treatment had a positive effect on growth. In fact, FeQ in feed at 0.22 g/kg (treatment group 6) produced chicken with an ABW of 3.464 kg, which was higher than the negative control ABW of 3.437 kg even though treatment group 6 had been challenged with dirty litter containing Campylobacter.

Figure 9:
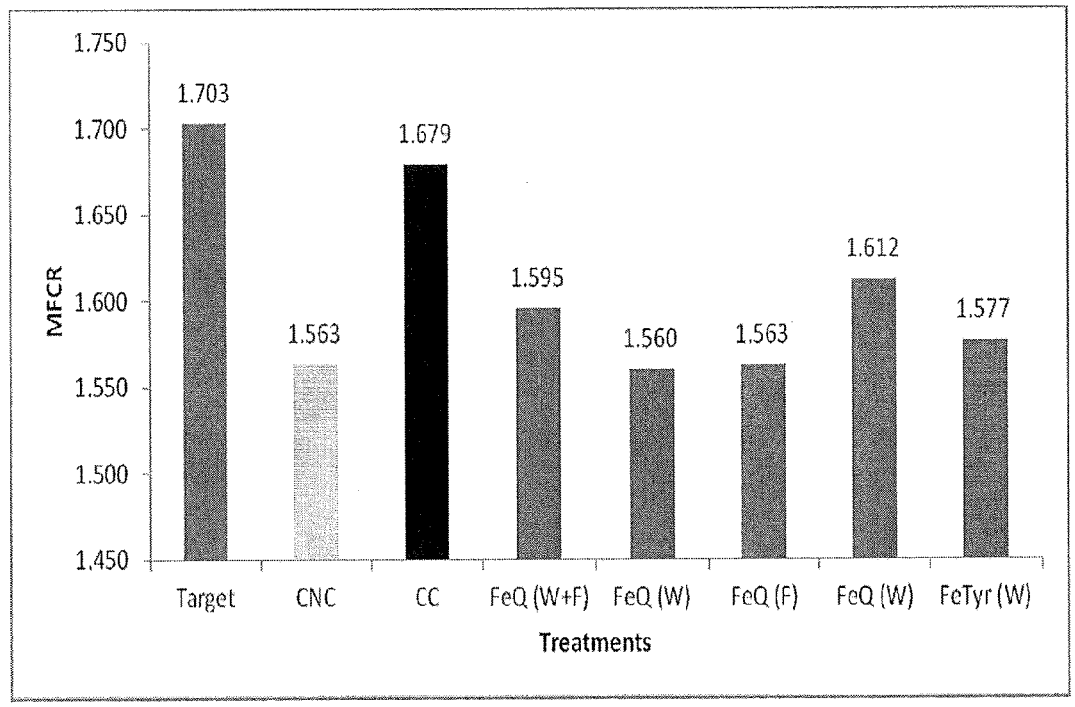
FIG. 9 is a graph showing the mortality adjusted feed conversion ratio (MFCR) of chicken after 42 days of growth. The graph compares the MFCR at 42 days of chicken challenged with *Campylobacter*-infected dirty litter at day 20 and treated from days 0-42 with FeQ or a preparation obtained by the method of Example 14 (labelled "FeTyr")to (i) a standard commercial target (of 1.703) labeled "Target", (ii) a negative control (of 1.563) labeled "CNC" where the chicken were not challenged with *Campylobacter*, and (iii) a positive control (of 1.679) labeled "CC" where the chicken were challenged with *Campylobacter*-infected dirty litter. The graph shows that birds challenged with *Campylobacter*-infected dirty litter have lower MFCR at 42 days compared to the positive control (labeled "CC") when treated with (iv) FeQ at 0.22 g/L in drinking water and FeQ at 0.22 g/kg in feed, labeled "FeQ(W+F)" with a MFCR of 1.595, (v) FeQ at 0.22 g/L in drinking water, labeled "FeQ(W)" with a MFCR of 1.560, (vi) FeQ at 0.22 g/kg in feed, labeled "FeQ(F)" with a MFCR of 1.563, (vii) FeQ at 0.022 g/L in drinking water, labeled "FeQ(W)" with a MFCR of 1.612, and (viii) FeTyr at 0.02 g/L in drinking water, labeled FeTyr(W) with a MFCR of 1.577.

FIG. 9 shows the mortality adjusted feed conversion rate (MFCR) at day 42 for all treatment groups, and a comparison to a commercial control labeled "Target". (A lower MFCR number is a better result.) The figure shows that treatment group 1 (the negative control labeled "CNC") had a MFCR of 1.563, which was lower than the commercial target of 1.703. The positive control, labeled "CC" which was challenged with the dirty litter containing *Campylobater* at day 20 had a significantly higher MFCR of 1.679 than the negative control. Thus challenging with dirty litter infected with *Campylobacter* resulted in a higher MFCR. However, when the chickens were challenged with dirty litter infected with *Campylobater* but treated with FeQ or FeTyr in treatment groups 3, 5, 6, 7 and 8, all treatment groups performed better than the positive control demonstrating that FeQ and FeTyr treatment had a positive effect on MFCR (i.e. decreasing the numerical MFCR). The results show that treatment groups 3, 5, 6, 7 and 8 had MFCR values of 1.595, 1.560, 1.563, 1.612 and 1.577, respectively. Furthermore, treatment groups 5 and 6 performed as well as the negative control even when challenged with dirty litter containing Campylobacter.

Figure 10:
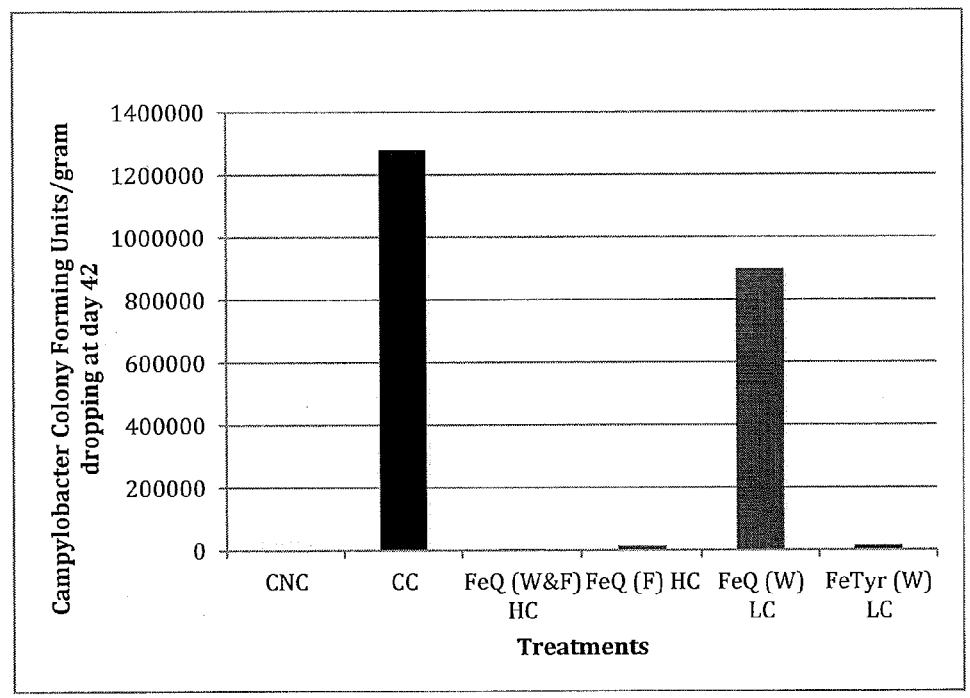
FIG. 10 is a graph showing the number of *Campylobacter* colony forming units per gram (cfu/g) of bird droppings at day 42. The graph compares the cfu/g at day 42 of chicken that were challenged with *Campylobacter*-infected dirty litter at day 20 and treated from days 0-42 with FeQ or a preparation obtained by the method of Example 14 (labelled "FeTyr") to (i) a negative control labeled "CNC" (with a cfu/g of 28,000) where the chicken were not challenged with *Campylobacter*-infected dirty litter, and (ii) a positive control labeled "CC" (with a cfu/g of 1,280,000) where chickens were challenged with *Campylobacter*-infected dirty litter at day 21. The graph shows that birds treated with FeQ or FeTyr have lower levels of *Campylobacter* in their droppings at day 42 when treated with (iii) FeQ at 0.22 g/L in drinking water and FeQ at 0.22 g/kg in feed, labeled "FeQ(W+F)" with a cfu/g of 4,860, (iv) FeQ at 0.22 g/kg in feed, labeled "FeQ(F)" with a cfu/g of 12,800, (v) FeQ at 0.022 g/L in drinking water, labeled "FeQ(W)" with a cfu/g of 900,000, and (vi) FeTyr at 0.02 g/L in drinking water, labeled FeTyr(W) with a cfu/g of 16,600.

FIG. 10 shows the number of *Campylobater* colony forming units per gram (cfu/g) of bird droppings at day 42 for treatment groups 1-3 and 6-8. (A lower number is a better result.) The results show that treatment groups 3 and 6-8 all performed better than the positive control (treatment group 2) demonstrating that FeQ and FeTyr had a positive effect on reducing *Campylobacter* infection of poultry. Notably, chicken treated with FeTyr, FeQ in feed, and FeQ in feed and water all had colony forming units of *Campylobacter* per gram of dropping that were similar to, or less than, those of the negative control group (treatment group 1). The detection of low levels of *Campylobater* in the negative controls demonstrates how highly contagious the bacterium is, and is likely to be an indication that a small number of birds in the negative control group became infected despite not being experimentally challenged with dirty litter. The results in FIG. 10 for the low concentration of FeQ in water (0.022 g/L; treatment group 7) appears to show less of an effect than the other treatment groups, although this difference was considered more likely due to experimental error for example following cross contamination of samples. As discussed below, the results obtained from a further experiment, as given in FIG. 11 confirm that treatment group 7 did, indeed, also provide the highly beneficial effect.

Figure 11:
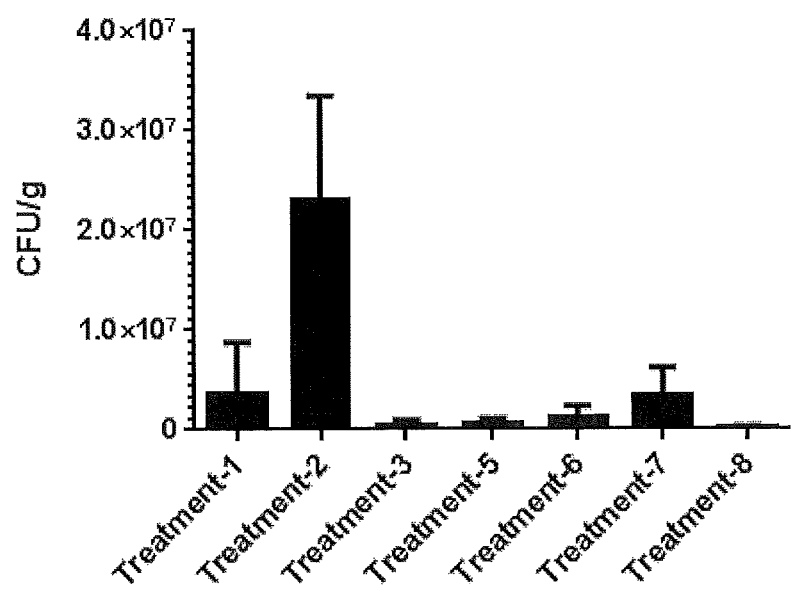
FIG. 11 is a graph showing the average number of *Campylobacter* colony forming units per gram (cfu/g) of caeca samples at day 42. The graph compares the cfu/g at day 42 of chicken that were challenged with *Campylobacter*-infected dirty litter at day 20 and treated from days 0-42 with FeQ or a preparation obtained by the method of Example 14 (labelled "FeTyr") to (i) a negative control labeled "Treatment-1" where the chicken were not challenged with *Campylobacter*-infected dirty litter, and (ii) a positive control labeled "Treatment-2" where chickens were challenged with *Campylobacter*-infected dirty litter at day 21. The graph shows that birds treated with FeQ or FeTyr have lower levels of *Campylobacter* in their caeca at day 42 when treated with (iii) FeQ at 0.22 g/L in drinking water and FeQ at 0.22 g/kg in feed, labeled "Treatment-3", (iv) FeQ at 0.22 g/L in water, labeled "Treatment-5", (v) FeQ at 0.22 g/kg in feed, labeled "Treatment-6", (vi) FeQ at 0.022 g/L in drinking water, labeled "Treatment-7", and (vii) FeTyr at 0.02 g/L in drinking water, labeled "Treatment-8".

FIG. 11 shows the average number of *Campylobater* colony forming units per gram (cfu/g) of caeca samples at day 42 for treatment groups 1-3 and 5-8. The results show that all the treatment groups (3 and 5-8) all performed better than the positive control (treatment group 2) demonstrating that FeQ and FeTyr had a positive effect on reducing *Campylobacter* infection of poultry.

The effect of the treatments on overall liveability and European production and efficiency factor (EPEF) is shown in Table 4. (EPEF=[ (Liveability×Live weight in kg at end of trial/Age in Days×FCR commercial)×100].

The effect of FeQ treatment on growth performance in the absence of *Campylobacter* challenge during the starter phase (0-11 days) and period from 0-20 days is shown in Table 13. Since the negative and positive controls (treatment groups 1 and 2) are identical prior to challenge with the dirty litter at day 20, these groups may be pooled for comparison to treatment groups 3, 5, 6, and 7 in order to see if FeQ had an effect on growth in the absence of a challenge by dirty litter contaminated with *Campylobacter l during the first* 20 days of growth. The results demonstrate that FeQ promotes growth of chicken even in the absence of a challenge from dirty litter contaminated with *Campylobacter*. At day 20, the average body weight (ABW) for the control groups (treatment groups 1 and 2) is 0.927 kg versus 0.963 kg for treatment groups 3, 5, 6 and 7 which all received FeQ. This improvement in body weight is also reflected in a significantly better MFCR for the FeQ treated birds. Table 10 shows the MFCR for the birds treated in groups 3, 5, 6 and 7 is 1.2996 versus 1.3374 for the control groups (treatment groups 1 and 2). Notably the P-value is less than 0.05.

The same positive effect of FeTyr treatment on growth performance in the absence of *Campylobater* challenge is also evident from Table 10. The AWG during the first 20 days of production for chicken treated with FeTyr (treatment group 8) is 0.895 kg compared to 0.884 and 0.889 kg for treatment groups 1 and 2 (negative and positive controls). Furthermore, the MFCR during the first 20 days of production for chicken treated with FeTyr (treatment group 8) is 1.311 versus 1.32 and 1.355 for treatment groups 1 and 2, respectively. (A lower MFCR value is an improvement.)

The results of this study demonstrate that both FeQ and a preparation produced according to the method of Example 14 (FeTyr) promote growth and decrease the mortality adjusted feed conversion ratio (MFCR) in the absence or presence of dirty litter contaminated with Campylobacter.

TABLE 4

Effect of treatments on growth performance during starter phase (day 0-11)

| Treatment | ABW Day 0 | ABW Day 11 | AFD | AWG Day 0-11 | MFCR |
|---|---|---|---|---|---|
| 1 | 0.040 | 0.331 | 0.348 | 0.291 | $1.239^b$ |
| 2 | 0.040 | 0.337 | 0.359 | 0.297 | $1.228^b$ |
| 3 | 0.040 | 0.346 | 0.356 | 0.306 | $1.181^{ab}$ |
| 5 | 0.040 | 0.334 | 0.352 | 0.294 | $1.210^{ab}$ |
| 6 | 0.041 | 0.351 | 0.360 | 0.310 | $1.168^a$ |
| 7 | 0.040 | 0.325 | 0.348 | 0.285 | $1.236^b$ |
| 8 | 0.040 | 0.329 | 0.353 | 0.289 | $1.229^b$ |
| P-value | 0.136 | 0.418 | 0.979 | 0.463 | 0.005 |
| SED | 0.000 | 0.013 | 0.016 | 0.013 | 0.018 |
| P-value for contrast | | | | | |
| 1 vs 2 | 0.512 | 0.667 | 0.519 | 0.682 | 0.584 |
| 1 vs 2 to 8 | 0.666 | 0.573 | 0.603 | 0.583 | 0.045 |
| 2 vs 3567 | 0.632 | 0.844 | 0.723 | 0.834 | 0.054 |
| 5 vs 6 | 0.099 | 0.213 | 0.627 | 0.233 | 0.033 |
| 5 vs 7 | 0.141 | 0.466 | 0.804 | 0.494 | 0.170 |
| 2 vs 8 | 0.645 | 0.538 | 0.709 | 0.549 | 0.982 |

$a\text{-}b$ within a column reflects differences between treatments when P < 0.05;
SED = Standard errors of difference of means;
ABW = average body weight (kg);
AFD = average feed intake (kg);
AWG = average weight gain (kg);
MFCR = Mortality adjusted feed conversion ratio;
FCR = Feed conversion ratio-commercial.

TABLE 5

Effect of treatments on growth performance during grower phase (day 11-20)

| Treatment | ABW Day 20 | AFD | AWG Day 11-20 | MFCR |
|---|---|---|---|---|
| 1 | 0.924 | 0.799 | 0.593 | 1.362 |
| 2 | 0.929 | 0.838 | 0.592 | 1.421 |
| 3 | 0.972 | 0.857 | 0.625 | 1.375 |
| 5 | 0.943 | 0.821 | 0.609 | 1.348 |
| 6 | 0.991 | 0.841 | 0.640 | 1.343 |
| 7 | 0.947 | 0.829 | 0.622 | 1.333 |
| 8 | 0.935 | 0.809 | 0.606 | 1.351 |
| P-value | 0.358 | 0.311 | 0.279 | 0.279 |
| SED | 0.032 | 0.025 | 0.021 | 0.036 |
| P-value for contrast | | | | |
| 1 vs 2 | 0.875 | 0.133 | 0.977 | 0.115 |
| 1 vs 2 to 8 | 0.248 | 0.094 | 0.175 | 0.987 |
| 2 vs 3567 | 0.189 | 0.961 | 0.075 | 0.020 |
| 5 vs 6 | 0.145 | 0.427 | 0.160 | 0.884 |
| 5 vs 7 | 0.913 | 0.737 | 0.546 | 0.673 |
| 2 vs 8 | 0.850 | 0.253 | 0.516 | 0.065 |

SED = Standard errors of difference of means;
ABW = average body weight (kg);
AFD = average feed intake (kg);
AWG = average weight gain (kg);
MFCR = Mortality adjusted FCR;
FCR = FCR commercial.

TABLE 6

Effect of treatments on growth performance during period day 20-25.

| Treatment | ABW Day 25 | AFD | AWG Day 20-25 | MFCR |
|---|---|---|---|---|
| 1 | 1.366 | 0.662 | 0.442 | 1.500 |
| 2 | 1.371 | 0.652 | 0.442 | 1.550 |
| 3 | 1.424 | 0.667 | 0.453 | 1.477 |
| 5 | 1.384 | 0.658 | 0.441 | 1.495 |
| 6 | 1.426 | 0.685 | 0.434 | 1.599 |
| 7 | 1.388 | 0.661 | 0.441 | 1.513 |
| 8 | 1.377 | 0.662 | 0.442 | 1.499 |
| P-value | 0.723 | 0.916 | 0.999 | 0.882 |
| SED | 0.044 | 0.026 | 0.030 | 0.096 |
| P-value for contrast | | | | |
| 1 vs 2 | 0.912 | 0.685 | 0.998 | 0.604 |
| 1 vs 2 to 8 | 0.403 | 0.932 | 0.996 | 0.759 |
| 2 vs 3567 | 0.339 | 0.444 | 0.990 | 0.707 |
| 5 vs 6 | 0.361 | 0.311 | 0.826 | 0.294 |
| 5 vs 7 | 0.930 | 0.902 | 0.988 | 0.854 |
| 2 vs 8 | 0.892 | 0.693 | 0.999 | 0.604 |

SED = Standard errors of difference of means;
ABW = average body weight (kg);
AFD = average feed intake (kg);
AWG = average weight gain (kg);
MFCR = Mortality adjusted FCR;
FCR = FCR commercial.

TABLE 7

Effect of treatments on overall growth performance during grower phase (day 11-25)

| Treatment | AFD | AWG Day 11-25 | MFCR |
|---|---|---|---|
| 1 | 1.462 | 1.035 | 1.421 |
| 2 | 1.490 | 1.034 | 1.457 |
| 3 | 1.524 | 1.078 | 1.417 |
| 5 | 1.479 | 1.050 | 1.409 |
| 6 | 1.526 | 1.075 | 1.440 |

TABLE 7-continued

Effect of treatments on overall growth performance during grower phase (day 11-25)

| Treatment | AFD | AWG Day 11-25 | MFCR |
|---|---|---|---|
| 7 | 1.490 | 1.064 | 1.406 |
| 8 | 1.471 | 1.048 | 1.414 |
| P-value | 0.660 | 0.804 | 0.598 |
| SED | 0.042 | 0.036 | 0.030 |
| P-value for contrast | | | |
| 1 vs 2 | 0.516 | 0.984 | 0.241 |
| 1 vs 2 to 8 | 0.293 | 0.406 | 0.891 |
| 2 vs 3567 | 0.657 | 0.267 | 0.118 |
| 5 vs 6 | 0.280 | 0.498 | 0.300 |
| 5 vs 7 | 0.787 | 0.707 | 0.925 |
| 2 vs 8 | 0.664 | 0.695 | 0.165 |

SED = Standard errors of difference of means;
ABW = average body weight (kg);
AFD = average feed intake (kg);
AWG = average weight gain (kg);
MFCR = Mortality adjusted FCR.

TABLE 8

Effect of treatments on overall growth performance during finisher phase (day 25-42)

| Treatment | ABW Day 42 | AFD | AWG Day 25-42 | MFCR |
|---|---|---|---|---|
| 1 | 3.437 | 3.479 | $2.070^b$ | 1.688 |
| 2 | 3.186 | 3.480 | $1.814^a$ | 1.889 |
| 3 | 3.342 | 3.387 | $1.918^{ab}$ | 1.773 |
| 5 | 3.407 | 3.357 | $2.023^b$ | 1.706 |
| 6 | 3.464 | 3.315 | $2.039^b$ | 1.704 |
| 7 | 3.304 | 3.362 | $1.916^{ab}$ | 1.793 |
| 8 | 3.341 | 3.434 | $1.964^{ab}$ | 1.716 |
| P-value | 0.027 | 0.56 | 0.009 | 0.211 |
| SED | 0.075 | 0.099 | 0.062 | 0.081 |
| P-value for contrast | | | | |
| 1 vs 2 | 0.004 | 0.997 | <.001 | 0.022 |
| 1 vs 2 to 8 | 0.110 | 0.247 | 0.016 | 0.233 |
| 2 vs 3567 | 0.004 | 0.129 | 0.004 | 0.035 |
| 5 vs 6 | 0.455 | 0.680 | 0.800 | 0.988 |
| 5 vs 7 | 0.187 | 0.960 | 0.101 | 0.294 |
| 2 vs 8 | 0.053 | 0.649 | 0.027 | 0.046 |

$^{a-b}$within a column reflects differences between treatments when P < 0.05;
SED = Standard errors of difference of means;
ABW = average body weight (kg);
AFD = average feed intake (kg);
AWG = average weight gain (kg);
MFCR = Mortality adjusted FCR;
FCR = FCR commercial.

TABLE 9

Effect of treatments on the growth performance during the experimental period of day 20-42 (after the birds were challenged)

| Treatment | AFD | AWG Day 20-42 | MFCR |
|---|---|---|---|
| 1 | 4.142 | $2.512^b$ | 1.653 |
| 2 | 4.131 | $2.256^a$ | 1.820 |
| 3 | 4.054 | $2.370^{ab}$ | 1.713 |
| 5 | 4.015 | $2.464^{ab}$ | 1.665 |
| 6 | 4.001 | $2.473^{ab}$ | 1.678 |

TABLE 9-continued

Effect of treatments on the growth performance during the experimental period of day 20-42 (after the birds were challenged)

| Treatment | AFD | AWG Day 20-42 | MFCR |
|---|---|---|---|
| 7 | 4.023 | $2.357^{ab}$ | 1.739 |
| 8 | 4.096 | $2.406^{ab}$ | 1.676 |
| P-value | 0.767 | 0.025 | 0.344 |
| SED | 0.110 | 0.068 | 0.075 |
| P-value for contrast | | | |
| 1 vs 2 | 0.926 | 0.001 | 0.038 |
| 1 vs 2 to 8 | 0.306 | 0.028 | 0.290 |
| 2 vs 3567 | 0.229 | 0.008 | 0.055 |
| 5 vs 6 | 0.898 | 0.894 | 0.856 |
| 5 vs 7 | 0.941 | 0.138 | 0.331 |
| 2 vs 8 | 0.752 | 0.042 | 0.070 |

$^{a-b}$within a column reflects differences between treatments when P < 0.05;
SED = Standard errors of difference of means;
ABW = average body weight (kg);
AFD = average feed intake (kg);
AWG = average weight gain (kg);
MFCR = Mortality adjusted.

TABLE 10

Overall effect of treatments on growth performance during the experimental period of day 0-20 (before birds were challenged).

| Treatment | AFD | AWG Day 0-20 | MFCR |
|---|---|---|---|
| 1 | 1.147 | 0.884 | 1.320 |
| 2 | 1.196 | 0.889 | 1.355 |
| 3 | 1.213 | 0.931 | 1.310 |
| 5 | 1.173 | 0.903 | 1.303 |
| 6 | 1.201 | 0.951 | 1.284 |
| 7 | 1.178 | 0.907 | 1.302 |
| 8 | 1.161 | 0.895 | 1.311 |
| P-value | 0.623 | 0.368 | 0.225 |
| SED | 0.038 | 0.032 | 0.025 |
| P-value for contrast | | | |
| 1 vs 2 | 0.215 | 0.881 | 0.181 |
| 1 vs 2 to 8 | 0.191 | 0.251 | 0.627 |
| 2 vs 3567 | 0.860 | 0.188 | 0.012 |
| 5 vs 6 | 0.476 | 0.150 | 0.469 |
| 5 vs 7 | 0.907 | 0.899 | 0.978 |
| 2 vs 8 | 0.371 | 0.846 | 0.094 |

SED = Standard errors of difference of means;
ABW = average body weight (kg);
AFD = average feed intake (kg);
AWG = average weight gain (kg);
MFCR = Mortality adjusted.

TABLE 11

Overall effect of treatment groups on growth performance (day 0-42)

| Treatment | AFD | AWG Day 0-42 | MFCR |
|---|---|---|---|
| 1 | 5.289 | $3.397^b$ | 1.563 |
| 2 | 5.328 | $3.145^a$ | 1.679 |
| 3 | 5.267 | $3.302^{ab}$ | 1.595 |
| 5 | 5.188 | $3.367^{ab}$ | 1.560 |
| 6 | 5.201 | $3.423^b$ | 1.563 |

TABLE 11-continued

Overall effect of treatment groups on growth performance (day 0-42)

| Treatment | AFD | AWG Day 0-42 | MFCR |
|---|---|---|---|
| 7 | 5.201 | $3.265^{ab}$ | 1.612 |
| 8 | 5.258 | $3.301^{ab}$ | 1.577 |
| P-value | 0.920 | 0.028 | 0.193 |
| SED | 0.132 | 0.075 | 0.047 |
| P-value for contrast | | | |
| 1 vs 2 | 0.773 | 0.004 | 0.024 |
| 1 vs 2 to 8 | 0.633 | 0.111 | 0.352 |
| 2 vs 3567 | 0.29 | 0.004 | 0.018 |
| 5 vs 6 | 0.920 | 0.461 | 0.954 |
| 5 vs 7 | 0.924 | 0.190 | 0.284 |
| 2 vs 8 | 0.601 | 0.053 | 0.043 |

$a\text{-}b$ within a column reflects differences between treatments when $P < 0.05$;
SED = Standard errors of difference of means;
ABW = average body weight (kg);
AFD = average feed intake (kg);
AWG = average weight gain (kg);
MFCR = Mortality adjusted.

TABLE 12

The effect of treatments on overall liveability and European production and efficiency factor (EPEF)

| | EPEF | |
|---|---|---|
| Treatment | Day 20 | Day 42 |
| 1 | 318.3 | 282.8 |
| 2 | 334.7 | 250.7 |
| 3 | 350.4 | 262.9 |
| 5 | 352.0 | 278.3 |
| 6 | 364.8 | 265.0 |
| 7 | 354.5 | 276.2 |
| 8 | 336.4 | 296.0 |
| P-value | 0.547 | 0.842 |
| SED | 23.83 | 31.68 |
| P-value for contrast | | |
| 1 vs 2 | 0.500 | 0.323 |
| 1 vs 2 to 8 | 0.111 | 0.645 |
| 2 vs 3567 | 0.285 | 0.437 |
| 5 vs 6 | 0.599 | 0.680 |
| 5 vs 7 | 0.919 | 0.949 |
| 2 vs 8 | 0.945 | 0.170 |

TABLE 13

Effect of treatments on growth performance in absence of *Campylobacter* challenge during starter phase (0-11 days) and period 0-20 days.

| Treatment | ABW Day 11 | ABW Day 20 | AFD 0-20 days | AWG 0-20 days | MFCR 0-20 |
|---|---|---|---|---|---|
| Groups 1 & 2 | 0.334 | 0.927 | 1.172 | 0.887 | 1.3374 |
| FeQ (Groups 3, 5, 6, 7) | 0.339 | 0.963 | 1.191 | 0.923 | 1.2996 |
| P-value | 0.584 | 0.079 | 0.432 | 0.078 | 0.029 |
| SED | 0.009 | 0.020 | 0.024 | 0.020 | 0.016 |

ABW = average body weight (kg);
AFD = average feed intake (kg);
AWG = average weight gain (kg);
MFCR = mortality adjusted feed conversion ratio Example 8

FeDOPA Prevents Attachment of Bacteria to Surfaces

Materials and Methods

Enteropathogenic *E. coli* (EPEC) E2348/69 were grown in wells for 48 hours at 37° C. in the presence of FeDOPA (10-250 μM), and in the absence of FeDOPA (as control). After 48 hours, the wells were washed in order to remove suspended cells. Crystal violet was then added to each well. The wells were then washed to remove excess dye. A mixture of acetone/ethanol was then added to the wells to re-suspend any cells attached to the plastic surface of the wells, and dissolve any dye present. The presence of dye in each well was then quantified by measuring the O.D. at 570 nm.

Results

Figure 12:
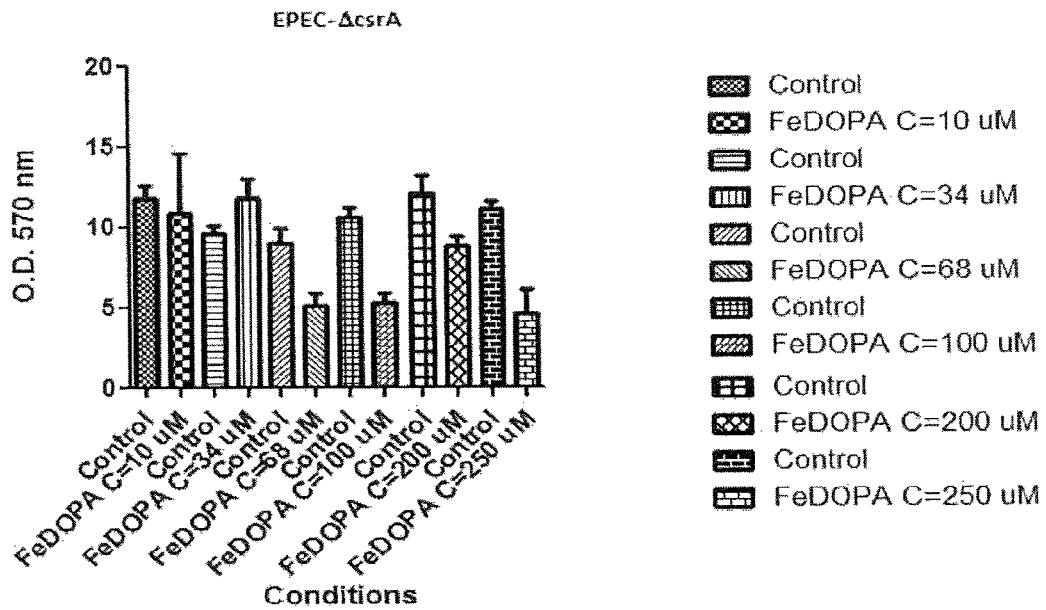
FIG. 12 is shows quantitatively the difference in the attachment of EPEC cells to the plastic well surface in the absence and presence of FeDOPA (also referred to as Fe-DOPA) by measurement of the optical absorbance of crystal violet that was absorbed by EPEC cells attached to the surface.

In the absence of FeDOPA, EPEC binds to the plastic surface and forms a biofilm that is readily detected by dying with crystal violet. However, in the presence of FeDOPA, EPEC attachment to the plastic surface and formation of a biofilm is inhibited. FIG. 12 shows quantitatively the difference in the attachment of EPEC cells to the plastic well surface in the absence and presence of FeDOPA by measurement of the optical absorbance of crystal violet that was absorbed by EPEC cells attached to the surface. At an FeDOPA concentration of 68-250 μM attachment of bacterial cells to the surface and biofilm formation is inhibited.

Example 9

Disruption of a Preformed Biofilm with a Preparation Produced According to the Method of Example 14 ("FeTyr")

Figure 13:
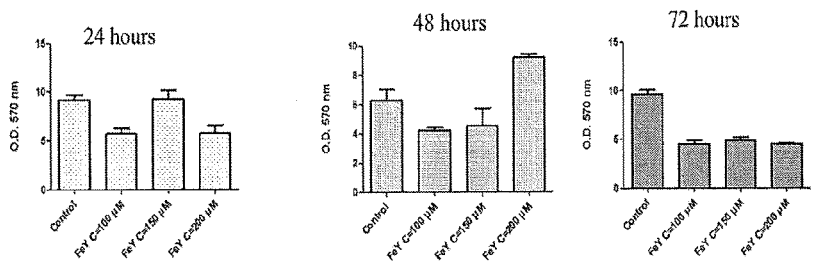
FIG. 13 shows 3 bar graphs at 24, 48 and 72 hours of the optical absorbance of crystal violet that was absorbed by the EPEC cells that remained attached to the surface of the plastic well after a mature biofilm formed by EPEC-pgA$^{++}$ was treated with FeTyr) (shown as "FeY" in FIG. 13) at 100 µM, 150 µM and 200 µM compared to an untreated biofilm (labeled "Control") in a crystal violet assay.

Crystal violet assays were used as described above to demonstrate that FeTyr could disrupt a pre-formed biofilm. A mature biofilm formed by EPEC-pgA$^{++}$ was treated with FeTyr for 24, 48 and 72 hours at FeTyr concentrations of 100 μM, 150 μM and 200 μM and the presence of the biofilm after these times was compared to an untreated biofilm (labeled "Control") using a crystal violet assay. The color of the control wells was more intense in color at 72 hours than those that were treated with FeTyr at 100, 150 and 200 μM for 72 hours. FIG. 13 shows quantitatively the optical absorbance of crystal violet at 570 nm that was absorbed by the EPEC cells that remained attached to the surface of the plastic well after a mature biofilm formed by EPEC-pgA$^{++}$ was treated with FeTyr (shown as FeY in FIG. 13) at 100 μM, 150 μM and 200 μM compared to an untreated biofilm (labeled "Control") in the crystal violet assay. A significantly lower optical absorbance was found at 72 hours for the biofilm treated with FeTyr at 100, 150 and 200 μM at 72 hours. These results demonstrate that a preparation produced according to the method of Example 14 ("FeTyr") can disrupt a pre-formed biofilm.

Example 10

Disruption of a Preformed Biofilm with a Preparation Produced According to the Method of Example 14 ("FeTyr") and Fe-DOPA A BioFlux system was used to demonstrate that a preparation produced according to the method of Example 14 ("FeTyr") and Fe-DOPA can be used to disrupt a mature EPEC-ΔcsrA biofilm. Our studies showed that that a mature biofilm of EPEC-ΔcsrA can be formed in the presence of LB medium 30% v/v and imaged (data not shown). The mature biofilm was treated with FeTyr at concentrations of 100, 150 and 200 μM for 20 hours and compared to a control biofilm that had just been treated with LB medium 30% v/v. It was found that biofilm dispersion increased as the concentration of FeTyr was increased from 100 to 200 μM (data not shown). Mature biofilm was treated with FeDOPA at a concentration of 100 μM for 20 hours and compared to a control biofilm that had just been treated with LB medium 30% v/v. It was found that Fe-DOPA dispersed the biofilm at a concentration of 100 μM (data not shown).

Example 11

Treatment of an Acne Patient with FeQ

An 18 year old female patient was treated continuously for 30 days by applying a solution of ferric quinate (340 μM) to her acne vulgarism ("acne") once each day. Within 5 days of the start of treatment, her acne, which had not previously responded to treatment with antibiotics, began to show signs of healing. After treatment for 30 days, her acne was completely healed. Her acne did not recur even after discontinuation of treatment for over one year.

Example 12

Effect of FeQ on Biofilm Formation of a Medical Device

Materials and Methods

To investigate the effect of Ferric Quinate (FeQ) on the surface integrity of contact lenses, two contact lenses were independently incubated in either saline solution, or saline solution with a final concentration of 340 μM FeQ at 4° C. for 7 days, whilst gently shaking. The lenses were then washed 6 times with phosphate-buffered solution (PBS)+ 0.05% Tween. Each lens was then washed twice with distilled water before analysis via environmental scanning electron microscope (ESEM).

To investigate biofilm formation on the contact lens, clinically determined PAO-1 strains of *Pseudomonas aeruginosa* were incubated with the lenses in either Luria-Bertani Media (LB) or LB with a final concentration of 340 μM FeQ at 37° C. for 24 hours in a non-shaking incubator. The lenses were then washed 6 times with PBS+0.05% Tween, before being stored overnight in PBS+0.05% Tween. In preparation for the ESEM, formaldehyde was added to a final concentration of 1% and incubated for 10 minutes in order to inactivate the bacteria. The lenses were then washed 4 times with PBS+0.05% Tween, and immediately before analysis the lenses were washed a further two times with distilled water.

Results

Surface Integrity

Lenses were treated with 340 μM FeQ or left untreated (control) to investigate the effect, if any, of FeQ treatment on the surface integrity of the contact lens.

The results show that FeQ at 340 μM does not have any visible significant effect (via ESEM) on the surface integrity of the contact lens.

Biofilm Formation

ESEM images (data not shown) following incubation with bacteria only showed large scale biofilm development of *Pseudomonas aeruginosa*, over the surface of the contact lens. Analysis via the ESEM requires vacuum and causes areas of the biofilm to dehydrate, which is responsible for the perforated appearance of the biofilm of the contact lens. The dehydration gives perception of depth, and shows the biofilm formed in the absence of FeQ to be substantial. Individual bacteria were visible in the biofilm, surrounded by the extracellular matrix (ECM).

The impact of incubation with bacteria in the presence of FeQ 340 μM was also investigated. These images (data not shown) showed that, in the presence of FeQ at 340 μM, *Pseudomonas aeruginosa* appears as either single bacterium, or small aggregates of bacteria, with no apparent ECM formation. These results indicate that FeQ inhibits biofilm formation of *Pseudomonas aeruginosa*.

Based on these results, it can be concluded the FeQ and other compounds and preparations as described herein can be used to inhibit or prevent biofilm formation on medical devices, such as but not limited to, contact lenses.

Example 13

Preparation Protocol for K [Fe $(C_7H_{11}O_6)_3$] (OH) $3H_2O$ (FeQ)

$FeCl_3.6H_2O$ (50 g, 184 mmol, Alfa Aesar, 97%) was placed in a flask and dissolved in 300 mL of $H_2O$ (J. T. baker, HPLC grade). To that solution, D-(-)-quinic acid (110 g, 572 rnmol, Buchlr Gmbh, 96%) was added slowly with continuous stirring. The pH of the solution was adjusted to ~3 by addition of 10M KOH (Alfa Aesar, 85%) (~80 mL was required).

The dark yellow solution darkened to brownish upon addition of KOH. The dark solution was stirred for 1 h at room temperature. After stifling at room temperature for 1 h ethanol (EMD, 94%) (2.5 ) was added slowly to the solution with stirring.

After addition of approximately ¼ of the total ethanol, the solution lightened visibly and a fine solid began to precipitate from solution. After addition of the remaining ethanol, the solution is allowed to sit overnight at room temperature.

The solids are collected by vacuum filtration on a fritted funnel and allowed to dry on the funnel while the vacuum is continued for 2-3 h. The bright yellow solid is spread in a thin layer in a drying dish and dried open to the air for 3 days followed by drying under vacuum for 48 h to give 155 g of the final product.

Example 14

Exemplary Method for the Synthesis of a Preparation According to the Present Invention ("FeTyr")

A preparation was prepared by a method in which L-tyrosine and $LiOH.H_2O$ were dissolved in water and the solution heated. $FeCl_3$ salt was dissolved in water and was added to the tyrosine/LiOH solution. Precipitation (brown solid) was almost instantaneous but stirring with heating continued. The product was then allowed to cool and was collected by filtration. The product was air dried and then further dried, for example using a lyophilizer.

More specifically, in one particular example of the aforementioned method, L-tyrosine (5.43 g, 30 mmol, Chem Impex, 99.5%) and $LiOH.H_2O$ (1.26 g, 30 mmol, EMD, 94%) were dissolved in water (250 ml, J. T. Baker, HPLC grade)) and the solution heated to 70° C. for 20 min. The $FeCl_3$ salt (1.62 g, 10 mmol, Alfa Aesar, 98%)) was dissolved in a minimum quantity of water (3-5 ml) and was added to the tyrosine/LiOH solution.

Precipitation (brown solid) was almost instantaneous but stirring with heating continued, such as for 15 min. The product was allowed to cool to room temperature and was collected by filtration. The product was air dried and then further dried in a lyophilizer Isolated yield obtained from the specific method as described in the foregoing paragraph was 5.85 g.

Preliminary elemental analysis of the product produced by the specific methodology described above showed: carbon 49.19%, hydrogen 5.37%, nitrogen 6.33%, oxygen 30.48% and iron 8.63%.

Further preliminary analysis of the product, as produced by the specific methodology described above, indicated:

Ignition on loss (ash) 550° C. for 6 hours: 13.32%
Moisture, vacuum, 100° C., 5 hours 2.23%

Example 15

MALDI-TOF Analysis of an Exemplary Preparation According to the Present Invention The product, as produced by the specific methodology described in Example 14 was further assessed using MALDI-TOF mass spectrum. An objective of the analysis was to confirm the molecular weight of a 1:3 complex of iron (III) and tyrosine.

Summary and Conclusions

The MALDI-TOF mass spectrum of the sample contained a peak at 619.37 Da., consistent with the expected iron (III) and tyrosine complex (in a ratio of 1:3) plus sodium cationization.

A number of other unidentified peaks were also seen in the 400 to 700 Da mass range. Two of the unidentified peaks may be related to the 1:3 iron to tyrosine complex or other complex, hydrate or salt formation between iron and tyrosine. These appear at around 591 and around 647 Da., a difference of 28 Da. less and more than the complex, respectively. The structures corresponding to these peaks are not known, and may represent unidentified structures within the preparation.

Example 16

Alternative Exemplary Method for the Synthesis of a Preparation According to the Present Invention ("FeTyr")

L-tyrosine and lithium hydroxide monohydrate were dissolved in water and the solution heated. Anhydrous iron (III) chloride was dissolved in water and was added to the tyrosine/LiOH solution. Precipitation (brown solid) was almost instantaneous but stirring with heating continued. The product was allowed to cool to room temperature and collected by filtration. The product was then washed with warm water, air dried, and then further dried, for example using a vacuum oven.

More specifically, in one particular example of the aforementioned method, L-tyrosine (330 g, 1.82 mol, Chem Impex, Catalogue #00304, 99.5%) and lithium hydroxide monohydrate (76.5 g, 1.82 mol, EMD, Catalogue #LX0350-5, 94%) were dissolved in water (17 L) and the solution heated to 70° C. for 20 min Anhydrous iron (III) chloride (97.5 g, 0.6 mol, Alfar Aesar, Product #12357, 98%) was dissolved in 100 ml of water and was added to the tyrosine/LiOH solution. Precipitation (brown solid) was almost instantaneous but stirring with heating continued for 15 min. The product was allowed to cool to room temperature overnight and was collected by filtration. The product was washed with warm water (70° C., 2 L), air dried for 2 days and then dried in a vacuum oven at 40° C. for 2 days. Typical isolated yield was 350 g (98% yield).

Example 17

Further Alternative Exemplary Method for the Synthesis of a Preparation According to the Present Invention ("FeTyr")

$FeCl_3$ was added to a suspension of tyrosine and $Et_3N$ in methanol and refluxed. The colour changed to violet immediately upon addition. The solid was filtrated and air-dried and then further dried, for example, over $CaCl_2$ under vacuum.

More specifically, in one particular example of the aforementioned method, $FeCl_3.6H_2O$ (1 mmol, 0.27 g) was added to a suspension of tyrosine (3 mmol, 0.543 g) and $Et_3N$ (3 mmol, 0.303 g, 0.41 mL) in 100 mL methanol at 75° C. and refluxed for 24 hrs. The colour changed to violet immediately upon addition. The solid was filtered and air-dried and then dried over $CaCl_2$ under vacuum.

Example 18

Synthesis of Fe(DOPA)$_3$

L-Dopa (11.84 g, 60 mmol, AK Scientific, 98%) and $LiOH.H_2O$ (2.52 g, 60 mmol, EMD, 94%) were dissolved in water (100 ml, J. T. Baker, HPLC grade) and the solution heated to 70° C. for 20 mm The $FeCl_3$ salt (3.2 g, 20 mmol, Alfa Aesar, 98%) was dissolved in a minimum quantity of water (6-10 ml) and was added to the Dopa/LiOH solution vigorous.

Precipitation (very dark purple) was almost instantaneous but stirring with heating continued for 15 min.

The product was allowed to cool to room temperature and was collected by filtration. The product was air dried and then further dried in a lyophilizer Isolated yield was 6.5 g. More solid (4 g) was collected from the filtrate and dried in the same way. Overall yield was 10.5 g.

Example 19

Fe-Q and Fe-Phe Potentiate the Effect of Antibiotics

Methods

To investigate effects upon antibiotic resistance, a laboratory strain of *Pseudomonas aeruginosa* (PAO1N) and a mixed population of clinical isolates (PAO Mixed) were incubated in Luria-Bertani (LB) media alone, or with different concentrations (34 μM, 100 μM, 200 μM and 340 μM) of FeQ or FePhe.

Each of the different media, bar one control, contained 10 μg/ml of the aminoglycoside antibiotic Amikacin.

10 μl of the bacterial strains were added into each well of a 96-well micro-titer plate, before 290 μl of the relevant media was added to wells. Each different condition was repeated in sextuplicate.

The plate was incubated at 37° C. within a micro-titer plate reader for 17.5 hours, with the $OD_{600}$ read every 30 minutes.

Results

Figure 14A:
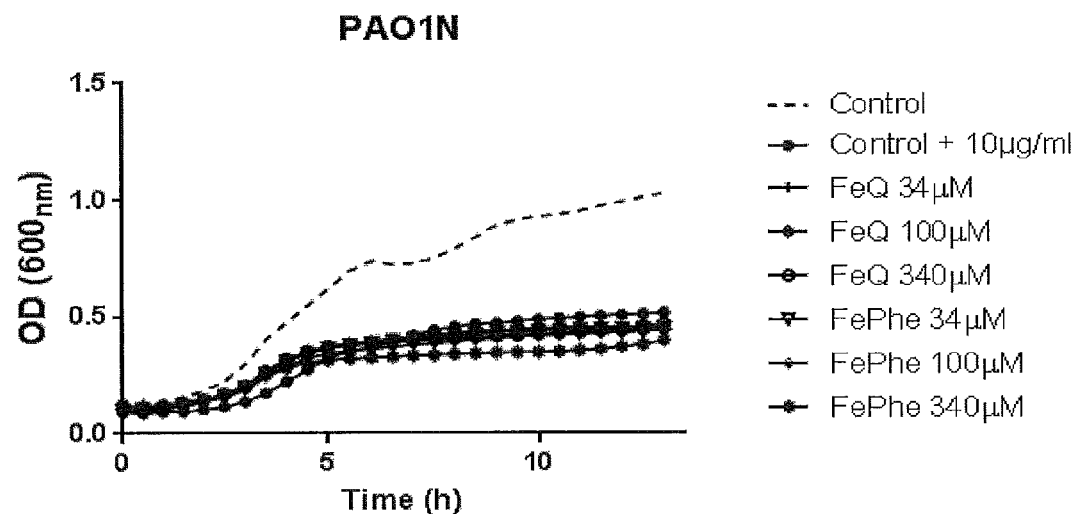
FIGS. 14A and B show the results of Example 30, which investigate effects upon antibiotic resistance of a laboratory strain of *Pseudomonas aeruginosa* (PAO1N) and a mixed population of clinical isolates (PAO Mixed), when incubated in Luria-Bertani (LB) media alone, or with different concentrations (34 µM, 100 µM, 200 µM and 340 µM) of FeQ or FePhe.
Figure 14B:
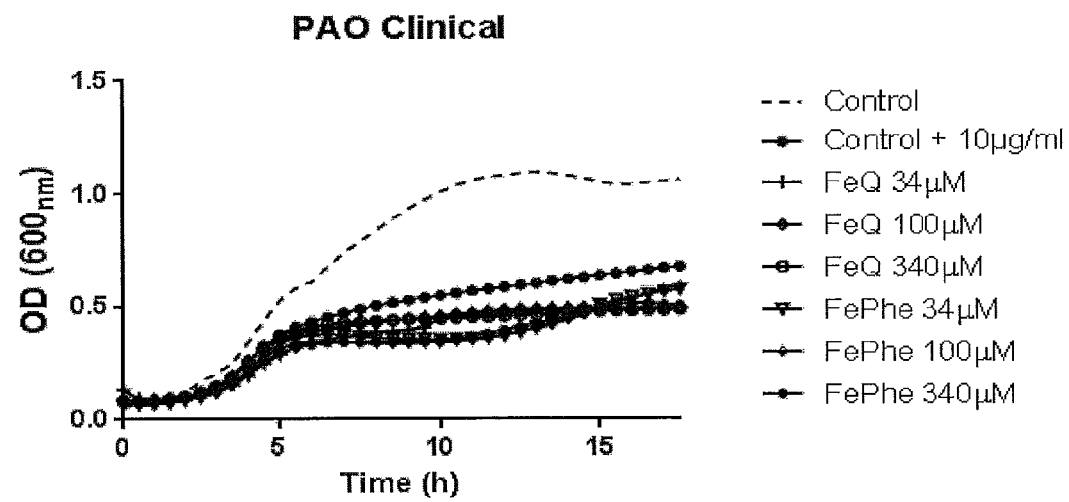
FIG. 14B shows the results with PAO Mixed cultures.

The results are shown in FIGS. 14A and 14B. These figures show that Fe-Q and Fe-Phe provide similar effects at reducing tolerance of PAO1N and PAO Mixed to the aminoglycoside Amikacin Example 20

Further Alternative Exemplary Method for the Synthesis of a Preparation According to the Present Invention ("FeTyr")

Methods

L-tyrosine (50 g, 0.275 mol) and lithium hydroxide monohydrate (11.57 g, 0.275 mol) were suspended in water (2.6 , 52 Vol.) and the mixture was heated to 70 -75° C. for 30 min. The solution became, clear and homogeneous.

Iron (III) chloride hexahydrate (24.6 g, 0.091 mol) was dissolved in water (15 mL, 0.3, Vol.) at ambient temperature. The solution was further diluted with water (85 Ml, 1.7 Vol.) to enable gradual and addition of aqueous iron (III) chloride solution into the pre-dissolved tyrosine/LiOH aqueous solution at 70 -75° C. over a period of time of less than 5 minutes. Aqueous $FeCl_3$ solution was added into tyrosine solution at 70 -75° C. over a period of time of less than 5 minutes. During the addition of aq. $FeCl_3$ solution, precipitation was observed.

The heating mantle was turned off and the reaction mixture was gradually allowed to attain room temperature. An increase in the precipitation was observed as the reaction mixture was cooled. The suspension was stirred for 16 -18 h at 25 -35° C. after which the precipitation of the product was completed.

Afterwards, the filtration of the suspension and washing of the wet cake with warm water (~70° C.; 300 mL, 6 Vol.) and air drying of the isolated material for ~16 h followed by vacuum drying at below 45° C. for 2 -4 h was performed to obtain 49 g of the Fe-Tyr product.

Results

Characterization:

Elemental Analysis:

Elemental analysis (see Table 14 below) suggested that FeTyr produced by the instant method was not simply made up of an $Fe(tyr)_3$ compound but of a mixture which included an $Fe(tyr)_3$ compound. Based on the low carbon and high oxygen in the "found" analysis numbers, water was added to the formula. Addition of three waters of hydration showed a better carbon and hydrogen match with oxygen being low. Iron carboxylates often form trimers, with a triply-bridging oxygen at the center. Keeping the same relative Fe/tyrosine/water ratio, but formulating it as a μ-oxo trimer, the elemental analysis is within acceptable limits for all elements.

TABLE 14

Elemental Analysis Data for FeTyr product

|  | H | C | N | O | Fe |
|---|---|---|---|---|---|
| Found | 5.37 | 49.19 | 6.33 | 30.48 | 8.63 |
| $Fe(tyr)_3$ | 5.07 | 54.38 | 7.05 | 24.14 | 9.36 |

TABLE 14-continued

Elemental Analysis Data for FeTyr product

|  | H | C | N | O | Fe |
|---|---|---|---|---|---|
| $Fe(tyr)_3 \cdot 3H_2O$ | 5.58 | 49.86 | 6.46 | 29.52 | 8.59 |
| $Fe_3O(tyr)_9 \cdot 9H_2O$ | 5.53 | 49.45 | 6.41 | 30.09 | 8.52 |

We claim:

1. An animal feed comprising an Fe(III)-tyrosine complex, in an effective amount to reduce the number of Campylobacter present in the gastrointestinal tract of an animal, wherein the Fe(III)-tyrosine complex is prepared by a method comprising bringing a tyrosinate moiety into contact with an Fe(III)-containing substance in the presence of a base, wherein the base is an amine, or alkali metal hydroxide.

2. The animal feed of claim 1, further comprising one or more antimicrobial agents.

3. The animal feed of claim 2, wherein the amount or concentration of the one or more antimicrobial agents in the product is at least 5%, less than a therapeutically effective amount or concentration of the one or more antimicrobial agents when administered to the patient or animal that is not in receipt of the product.

4. The animal feed of claim 2, wherein the one or more antimicrobial agents are selected from the group consisting of aminoglycosides, ansaycins, carbapenems, cephalosporins, glycopeptides, lincosamides, lipopeptides, macrolides, monobactams, nitrofurans, oxazolidinones, penicillins, polypeptides, quinolones/fluoroquinolone, sulfonamides, tetracyclines, clofazimine, dapsone, capreomycin, cycloserine, ethambutol, ethionamide, isoniazid, pyrazinamide, rifampicin (rifampin), rifabutin, rifapentine, streptomycin, arsphenamine, chloramphenicol, fosfomycin, fusidic acid, metronidazole, mupirocin, platensimycin, quinupristinldalfopristin, thiamphenicol, tigecycline, tinidazole, and trimethoprim; and combinations thereof.

5. The animal feed of claim 1, wherein the Fe (III) complex and one or more antimicrobial agents is effective for the treatment of an infection or inhibit colonization by one or more microorganisms.

6. The animal feed of claim 1, wherein the tyrosinate moiety is tyrosine or a tyrosine salt.

7. The animal feed of claim 1, wherein the Fe(III)-containing substance is selected from the group consisting of $FeCl_3$, $FeBr_3$, $Fe(OH)_3$, $Fe_2(SO_4)_3$, $FePO_3$, $Fe(HSO_4)_3$, $Fe(NO_3)_3$, $Fe(acetylacetonate)_3$, $Fe(acetate)_3$ and $Fe(lactate)_3$, and hydrates thereof.

8. The animal feed of claim 1, wherein the Fe(III)-containing substance is iron (III) chloride hexahydrate.

9. The animal feed of claim 1, wherein the bringing step occurs in about 5 minutes.

10. The animal feed of claim 1, wherein the tyrosine or other tyrosinate moiety comprises at least 30% L tyrosine or an L-tyrosinate moiety.

11. The animal feed of claim 1, wherein the method does not include a step of isolating Fe(tyrosine)₃ from one or more components of the reaction mixture.

12. The animal feed of claim 1, wherein the Fe(III) containing substance is $Fe(OH)_3$.

* * * * *